(12) United States Patent
Jain et al.

(10) Patent No.: US 8,088,804 B2
(45) Date of Patent: Jan. 3, 2012

(54) N-HYDROXYAMIDE DERIVATIVES POSSESSING ANTIBACTERIAL ACTIVITY

(75) Inventors: Rakesh Kumar Jain, Fremont, CA (US); Mikhail Fedorovich Gordeev, Castro Valley, CA (US); Jason Gustaf Lewis, Castro Valley, CA (US); Charles Francavilla, Fremont, CA (US)

(73) Assignee: Pfizer Inc., New York, NY (US)

( * ) Notice: Subject to any disclaimer, the term of this patent is extended or adjusted under 35 U.S.C. 154(b) by 573 days.

(21) Appl. No.: 12/097,307

(22) PCT Filed: Dec. 4, 2006

(86) PCT No.: PCT/IB2006/003549
§ 371 (c)(1),
(2), (4) Date: Mar. 5, 2009

(87) PCT Pub. No.: WO2007/069020
PCT Pub. Date: Jun. 21, 2007

(65) Prior Publication Data
US 2010/0022605 A1 Jan. 28, 2010

Related U.S. Application Data

(60) Provisional application No. 60/750,600, filed on Dec. 15, 2005.

(51) Int. Cl.
*A61K 31/34* (2006.01)
*A61K 31/381* (2006.01)
*A61K 31/40* (2006.01)
*A61K 31/415* (2006.01)
*A61K 31/426* (2006.01)

(52) U.S. Cl. ........ 514/365; 514/406; 514/423; 514/438; 514/471; 548/200; 548/375.1; 548/537; 548/487; 549/77

(58) Field of Classification Search .................. 514/365, 514/406, 423, 438, 471; 548/200, 375.1, 548/537; 549/487, 77
See application file for complete search history.

(56) References Cited

U.S. PATENT DOCUMENTS
4,077,998 A 3/1978 Fessler et al.
(Continued)

FOREIGN PATENT DOCUMENTS
WO 9705105 2/1997
(Continued)

OTHER PUBLICATIONS

Burdick, D J et al., "N-Benzoyl Amino Acids as LFA-1/ICAM Inhibitors 1: Amino Acid Structure-Activity Relationship", Bioorganic & Medicinal Chemistry Letters, 2003, pp. 1015-1018, vol. 13, No. 6, Oxford, GB.

(Continued)

*Primary Examiner* — Jennifer M Kim
(74) *Attorney, Agent, or Firm* — J. Michael Dixon; Gregg C. Benson

(57) ABSTRACT

Described herein are N-hydroxyamide antibacterial compounds, methods for making the compounds, pharmaceutical compositions containing the compounds and methods of treating bacterial infections utilizing the compounds and pharmaceutical compositions compound of Formula (I): or a salt, solvate ti hydrate thereof, wherein A is (a) each ⌇indicates a point of attachment.

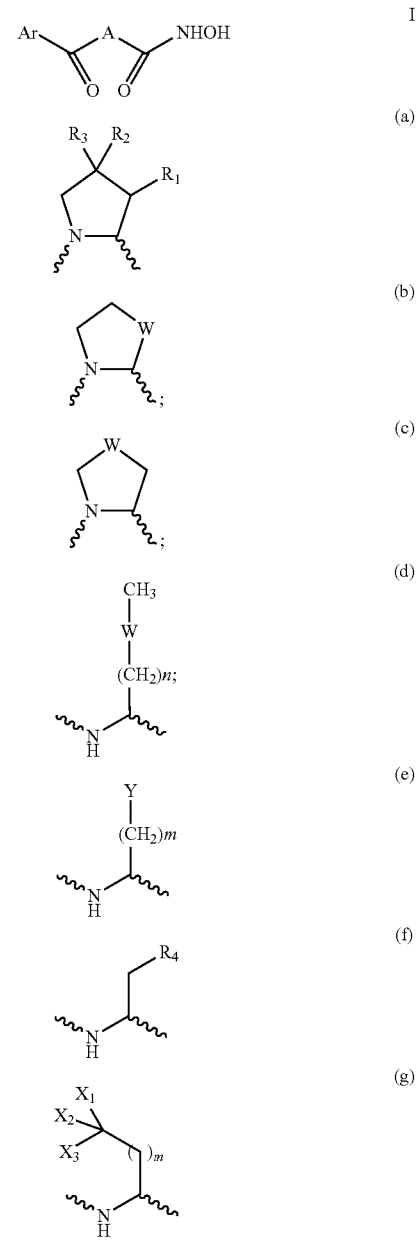

7 Claims, No Drawings

U.S. PATENT DOCUMENTS

| | | | |
|---|---|---|---|
| 6,218,389 B1 | 4/2001 | Almstead et al. | |
| 6,693,123 B2 | 2/2004 | Sebti et al. | |
| 7,208,601 B2 | 4/2007 | Mjalli et al. | |
| 2008/0269282 A1* | 10/2008 | Clauzel et al. | 514/311 |
| 2010/0152188 A1 | 6/2010 | Srinivas et al. | |

FOREIGN PATENT DOCUMENTS

| | | |
|---|---|---|
| WO | 97/17070 A1 | 5/1997 |
| WO | 2004007444 | 1/2004 |
| WO | 2004062601 | 7/2004 |
| WO | 2005037257 | 4/2005 |
| WO | 2006013209 | 2/2006 |
| WO | 2006/040646 A1 | 4/2006 |
| WO | 2007017728 | 2/2007 |

OTHER PUBLICATIONS

Grant, Stephan K, et al., "Inhibition and Structure/Activity Studies of Methionine Hydroxamic Acid Derivatives with Bacterial Peptide Deformylase", Bioorganic Chemistry, 2001, pp. 211-222, vol. 29.

Grant et al., Bioorganic Chemistry, vol. 29, pp. 211-222 (2001).

\* cited by examiner

N-HYDROXYAMIDE DERIVATIVES POSSESSING ANTIBACTERIAL ACTIVITY

FIELD

Provided herein are N-hydroxyamide derivatives which inhibit UDP-3-O—(R-3-hydroxymyristoyl)-N-acetylglucosamine deacetylase (LpxC) and as a result, have gram negative antibacterial activity.

BACKGROUND

Lipid A is the hydrophobic anchor of lipopolysaccharide (LPS) and forms the major lipid component of the outer monolayer of the outer membrane of Gram-negative bacteria. Lipid A is required for bacterial growth and inhibition of its biosynthesis is lethal to the bacteria. Furthermore, blocking Lipid A biosynthesis increases the sensitivity of bacteria to other antibiotics.

One of the key enzymes of bacterial lipid A biosynthesis is LpxC. LpxC catalyzes the removal of the N-acetyl group of UDP-3-O—(R-3-hydroxymyristoyl)-N-acetylglucosamine. The LpxC enzyme is essential in Gram negative bacteria for the biosynthesis of Lipid A, and it is notably absent from mammalian genomes. Since LpxC is essential for Lipid A biosynthesis and inhibition of Lipid A biosynthesis is lethal to bacteria, inhibitors of LpxC have utility as antibiotics. In addition, the absence of LpxC from mammalian genomes reduces potential toxicity of LpxC inhibitors in mammals. Accordingly, LpxC is an attractive target for antibacterial drug discovery.

By way of example, U.S. Pat. No. 5,925,659 teaches that certain heterocyclic hydroxamate compounds, in particular oxazoline compounds, have the ability to inhibit LpxC.

Accordingly, compounds, which possess LpxC inhibitory activity, are desired as potential antibacterial agents.

SUMMARY

One embodiment provides compounds of Formula I:

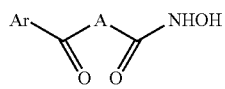
I or a salt, solvate or hydrate thereof,
wherein A is (a)
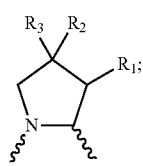

(b)
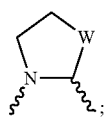

(c)
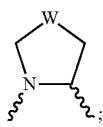

(d)
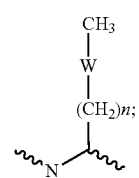

(e)
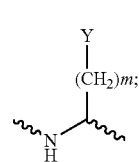

(f)
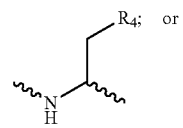

(g)
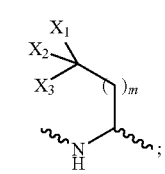

each ⁓⁓ indicates a point of attachment;

$R_1$ is selected from the group consisting of H, $N_3$, $NH_2$, $NHSO_2CH_3$, NHCOH, $NHCH_3$, F, $OCH_3$, and OH;

$R_2$ is selected from the group consisting of H, OH, and $NH_2$;

$R_3$ is selected from the group consisting of H and $CH_2OCH_3$;

$R_4$ is selected from the group consisting of $CH_2SCH_3$, $CH_2SO_2CH_3$, $SCH_3$, $SO_2CH_3$, and

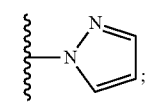

W is selected from the group consisting of S, SO, and $SO_2$;

$X_1$, $X_2$, and $X_3$ are each independently selected from the group consisting of H and F, provided that at least one of $X_1$, $X_2$, and $X_3$ is F;

Y is a heteroaryl;

m is 0 or 1;

n is 1 or 2;

Ar is an optionally substituted aryl or heteroaryl;

with the proviso that the compound is not a compound set forth in Table 1(a)-1(d).

Forms of the compounds can include salts, such as pharmaceutically acceptable salts, solvates, hydrates or prodrugs of the described compounds. The described compounds can also be part of a pharmaceutical composition, which can additionally include a pharmaceutically acceptable carrier, diluent or excipient.

Such compounds and compositions exhibit antibacterial activity and can be used accordingly.

DETAILED DESCRIPTION

Provided are N-hydroxyamide derivatives which inhibit LpxC and thereby possess Gram negative antibacterial activity.

A subset of the compounds of Formula I are the compounds of Formula I(a):

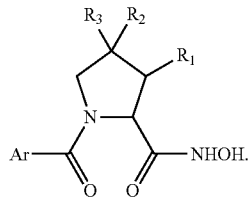

When the compound has a structure of Formula I(a) then the compound is not a compound set forth in Table 1(a):

TABLE 1 (a)

| Structure | Name | Reference(s) |
|---|---|---|
| 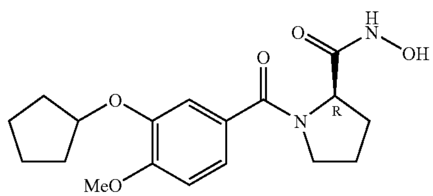 | (R)-1-[3-(cyclopentyloxy)-4-methoxybenzoyl]-N-hydroxy-2-Pyrrolidinecarboxamide CAS Registry No. 188030-38-8 | WO 97/05105 |
| 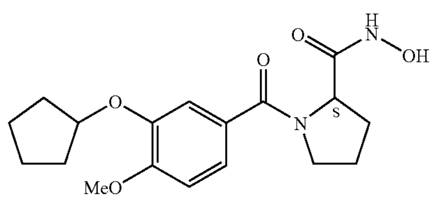 | (S)-1-[3-(cyclopentyloxy)-4-methoxybenzoyl]-N-hydroxy-2-Pyrrolidinecarboxamide CAS Registry No. 188030-39-9 | WO 97/05105 |
| 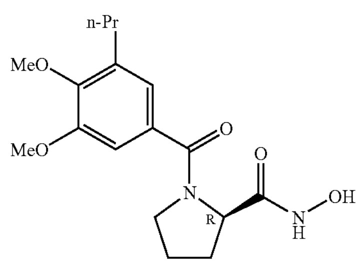 | (2R)-1-(3,4-dimethoxy-5-propylbenzoyl)-N-hydroxy-2-Pyrrolidinecarboxamide or (R)-1-(3,4-Dimethoxy-5-propylbenzoyl)pyrrolidine-2-carboxylic acid hydroxyamide CAS Registry No. 647854-52-2 | WO 2004/007444 |
| 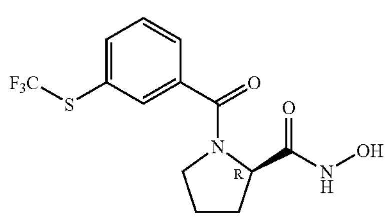 | (2R)-N-hydroxy-1-[3-[(trifluoromethyl)thio]benzoyl]-2-Pyrrolidinecarboxamide or (R)-1-(3-Trifluoromethyl-thiobenzoyl)pyrrolidine-2-carboxylic acid hydroxyamide CAS Registry No. 647857-28-1 | WO 2004/007444 |
| 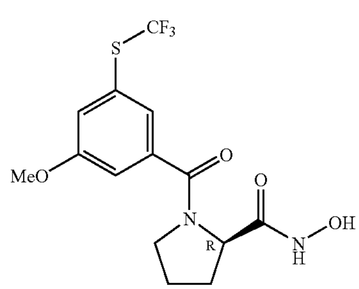 | (2R)-N-hydroxy-1-[3-methoxy-5-[(trifluoromethyl)thio]benzoyl]-2-Pyrrolidinecarboxamide or (R)-1-(3-Methoxy-5-trifluoromethylthio-benzoyl)pyrrolidine-2-carboxylic acid hydroxyamide CAS Regsitry No. 647857-30-5 | WO 2004/007444 |

TABLE 1 (a)-continued

| Structure | Name | Reference(s) |
|---|---|---|
| 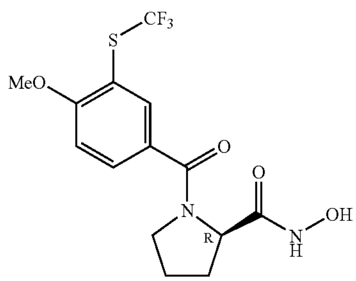 | (2R)-N-hydroxy-1-[4-methoxy-3-[(trifluoromethyl)thio]benzoyl]-2-Pyrrolidinecarboxamide or (R)-1-(4-Methoxy-3-trifluoromethylthio-benzoyl)pyrrolidine-2-carboxylic acid hydroxyamide CAS Registry No. 647857-32-7 | WO 2004/007444 |
| 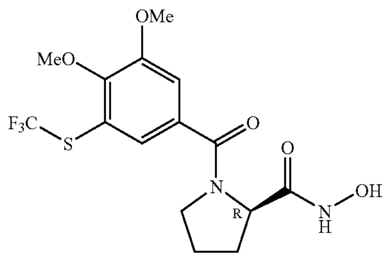 | (2R)-1-[3,4-dimethoxy-5-[(trifluoromethyl)thio]benzoyl]-N-hydroxy-2-Pyrrolidinecarboxamide or (R)-1-(3,4-Dimethoxy-5-trifluoromethylthio-benzoyl)pyrrolidine-2-carboxylic acid hydroxyamide CAS Registry No. 647854-34-9 | WO 2004/007444 |
| 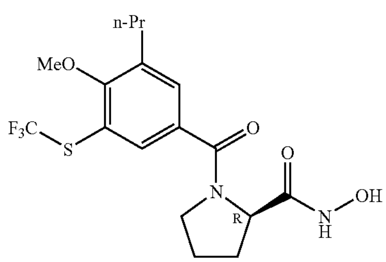 | (2R)-N-hydroxy-1-[4-methoxy-3-propyl-5-[(trifluoromethyl)thio]benzoyl]-2-Pyrrolidinecarboxamide or (R)-1-(4-Methoxy-3-propyl-5-trifluoromethyl-thiobenzoyl)pyrrolidine-2-carboxylic acid hydroxyamide CAS Registry No. 647857-36-1 | WO 2004/007444 |
| 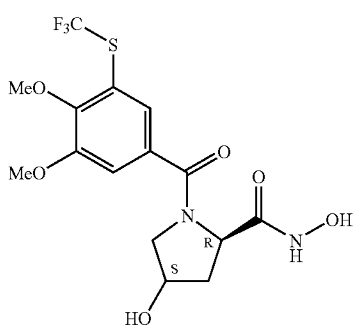 | (2R,4S)-1-[3,4-dimethoxy-5-[(trifluoromethyl)thio]benzoyl]-N,4-dihydroxy-2-Pyrrolidinecarboxamide or (2R,4S)-1-(3,4-Dimethoxy-5-trifluoro-methylthiobenzoyl)-4-hydroxypyrrolidine-2-carboxylic acid hydroxamide CAS Registry No. 647857-49-6 | WO 2004/00744 |
| 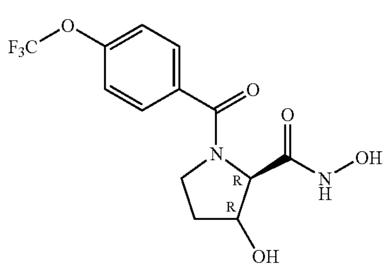 | (2R,3R)-N,3-dihydroxy-1-[4-(trifluoromethoxy)benzoyl]-2-Pyrrolidinecarboxamide CAS Registry No. 728865-11-0 | WO 2004/062601 |

TABLE 1 (a)-continued

| Structure | Name | Reference(s) |
|---|---|---|
| 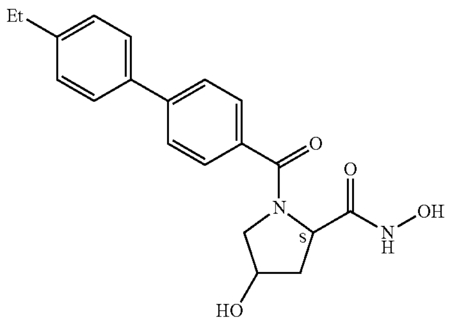 | (2S)-1-[(4'-ethyl[1,1'-biphenyl]-4-yl)carbonyl]-N,4-dihydroxy-2-Pyrrolidinecarboxamide CAS Registry No. 728867-85-4 | WO 2004/062601 |
| 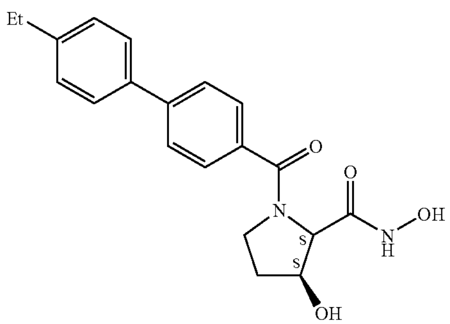 | (2S,3S)-1-[(4'-ethyl[1,1'-biphenyl]-4-yl)carbonyl]-N,3-dihydroxy-2-Pyrrolidinecarboxamide CAS Registry No. 728868-25-5 | WO 2004/062601 |

Although the first two compounds set forth in Table 1(a) are excluded as compounds claimed in the present invention, they are expected to have antibacterial activity and, accordingly, the use of these compounds as antibacterial agents falls within the scope of the present invention.

In some embodiments of the compounds of Formula I(a) $R_1$, $R_2$ and $R_3$ are not all H. In some additional embodiments, when $R_1$ is —OH, then at least one of $R_2$ and $R_3$ is not H.

In compounds of Formula I(a) $R_1$ may be H, $N_3$, —$NH_2$, —$NHSO_2CH_3$, NHCOH, $NHCH_3$, F, —$OCH_3$, or OH; $R_2$ may be H, OH, or $NH_2$; $R_3$ may be H or —$CH_2OCH_3$; and Ar may be an optionally substituted aryl or heteroaryl. Although Ar includes any optionally substituted aryl or heteroaryl, in one embodiment, Ar may also include the following substituted aryl compound.

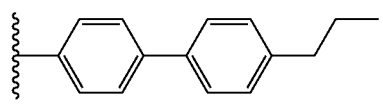

Particular embodiments also include compounds with the following substituents wherein:
$R_1$ is $NH_2$, $R_2$ is H, and $R_3$ is H;
$R_1$ is H, $R_2$ is OH, and $R_3$ is $CH_2OCH_3$;
$R_1$ is $N_3$, $R_2$ is H, and $R_3$ is H;
$R_1$ is $NHSO_2CH_3$, $R_2$ is H, and $R_3$ is H;
$R_1$ is NHCOH, $R_2$ is H, and $R_3$ is H;
$R_1$ is $NHCH_3$, $R_2$ is H, and $R_3$ is H;
$R_1$ is F, $R_2$ is H, and $R_3$ is H;
$R_1$ is $OCH_3$, $R_2$ is H, and $R_3$ is H;
$R_1$ is OH, $R_2$ is OH, and $R_3$ is H; and
$R_1$ is OH, $R_2$ is $NH_2$, and $R_3$ is H.

In some of these compounds, when $R_1$ is OH, $R_2$ and $R_3$ are not both H and/or when $R_2$ is OH, both $R_1$ and $R_3$ are not H.

A subset of the compounds of Formula I(a) includes compounds of Formula I(a)(i):

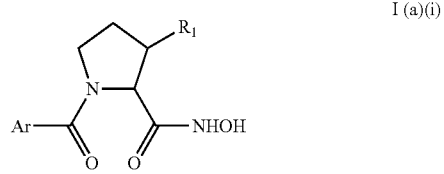

wherein $R_1$ may be $N_3$, $NH_2$, $NHSO_2CH_3$, NHCOH, $NHCH_3$, F, or $OCH_3$; and wherein Ar is an optionally substituted aryl or heteroaryl. These compounds can have the following stereochemistry:

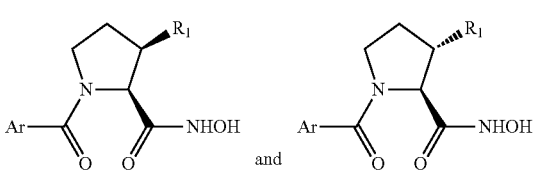

Although Ar includes any optionally substituted aryl or heteroaryl, in one embodiment, Ar may include the following substituted aryl compound.

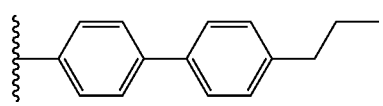

Some compounds having Formula I(a) include compounds 1-8 of Table 2.

Another subset of the compounds of Formula I(a) includes compounds of Formula I(a)(ii):

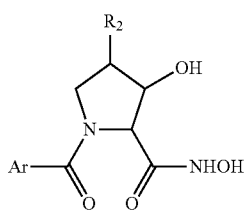

I(a)(ii)

wherein $R_2$ may be OH or $NH_2$; and wherein Ar may be an optionally substituted aryl or heteroaryl. Compounds of this formula also include compounds with the following stereochemistry:

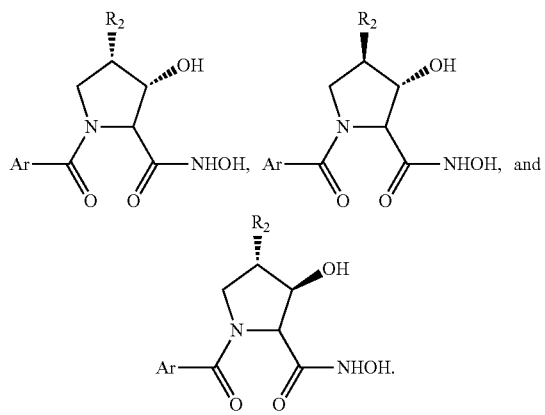

Although Ar includes any optionally substituted aryl or heteroaryl, in one embodiment, Ar may also include the following substituted aryl compound.

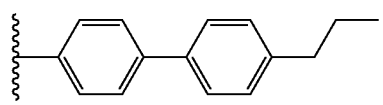

Specific compounds having Formula I(a)(ii) include compounds 9-12 of Table 2.

Another subset of the compounds of Formula I include compounds of Formula I(b):

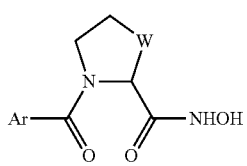

I(b)

wherein W may be S, SO, or $SO_2$; and Ar may be an optionally substituted aryl or heteroaryl. These compounds can include compounds with the following stereochemistry:

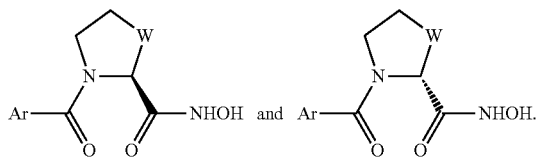

Although Ar includes any optionally substituted aryl or heteroaryl, in one embodiment, Ar may also include the following substituted aryl compounds.

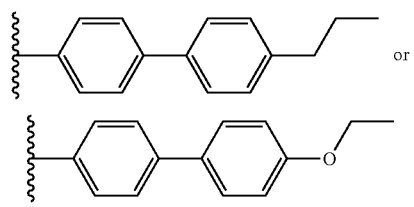

A subset of the compounds of Formula I(b) include compounds of Formula I(b)(i)

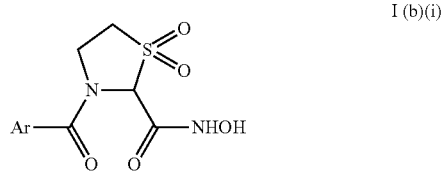

I(b)(i)

These compounds also include compounds with the following stereochemistry:

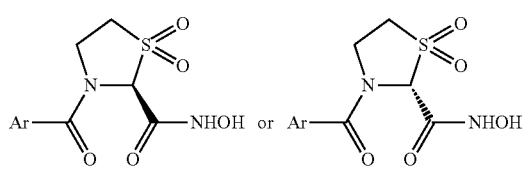

Although Ar includes any optionally substituted aryl, in one embodiment, Ar may also include the following substituted aryl compounds.

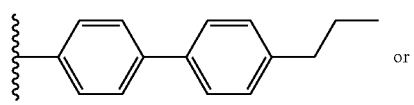

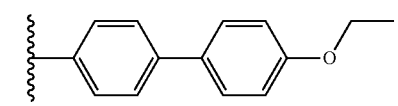

Particular embodiments of Formula I(b) include compounds 13-15, 18, 19 and 33 of Table 2

Another subset of the compounds of Formula I include compounds of Formula I(c):

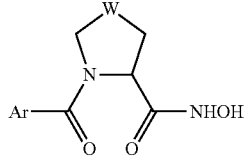  I(c)

wherein W may be S, SO or SO₂; and Ar may be an optionally substituted aryl or heteroaryl. These compounds also include a compound with the following stereochemistry:

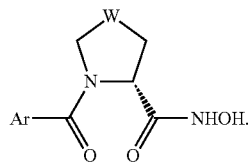

Although Ar includes any optionally substituted aryl or heteroaryl, in one embodiment, Ar may also include the following substituted aryl compound.

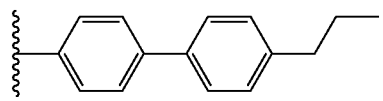

Particular embodiments of Formula I(c) include compounds 16 and 17 of Table 2.

Another subset of the compounds of Formula I include compounds of Formula I(d):

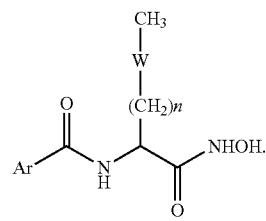  I(d)

When the compound has a structure of Formula I(d) then the compound is not a compound set forth in Table 1(b):

TABLE 1 (b)

| Structure | Name | Reference(s) |
|---|---|---|
| 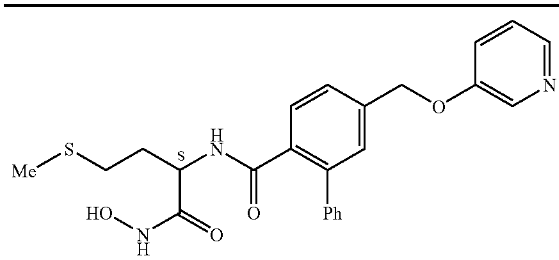 | (S)-N-[1-[(hydroxyamino)carbonyl]-3-(methylthio)propyl]-5-[(3-pyridinyloxy)methyl]-[1,1'-Biphenyl]-2-carboxamide CAS Registry No. 191101-76-5 | WO 97/17070 U.S. 2002193596 |
| 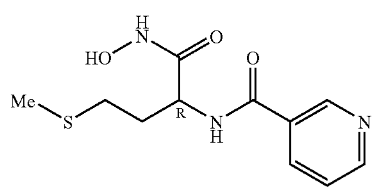 | N-[(1R)-1-[(hydroxyamino)carbonyl]-3-(methylthio)propyl]-3-Pyridinecarboxamide CAS Registry No. 220390-32-9 | WO 99/06340 |
| 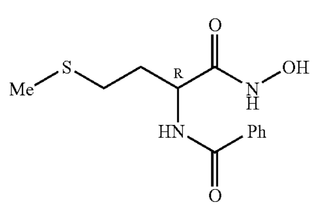 | N-[(1R)-1-[(hydroxyamino)carbonyl]-3-(methylthio)propyl]-Benzamide CAS Registry No. 220390-33-0 | WO 99/06340 |
| 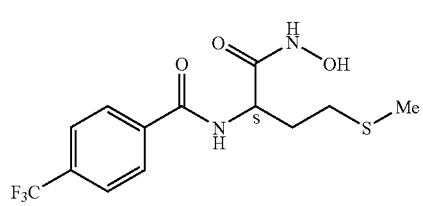 | N-[(1S)-1-[(hydroxyamino)carbonyl]-3-(methylthio)propyl]-4-(trifluoromethyl)-Benzamide or N-[4-(trifluoromethyl)benzoyl]-L-methionine hydroxamic acid CAS Registry No. 373639-72-6 | Bioorganic Chemistry (2001), 29(4), 211-222 WO 2005/037257 |

TABLE 1 (b)-continued

| Structure | Name | Reference(s) |
|---|---|---|
| HO—NH—C(=O)—CH(NH—C(=O)—Ph)—CH₂—CH₂—S—Me | N-[1-[(hydroxyamino)carbonyl]-3-(methylthio)propyl]-Benzamide CAS Registry No. 373639-76-0 | Bioorganic Chemistry (2001), 29(4), 211-222 |
| (1-naphthoyl)—NH—CH(C(=O)—NH—OH)—CH₂—CH₂—S—Me | N-[1-[(hydroxyamino)carbonyl]-3-(methylthio)propyl]-1-Naphthalenecarboxamide CAS Registry No. 373639-77-1 | Bioorganic Chemistry (2001), 29(4), 211-222 |
| (2-phenoxybenzoyl)—NH—CH(C(=O)—NH—OH)—CH₂—CH₂—S—Me | N-[1-[(hydroxyamino)carbonyl]-3-(methylthio)propyl]-2-phenoxy-Benzamide CAS Registry No. | Bioorganic Chemistry (2001), 29(4), 211-222 |

Although the first three compounds set forth in Table 1(b) are excluded as compounds claimed in the present invention, they are expected to have antibacterial activity and, accordingly, the use of these compounds as antibacterial agents falls within the scope of the present invention.

In the compounds of Formula I(d) W may be S, SO or SO₂; n is 1 or 2; and Ar may be an optionally substituted aryl or heteroaryl. These compounds also include compounds with the following stereochemistry:

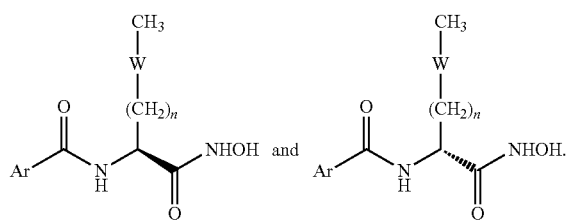

Although Ar includes any optionally substituted aryl or heteroaryl, in one embodiment, Ar may also include the following substituted aryl compound.

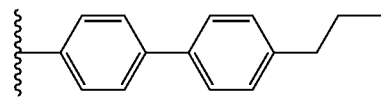

Particular embodiments of Formula I(d) also include compounds with the following substituents where:

W is S and n is 1;
W is S and n is 2;
W is SO₂ and n is 1; and
W is SO₂ and n is 2.

In some of these compounds when A is

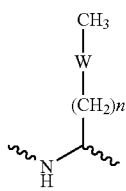

then W is not S.

Particular embodiments of Formula I(d) include compounds 26-29 of Table 2.

Another subset of the compounds of Formula I include compounds of Formula I(e):

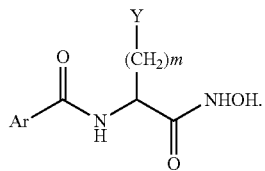

When the compound has a structure of Formula I(e) then the compound is not a compound set forth in Table 1(c):

Although the first four compounds set forth in Table 1(c) are excluded as compounds claimed in the present invention, they are expected to have antibacterial activity and, accordingly, the use of these compounds as antibacterial agents falls within the scope of the present invention.

In the compounds of Formula I(e) Y can be a heteroaryl; m is 0 or 1; and Ar can be an optionally substituted aryl or heteroaryl. In one embodiment, Y may be a 5-membered heteroaryl ring. Additionally, Y may be TABLE 1 (c)

| Structure | Name | Reference(s) |
|---|---|---|
|  | (R)-2-[[[2-(hydroxyamino)-1-(1H-imidazol-4-ylmethyl)-2-oxoethyl]amino]carbonyl]-Benzoic acid<br>CAS Registry No. 66695-61-2 | U.S. Pat. No. 4,077,998 |
|  | (alphaR)-N-hydroxy-alpha-[(3-pyridinylcarbonyl)amino]-3-Pyridinepropanamide<br>CAS Registry No. 220390-49-8 | WO 99/06340 |
|  | (alphaR)-alpha-(benzoylamino)-N-hydroxy-3-Pyridinepropanamide<br>CAS Registry No. 220390-50-1 | WO 99/06340 |
|  | (alphaS)-alpha-[(2-bromobenzoyl)amino]-N-hydroxy-1H-Indole-3-propanamide,<br>CAS Registry No. 556065-96-4 | Bioorganic & Medicinal Chemistry Letters (2003), 13(6), 1015-1018 |
|  | (alphaS)-alpha-[[(4'-ethyl[1,1'-biphenyl]-4-yl)carbonyl]amino]-N-hydroxy-1H-Imidazole-4-propanamide<br>CAS Registry No. 728868-34-6 | WO 2004/062601 |

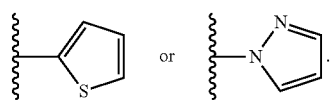 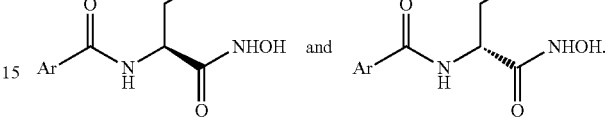

These compounds also include a compound with the following stereochemistry:

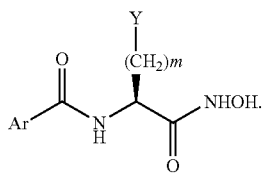

and Ar may be an optionally substituted aryl or heteroaryl. These compounds also include: compounds with the following stereochemistry:

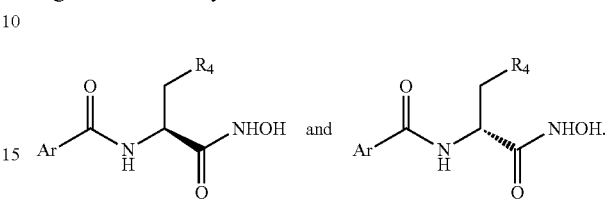

Although Ar includes any optionally substituted aryl or heteroaryl, in one embodiment, Ar may also include the following substituted aryl compound.

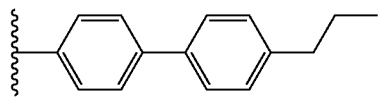

Particular compounds of Formula I(e) include compounds 30 and 31 of Table 2.

Another subset of the compounds of Formula I include compounds of Formula I(f):

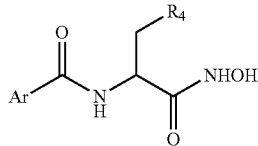

I (f)

In the compounds of Formula I(f) $R_4$ may be —$CH_2SCH_3$, —$CH_2SO_2CH_3$, —$SCH_3$, —$SO_2CH_3$, or Although Ar includes any optionally substituted aryl or heteroaryl, in one embodiment, Ar may also include the following substituted aryl compound.

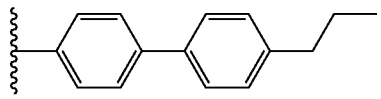

Particular embodiments of Formula I(f) include compounds 26-31 of Table 2.

Another subset of the compounds of Formula I include compounds of Formula I(g):

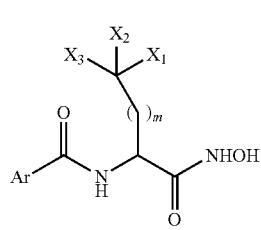

I (g)

When the compound has a structure of Formula I(g) then the compound is not a compound set forth in Table 1(d):

TABLE 1 (d)

| Structure | Name | Reference(s) |
| --- | --- | --- |
| 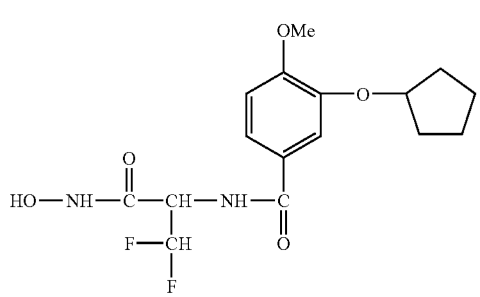 | 3-(cyclopentyloxy)-N-[2,2-difluoro-1-[(hydroxyamino)carbonyl]ethyl]-4-methoxy-Benzamide CAS Registry No. 188030-50-4 | WO 97/05105 |

TABLE 1 (d)-continued

| Structure | Name | Reference(s) |
|---|---|---|
| 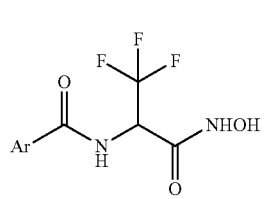 | 3-(cyclopentyloxy)-N-[1-(fluoromethyl)-2-(hydroxyamino)-2-oxoethyl]-4-methoxy-Benzamide CAS Registry No. 188030-45-7 | WO 97/05105 |
| 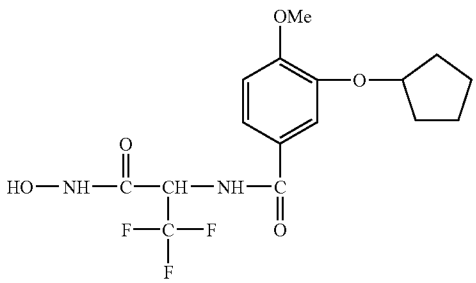 | 3-(cyclopentyloxy)-4-methoxy-N-[2,2,2-trifluoro-1-[(hydroxyamino)carbonyl]ethyl]-Benzamide CAS Registry No. 188030-26-4 | WO 97/05105 |

Although the compounds set forth in Table 1(d) are excluded as compounds claimed in the present invention, they are expected to have antibacterial activity and, accordingly, the use of these compounds as antibacterial agents falls within the scope of the present invention.

In the compounds of Formula I(g) $X_1$, $X_2$, and $X_3$ may each independently be H or F; and Ar may be an optionally substituted aryl or heteroaryl. Although Ar includes any optionally substituted aryl or heteroaryl, in one embodiment, Ar may also include the following substituted aryl compound.

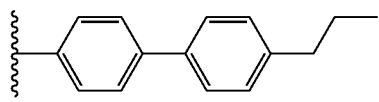

Additionally, Ar groups may be one of the following:

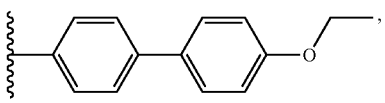

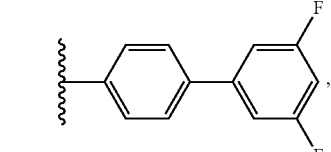

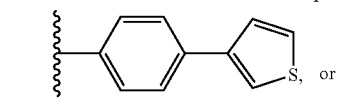

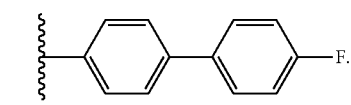

Another subset of the compounds of Formula I include compounds of Formula I(g)(i):

I(g)(i)

wherein Ar is an optionally substituted aryl or heteroaryl. Ar groups include, but are not limited to,

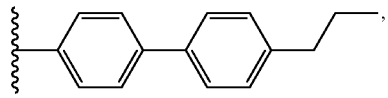

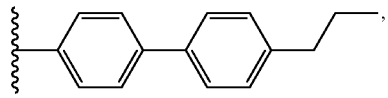

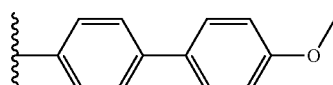

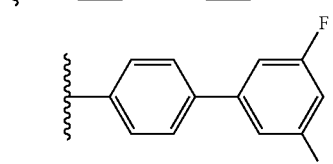

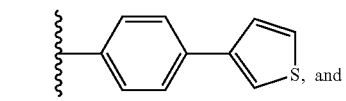

-continued

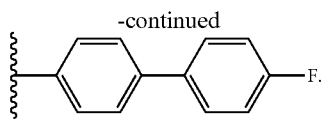

Particular embodiments of Formula I(g) include compounds 21-25 of Table 2.

Another set of the compounds of include compounds of Formula II

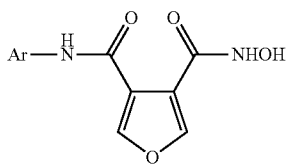

Although Ar includes any optionally substituted aryl, in one embodiment, Ar may also include the following substituted aryl compound, such as in compound 32 of Table 2.

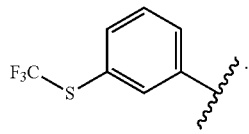

In another aspect, provided herein are pharmaceutical compositions comprising a pharmaceutically acceptable carrier and a therapeutically effective amount of the compounds defined herein. The pharmaceutical compositions can further comprise one or more additional antibacterial agents, one of which may be active against Gram positive bacteria. One of which may also be active against Gram negative bacteria.

In one of its method aspects, provided herein is a method for the treatment of a microbial infection in a mammal comprising administering to the mammal a therapeutically effective amount of a compound provided herein. The compound can be administered to the mammal orally, parenterally, transdermally, topically, rectally, or intranasally in a pharmaceutical composition.

In another of its method aspects, provided herein is a method for the treatment of a microbial infection in a mammal comprising administering to the mammal a pharmaceutical composition comprising a therapeutically effective amount of a compound provided herein. The pharmaceutical composition may further one or more additional antibacterial agents, one of which may be active against Gram positive bacteria. One of which may also be active against Gram negative bacteria.

The pharmaceutical composition may be administered to the mammal orally, parenterally, transdermally, topically, rectally, or intranasally.

In a preferred embodiment, the infection is a Gram negative infection. In an additional embodiment, the infection may be a Gram positive infection.

In yet another aspect, provided herein are novel intermediates and processes for preparing the compounds.

As described above, provided herein are N-hydroxyamide derivatives which inhibit LpxC and as a result, have gram negative antibacterial activity. Other N-hydroxyamide derivatives that also inhibit LpxC were described in U.S. Application Ser. Nos. 60/394,862, filed Jul. 12, 2002, and 10/617,616, filed Jul. 11, 2003, the entirety of all of which are hereby expressly incorporated by reference in their entirety. However, the following terms will first be defined.

DEFINITIONS

Unless otherwise stated, the following terms used in the specification and claims have the meanings given below:

"Halo" means fluoro, chloro, bromo, or iodo.

"Nitro" means the group —$NO_2$.

"Hydroxy" means the group —OH.

"Alkyl" means a linear saturated monovalent hydrocarbon radical of one to eight carbon atoms or a branched saturated monovalent hydrocarbon radical of three to eight carbon atoms. Examples of alkyl groups include, but are not limited to, groups such as methyl, ethyl, n-propyl, isopropyl, n-butyl, isobutyl, sec-butyl, t-butyl, n-pentyl, and the like.

"Alkylene" means a linear divalent hydrocarbon group of one to eight carbon atoms or a branched divalent hydrocarbon group of three to eight carbon atoms. Examples of alkylene groups include, but are not limited to, methylene, ethylene, 2-methylpropylene, and the like.

"Alkenyl" means a linear unsaturated monovalent hydrocarbon radical of two to eight carbon atoms or a branched monovalent hydrocarbon radical of three to eight carbon atoms containing at least one double bond, (—C═C—). Examples of alkenyl groups include, but are not limited to, allyl, vinyl, 2-butenyl, and the like.

"Alkynyl" means a linear monovalent hydrocarbon radical of two to eight carbon atoms or a branched monovalent hydrocarbon radical of three to eight carbon atoms containing at least one triple bond, (—C≡C—). Examples of alkynyl groups include, but are not limited to, ethynyl, propynyl, 2-butynyl, and the like.

"Alkynylene" means a linear divalent hydrocarbon radical of two to eight carbon atoms or a branched monovalent hydrocarbon radical of three to eight carbon atoms containing at least one triple bond, (—C≡C—). Examples of alkynylene groups include, but are not limited to, ethynylene, propynylene, and the like.

"Alkylsilylalkynyl" means the group (alkyl)3Si-alkynylene—where alkyl and alkynylene are as defined above.

"Haloalkyl" means an alkyl substituted with one or more, preferably one to 6, of the same or different halo atoms. Examples of haloalkyl groups include, for example, trifluoromethyl, 3-fluoropropyl, 2,2-dichloroethyl, and the like.

"Hydroxyalkyl" refers to an alkyl substituted with one or more —OH groups provided that if two hydroxy groups are present they are not both on the same carbon atom. Examples of hydroxyalkyl groups include, for example, hydroxymethyl, 2-hydroxyethyl, 2-hydroxypropyl, and the like.

"Alkylthio" refers to the group "alkyl-S—" where alkyl is as defined above and which includes, by way of example, methylthio, butylthio, and the like.

"Alkylsulfinyl" refers to the group "alkyl-S(O)—" where alkyl is as defined above and which includes, by way of example, methyl-S(O)—, butyl-S(O)—, and the like.

"Alkylsulfonyl" refers to the group "alkyl-S(O)$_2$—" where alkyl is as defined above and which includes, by way of example, methyl-S(O)$_2$—, butyl-S(O)$_2$—, and the like.

"Alkoxy" refers to the group "alkyl-O—", wherein alkyl is as defined above, and which includes, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkoxyalkyl" refers to the group "-alkylene-O-alkyl" where alkylene and alkyl are as defined herein and which includes, by way of example, 2-propoxyethylene, 3-methoxybutylene, and the like.

"Alkenoxy" refers to the group "alkenyl-O—" where alkenyl is as defined herein and which includes, by way of example, allyloxy, vinyloxy, 2-butenyloxy, and the like.

"Alkenoxyalkyl" refers to the group "alkenyl-O-alkylene" where alkenyl and alkylene are as defined herein and which includes, by way of example, 3-allyloxy-propylene, 2-(2-propenyloxy)ethylene, and the like.

"Alkynyloxy" refers to the group "alkynyl-O—" where alkynyl is as defined herein and which includes, by way of example, propargyloxy and the like.

"Arylalkoxyalkyl" refers to the group "aryl-alkoxy-alkylene-" where aryl, alkoxy and alkylene are as defined herein.

"Haloalkoxy" refers to the group "haloalkyl-O—" where haloalkyl is as defined herein and which includes, by way of example, trifluoromethoxy, 2,2-dichloroethoxy, and the like.

"Haloalkylthio" refers to the group "haloalkyl-S—" where haloalkyl is as defined herein which includes, by way of example, trifluoromethylthio, 2,2-difluoropropylthio, 3-chloropropylthio, and the like.

"Haloalkyl-sulfinyl" refers to the group "haloalkyl-S(O)—" where haloalkyl is as defined herein and which includes, by way of example, trifluoromethanesulfinyl, 2,2-dichloroethanesulfinyl, and the like.

"Haloalkyl-sulfonyl" refers to the group "haloalkyl-S(O)$_2$—" where haloalkyl is as defined herein and which includes, by way of example, trifluoromethanesulfonyl, 2,2-dichloroethanesulfonyl, and the like.

"Amino" refers to the group "—NR$_a$R$_b$" wherein R$_a$ and R$_b$ are independently H, alkyl, haloalkyl, alkenyl, cycloalkyl, aryl, substituted aryl, heteroaryl, or substituted heteroaryl where each of alkyl, haloalkyl, alkenyl, cycloalkyl, aryl, substituted aryl, heteroaryl, and substituted heteroaryl are as defined herein.

"Carbonyl" means the group "—C(O)—."

"Carboxyl" refers to —COOR where R is hydrogen, alkyl, aryl, heteroaryl and heterocycle or salts thereof.

"Carboxylamide" refers to —C(O)NR$_a$R$_b$" wherein R$_a$ and R$_b$ are independently H, alkyl, haloalkyl, alkenyl, cycloalkyl, aryl, substituted aryl, heteroaryl, or substituted heteroaryl where each of alkyl, haloalkyl, alkenyl, cycloalkyl, aryl, substituted aryl, heteroaryl, and substituted heteroaryl are as defined herein.

"Acyloxy" means the group —C(O)R' wherein R' is alkyl, alkenyl, alkynyl, aryl, substituted aryl, heteroaryl, or substituted heteroaryl where alkyl, alkenyl, alkynyl, aryl, substituted aryl, heteroaryl, or substituted heteroaryl are as defined herein.

"Cycloalkyl" means a cyclic saturated hydrocarbon group of 3 to 8 ring atoms, where one or two of C atoms are optionally replaced by a carbonyl group. The cycloalkyl group may be optionally substituted with one, two, or three substituents, preferably alkyl, alkenyl, halo, hydroxyl, cyano, nitro, alkoxy, haloalkyl, alkenyl, and alkenoxy as these terms are defined herein. Representative examples include, but are not limited to, cyclopropyl, cyclohexyl, cyclopentyl, and the like.

"Cycloalkylalkyl" means a group —R$_c$R$_d$ where R$_c$ is an alkylene group and R$_d$ is a cycloalkyl group, as defined above. Examples include, but are not limited to, cyclopropylmethylene, cyclohexylethylene, and the like.

"Aryl" means a monovalent monocyclic or bicyclic aromatic carbocyclic group of 6 to 14 ring atoms. Examples include, but are not limited to, phenyl, naphthyl, and anthryl. The aryl ring may be optionally fused to a 5-, 6-, or 7-membered monocyclic non-aromatic ring optionally containing 1 or 2 heteroatoms independently selected from oxygen, nitrogen, or sulfur, the remaining ring atoms being C where one or two C atoms are optionally replaced by a carbonyl. Such fused ring systems are referred to herein as "cyclic moiety containing a total of 4, 5, 6, or 7 ring atoms." Representative aryl groups with fused rings include, but are not limited to, 2,5-dihydro-benzo[b]oxepine, 2,3-dihydrobenzo[1,4]dioxane, chroman, isochroman, 2,3-dihydrobenzofuran, 1,3-dihydroisobenzofuran, benzo[1,3]dioxole, 1,2,3,4-tetrahydroisoquinoline, 1,2,3,4-tetrahydroquinoline, 2,3-dihydro-1H-indole, 2,3-dihydro1H-isoindole, benzimidazole-2-one, 2-H-benzoxazol-2-one, and the like.

"Substituted aryl" means an aryl ring substituted with one or more substituents, preferably one to three substituents selected from the group consisting of alkyl, alkenyl, alkynyl, halo, alkoxy, acyloxy, amino, hydroxyl, carboxy, cyano, nitro, and alkylthio as these terms are defined herein. The aryl ring may be optionally fused to a 5-, 6-, or 7-membered monocyclic non-aromatic ring optionally containing 1 or 2 heteroatoms independently selected from oxygen, nitrogen, or sulfur, the remaining ring atoms being C where one or two C atoms are optionally replaced by a carbonyl.

"Heteroaryl" means a monovalent monocyclic or bicyclic aromatic radical of 5 to 10 ring atoms containing one, two, or three ring heteroatoms selected from N, O, or S, the remaining ring atoms being C. Representative examples include, but are not limited to, thienyl, benzothienyl, pyridyl, pyrazinyl, pyrimidinyl, pyridazinyl, quinolinyl, quinoxalinyl, imidazolyl, furanyl, benzofuranyl, thiazolyl, isoxazolyl, benzisoxazolyl, benzimidazolyl, triazolyl, pyrazolyl, pyrrolyl, indolyl, 2-pyridonyl, 4-pyridonyl, N-alkyl-2-pyridonyl, pyrazinonyl, pyridazinonyl, pyrimidinonyl, oxazolonyl, and the like.

"Substituted heteroaryl" means a heteroaryl ring substituted with one or more substituents, preferably one to three substituents selected from the group consisting of alkyl, alkenyl, alkynyl, halo, alkoxy, acyloxy, amino, hydroxyl, carboxy, cyano, nitro, and alkylthio as these terms are defined herein.

"Aryloxy" means a group "—O—Ar" where Ar is an aryl group or substituted aryl group as these terms are defined herein. Examples include, but are not limited to, benzyloxy, 4-trifluoromethyl-benzyloxy, and the like.

"Arylalkoxy" means a group "—O-alkylene-Ar" where Ar is an aryl group or substituted aryl group as defined herein and alkylene is as also defined herein. Examples include, but are not limited to, 2-(phenyl)ethoxy, 3-(phenyl)propoxy, and the like.

"Arylalkoxyalkyl" means a group "-alkylene-O-alkylene-Ar" where Ar is an aryl group or substituted aryl group as defined herein and each alkylene is independently selected from the other, wherein alkylene is as also defined herein. Examples include, but are not limited to, benzyloxy-propylene, benzyloxy-ethylene, and the like.

"Aminocarboxyalkyl" means a group "—R$_c$C(O)NR$_a$R$_b$" where R$_c$ is an alkylene group as defined herein and R$_a$ and R$_b$ are as defined above.

"Haloarylalkyl" means the group "aryl-alkylene-" having 1 to 6 halo substituents on either the aryl and/or the alkylene groups where aryl and alkylene are as defined herein.

"Haloarylalkenyl" means the group "aryl-alkenylene-" having 1 to 6 halo substituents on either the aryl and/or the alkenylene groups where aryl and alkenylene are as defined herein.

"Haloarylalkynyl" means the group "aryl-alkynylene-" having 1 to 6 halo substituents on either the aryl and/or the alkynylene groups where aryl and alknyylene are as defined herein.

"Heterocycle" or "heterocyclic" refers to a saturated or unsaturated group having a single ring or multiple condensed rings, from 1 to 10 carbon atoms and from 1 to 4 heteroatoms selected from the group consisting of nitrogen, sulfur, or oxygen within the ring, wherein, in fused ring systems one or more of the rings can be aryl or heteroaryl as defined herein. Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

Heterocycles may be optionally substituted with from one to three substituents selected from the group consisting of alkyl, alkenyl, alkynyl, halo, alkoxy, acyloxy, amino, hydroxyl, carboxy, cyano, nitro, and alkylthio as these terms are defined herein.

"Optional" or "optionally" means that the subsequently described event or circumstance may, but need not, occur, and that the description includes instances where the event or circumstance occurs and instances in which it does not. For example, "aryl group optionally mono- or di-substituted with an alkyl group" means that the alkyl may but need not be present, and the description includes situations where the aryl group is mono- or disubstituted with an alkyl group and situations where the aryl group is not substituted with the alkyl group.

A "pharmaceutically acceptable carrier" means a carrier that is useful in preparing a pharmaceutical composition that is generally safe, non-toxic and neither biologically nor otherwise undesirable, and includes a carrier that is acceptable for veterinary use as well as human pharmaceutical use. "A pharmaceutically acceptable carrier" as used in the specification and claims include both one and more than one such carrier.

A "pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

A "salt" is refers to all salt forms of a compound, including salts suitable for use in industrial processes, such as the preparation of the compound, and pharmaceutically acceptable salts.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

A "therapeutically effective amount" means the amount of a compound or mixture of compounds that, when administered to a mammal for treating a disease, is sufficient to effect such treatment for the disease. The "therapeutically effective amount" will vary depending on the compound, the disease and its severity and the age, weight, etc., of the mammal to be treated.

"Pro-drugs" mean any compound which releases an active parent drug according to a compound provided herein in vivo when such prodrug is administered to a mammalian subject. Prodrugs of a compound provided herein are prepared by modifying functional groups present in a compound provided herein in such a way that the modifications may be cleaved in vivo to release the parent compound. Prodrugs include compounds provided herein wherein a hydroxy, sulfhydryl or amino group in the compound is bonded to any group that may be cleaved in vivo to regenerate the free hydroxyl, amino, or sulfhydryl group, respectively. Examples of prodrugs include, but are not limited to $C_1$-$C_{10}$ esters (e.g., acetate, formate, and benzoate derivatives), carbamates (e.g., N,N-alkylaminocarbonyl) of hydroxy functional groups in compounds provided herein, and the like.

The term "tautomers" refers to herein as a constitutional isomer in which migration of a hydrogen atom results in two ore more structures. As an example of one potential tautomer, the N-hydroxyamide may tautomerize to form a 1,2-dihydroxyimine.

The term "mammal" refers to all mammals including humans, livestock, and companion animals.

The compounds provided herein are generally named according to the IUPAC or CAS nomenclature system. Abbreviations which are well known to one of ordinary skill in the art may be used (e.g. "Ph" for phenyl, "Me" for methyl, "Et" for ethyl, "h" for hour or hours and "rt" for room temperature).

Generally, reference to a certain element such as hydrogen or H is meant to include all isotopes of that element. For example, if an R group is defined to include hydrogen or H, it also includes deuterium and tritium.

General Synthetic Schemes

Compounds provided herein can be made by the methods depicted in the reaction schemes shown below.

The starting materials and reagents used in preparing these compounds are either available from commercial suppliers such as Toronto Research Chemicals (North York, ON Canada), Aldrich Chemical Co. (Milwaukee, Wis., USA), Bachem (Torrance, Calif., USA), Matrix Scientific (Columbia, S.C., USA), Emka-Chemie, or Sigma (St. Louis, Mo., USA) or are prepared by methods known to those skilled in the art following procedures set forth in references such as Fieser and Fieser's Reagents for Organic Synthesis, Volumes 1-15 (John Wiley and Sons, 1991), Rodd's Chemistry of Carbon Compounds, Volumes 1-5 and Supplementals (Elsevier Science Publishers, 1989), Organic Reactions, Volumes 1-40 (John Wiley and Sons, 1991), March's Advanced Organic Chemistry, (John Wiley and Sons, 4th Edition), and Larock's Comprehensive Organic Transformations (VCH Publishers Inc., 1989). These schemes are merely illustrative of some methods by which the compounds provided herein can be synthesized, and various modifications to these schemes can be made and will be suggested to one skilled in the art having referred to this disclosure.

As it will be apparent to those skilled in the art, conventional protecting groups may prevent certain functional groups from undergoing undesired reactions. Suitable protecting groups for various functional groups, as well as suitable conditions for protecting and deprotecting particular function groups are well known in the art. For example, numerous protecting groups are described in T. W. Greene and G. M. Wuts, Protecting Groups in Organic Synthesis, Second Edition, Wiley, New York, 1991, and references cited therein.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

The compounds provided herein will typically contain one or more chiral centers. Accordingly, if desired, such compounds can be prepared or isolated as pure stereoisomers. All such stereoisomers (and enriched mixtures) are included within the scope provided herein, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

General Synthetic Description

Compounds provided herein can be prepared by the methods as described below in a way of example.

Compounds of Formula I(a) can be prepared as illustrated in Schemes 1 and 2.

Scheme 1:

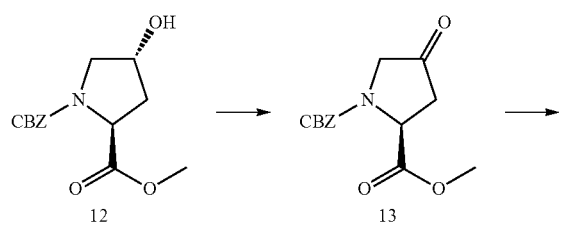

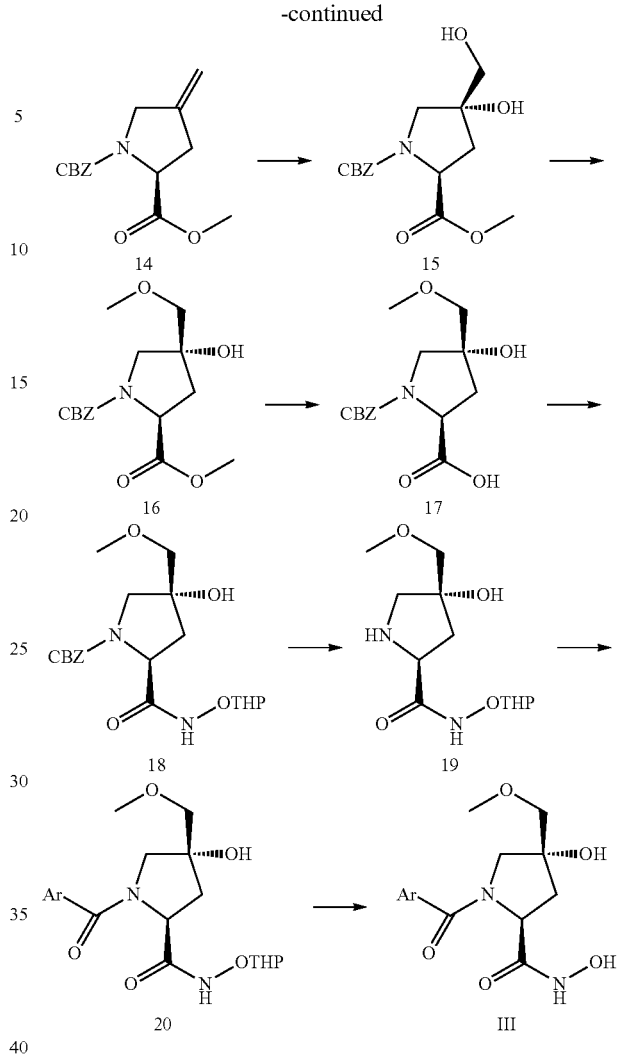

The conventional oxidation of the hydroxyl group of 12 (e.g., Swern oxidation, pyridinium dichromate or dess-Martin oxidation conditions) provides N-protected 4-oxoproline methyl ester, 13 (Scheme 1). Reaction of 13 with dibromomethane, Zn and bis(cyclopentadienyl)zirconium dichloride in organic solvent, for example, THF provided the alkene derivative 14. Osmylation or catalytic asymmetric dihydroxylation in an organic solvent at 0° C. to 40° C. furnished the di-hydroxy 15.

The primary alcohol in 15 is selectively O-methylated with an alkylating agent in the presence of a base to provide the alkylated product 16 (Scheme 1). Suitable methylating agents include trimethyloxonium tetrafluoroborate and the like. The alkylation is conducted in an inert organic solvent such as, for example, N,N-dimethylformamide, acetonitrile, dichloromethane, and N-methylpyridone. Suitable bases include, 2,6-di-tert-butyl-4-methylpyridine, triethylamine and the like. The reaction is typically conducted at room temperature for about 2 to about 16 hours.

The methyl ester 16 is then treated with aqueous inorganic base in polar solvent to hydrolyze the methyl ester protecting group and then the carboxylic acid is coupled with an O-protected hydroxyl amine to provide amide 18. A suitable base includes lithium hydroxide, sodium hydroxide and suitable organic solvents include methanol, tetrahydrofuran and dioxane. The acid is coupled with the O-protected hydroxylamine using a coupling reagent such as HATU in an organic base in an inert organic solvent. Suitable organic bases include DIEA, TEA, pyridine, and N-methyl morpholine, and suitable inert organic solvents include N,N-dimethylformamide, acetonitrile, dichloromethane, and alike.

The O-protected amide 18 is then hydrogenated to remove the N-protecting group to provide an amine 19 (Scheme 1). The hydrogenation is carried out in a polar organic solvent such as ethanol or methanol. The reduction is carried out in the presence of a palladium catalyst under hydrogen atmosphere. The reduction may conveniently be carried out at ambient temperatures in about 2 minutes to 24 hours.

Amidation of the amide 19 with an optionally substituted aromatic acid, preferably in an inert organic solvent, in the presence of a coupling reagent and an organic base to provided an amide 20 (Scheme 1). This reaction can be performed with any number of known coupling reagents, such as HATU, HOBT, carbodiimides, DPPA, and the like. Suitable organic bases include DIEA, TEA, pyridine, N-methyl morpholine, and the like. Suitable inert organic solvents which can be used include, for example, N,N-dimethylformamide, acetonitrile, dichloromethane, and the like. The reaction is continued until completion, which typically occurs in from about 2 to 12 hours.

The amide 20 is then converted to the N-hydroxyamide derivative of Formula I(a) by treatment with acid in a organic solvent such as dichloroethane, methylene chloride and the like. The reaction is carried out at 0° C. to ambient temperature for about 1 to 6 hours.

Scheme 2:

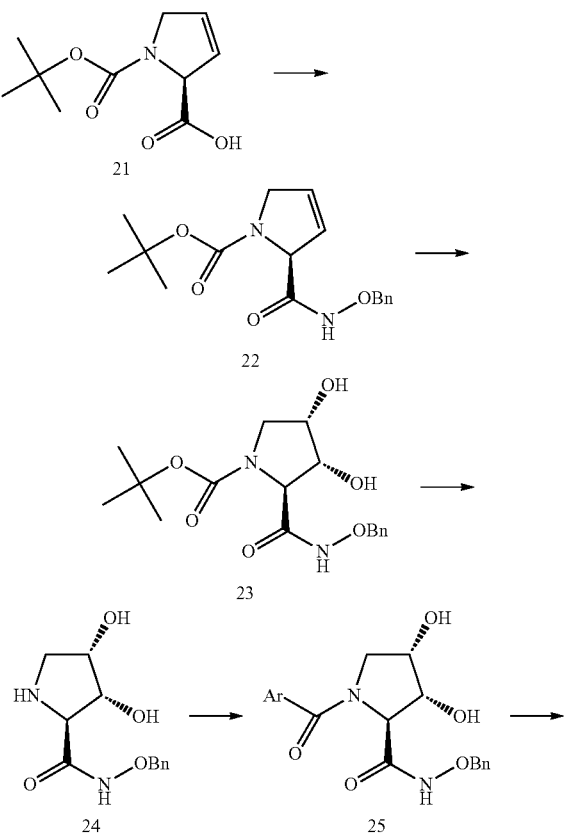

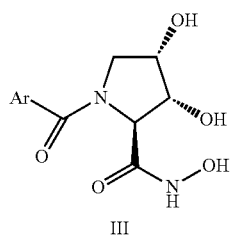

III

The Boc-protected 21 is coupled with O-benzyl hydroxylamine under reactive conditions, preferably in an inert organic solvent, in the presence of a coupling reagent and an organic base to provide a benzyloxyamide 22 (Scheme 2). This reaction can be performed with any number of known coupling reagents, such as HATU, HOBT, carbodiimides, DPPA, and the like. Suitable organic bases include DIEA, TEA, pyridine, N-methyl morpholine, and the like. Suitable inert organic solvents which can be used include, for example, N,N-dimethylformamide, acetonitrile, dichloromethane, and the like. This reaction is typically conducted at temperatures in the range of about 0° C. to 25° C. The reaction is continued until completion, which typically occurs in from about 2 to 24 hours.

The hydroxylated 23 can be prepared by methods well known in the art (Scheme 2). Suitable hydroxylating agents for converting the alkene to the diol include $OsO_4$ and 4-methylmorpholine-N-oxide in t-butyl alcohol and Sharpless reagents. The reaction is generally carried out from about 12 to 24 hours.

The benzyloxyamide is then reacted with an acid to remove the t-butoxycarbonyl protecting group (Scheme 2). Removal of the protecting group may be carried out with acids, such as a trifluoroacetic acid (TFA), hydrochloric acid, p-toluenesulfonic acid, and the like, in an inert organic solvent such as dichloromethane, dioxane, THF, and the like. The removal is typically conducted at low temperatures, e.g., 0° C., and then gradually allowed to warm to room temperature to provide the benzyloxyamide acid salt.

Amidation of the benzyloxyamide acid salt is then conducted with an optionally substituted biphenyl acid under reactive conditions, preferably in an inert organic solvent, in the presence of a coupling reagent and an organic base to provide an amide (25). This reaction can be performed with any number of known coupling reagents, such as HATU, HOBT, carbodiimides, DPPA, and the like. Suitable organic bases include DIEA, TEA, pyridine, N-methylmorpholine, and the like. Suitable inert organic solvents which can be used include, for example, N,N-dimethylformamide, acetonitrile, dichloromethane, and the like. This reaction is typically conducted using an excess of benzyloxyamide to benzoic acid at temperatures in the range of about 0° C. to about 50° C. The reaction is continued until completion, which typically occurs in from about 2 to 24 hours.

25 is then converted to the N-hydroxyamide derivative of Formula I(a) by hydrogenation to remove the benzyloxy protecting group (OBn (Scheme 2). Deprotection is carried out in a polar organic solvent such as ethanol or methanol. The hydrogenation is carried out at in the presence of a palladium (II) catalyst or palladium on carbon under hydrogen atmosphere. The hydrogenation conveniently may be carried at ambient temperatures in about 1 to 24 hours.

Compounds of Formula I(a)(i) can be prepared by methods known in the art of organic chemistry. Representative synthetic procedures for preparing compounds provided herein are illustrated and described in detail below.

Scheme 3:

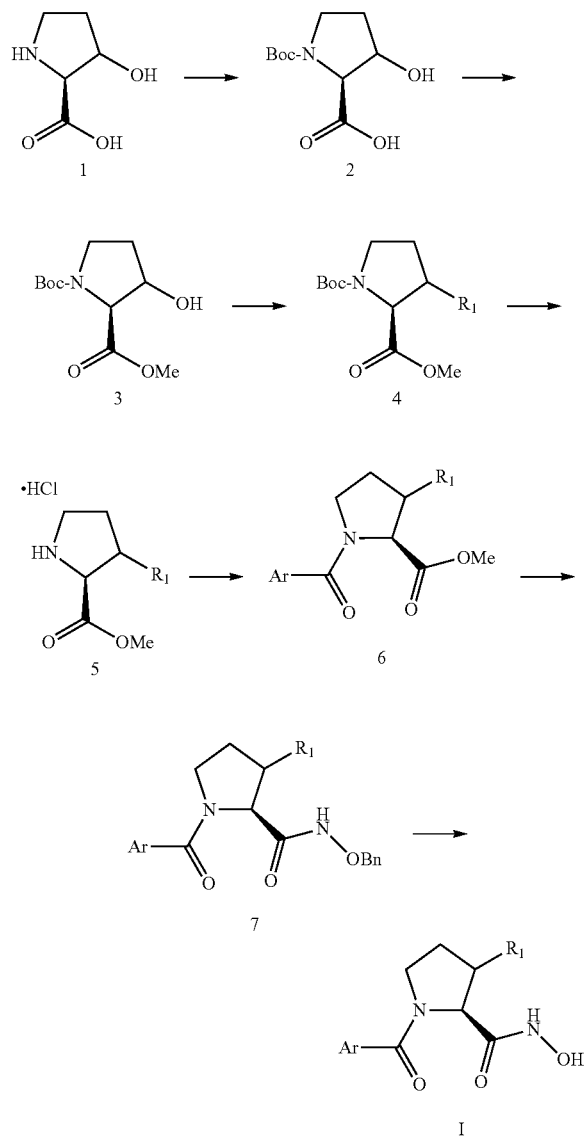

As shown in Scheme 3, 3-hydroxyproline is reacted with di-tert-butyl dicarbonate (Boc$_2$O) in the presence of an organic or inorganic base to provide a Boc-protected amino acid (2). The transformation is typically carried out in an inert organic solvent, such as dioxane, tetrahydrofuran (THF), and the like, at low temperatures, e.g., from 0 to 25° C., such as 0° C. Suitable organic bases include triethylamine (TEA), pyridine, and suitable inorganic bases include sodium bicarbonate, sodium carbonate, sodium hydroxide and the like.

The methyl ester of Boc-protected hydroxyproline carboxylic acid (3) can be generated by alkylation with a suitable methylating reagent such as trimethylsilyl-diazomethane. Transformation is typically carried out at low temperatures, e.g., 0° C., and after the addition, the reaction is allowed to warm to ambient temperature, e.g., about 25° C.

3 can be converted to a variety of other proline derivatives. For example, inversion of the 3-R-hydroxy substituent to the 3-S-hydroxy substituent in 3 can be accomplished by reaction with p-nitrobenzoic acid, phosphine and diisopropyl azodicarboxylate (DIAD) in a suitable solvent such as tetrahydrofuran, dioxane, and alike followed by deacylation with a suitable alkaline reagent such as LiOH in MeOH.

Reaction of 3-mesylate derivative of 3 (4: $R_1$=OMs) made e.g., by reacting 3 with mesylchloride (MsCl) and TEA) with sodium azide in methanol affords respective 3-azido derivatives (4: $R_1$=$N_3$) that can be further elaborated into 3-amino compounds ($R_1$=$NH_2$). This transformation cab be optionally performed in the presence of a suitable crown ether, e.g., 15-crown-5.

The N-protected 3-hydroxyproline methyl ester, 3, can be used to prepare a variety of further derivatives. For example, reaction with fluorinated reagents (e.g., dimethoxydimethylaminosulfurtrifluoride) followed by deprotection provides for 3-fluoroproline methyl ester (4: $R_1$=F). Alternatively, alkylation of the hydroxyl group followed by nitrogen deprotection yields the 3-alkoxyproline methyl ester.

The substituted proline methyl ester 4 is then treated with an acid to remove the t-butoxycarbonyl protecting group (Boc) and produce the salt 5. Removal of the protecting group may be carried out with acids, such as a trifluoroacetic acid (TFA), hydrochloric acid, p-toluenesulfonic acid, and alike, in an inert organic solvent such as dichloromethane, dioxane, THF, and the like. The deprotection is typically conducted at low to ambient temperatures (e.g., 0° C.—r.t.).

The salt 5 is then condensed with an optionally substituted aromatic carboxylic acids under reactive conditions, preferably in an inert organic solvent, in presence of a coupling reagent and an organic base to provide an amide (6) (Scheme 3). Wide range of aromatic acids can be employed, e.g. biaryl carboxylic acid, or substituted biaryl carboxylic acid, etc. This reaction can be performed with any number of known coupling reagents, such as O-(7-azabenzotriazol-1-yl)-N,N,N',N'-tetramethyluronium hexafluorophosphate (HATU), 1-hydroxybenzotriazole hydrate (HOBT), carbodiimides, diphenylphosphoryl azide (DPPA), and alike. Suitable organic bases include diisopropyethylamine (DIEA), TEA, pyridine, N-methyl morpholine, and alike. Suitable inert organic solvents which can be used include, for example, N,N-dimethylformamide, acetonitrile, dichloromethane, and alike. This reaction is typically carried out at temperatures in the range of about 0° C. to about 50° C. The reaction is continued until completion, which typically occurs in from about 2 to 24 hours.

(6) is then converted to the N-benzyloxyamide derivative (7) by treatment with O-benzyl hydroxylamine and trimethyl aluminium in a non-polar organic solvent such as toluene, methylene chloride and the like (Scheme 3). The reaction is carried out at ambient temperature to 80° C. for about 2 to 24 hours.

(7) is then converted to the N-hydroxyamide derivative of Formula I(a)(i) by hydrogenation to remove the benzyloxy protecting group (OBz) (Scheme 3). Deprotection is carried out in a polar organic solvent such as methanol. The hydrogenation is carried out at in the presence of a palladium (II) catalyst or palladium on carbon under hydrogen atmosphere. The hydrogenation conveniently may be carried at ambient temperatures in about 1 hour to 16 hours.

Alternatively, methyl ester 6 can be directly converted into the hydroxamate 7 with a hydroxylamine reagent, such as aqueous (aq). hydroxylamine, or methanolic hydroxylamine HCl with NaOMe (see Scheme 4 below). The reaction is carried out at ambient temperature for about 2 to 6 hours.

Scheme 4:
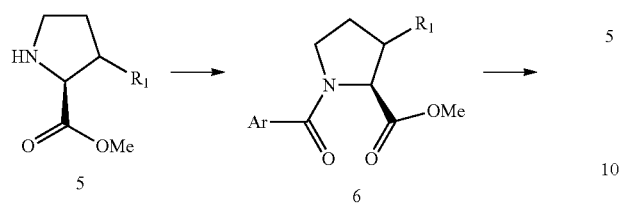
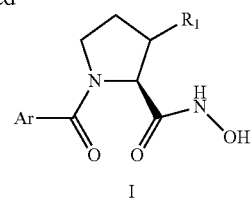
General syntheses of additional compounds of Formula I(a) is illustrated by Schemes 5-7 below.
Scheme 5:
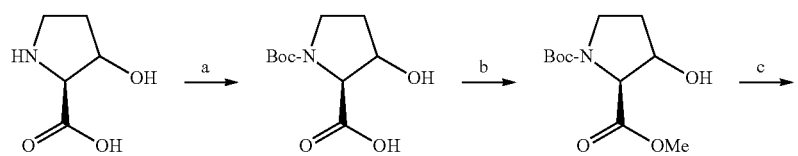
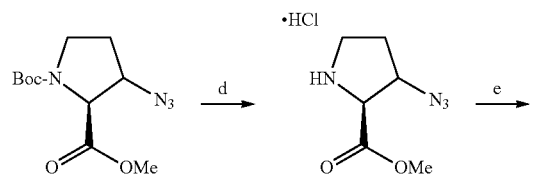
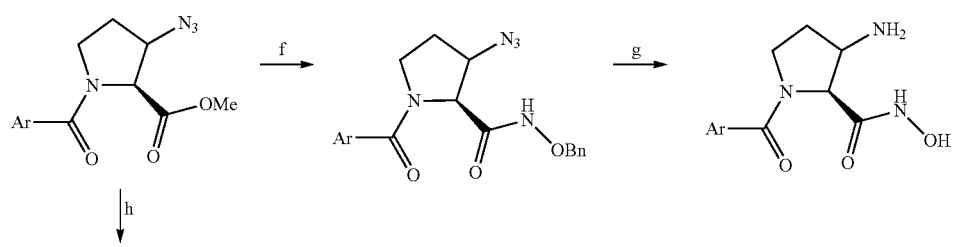
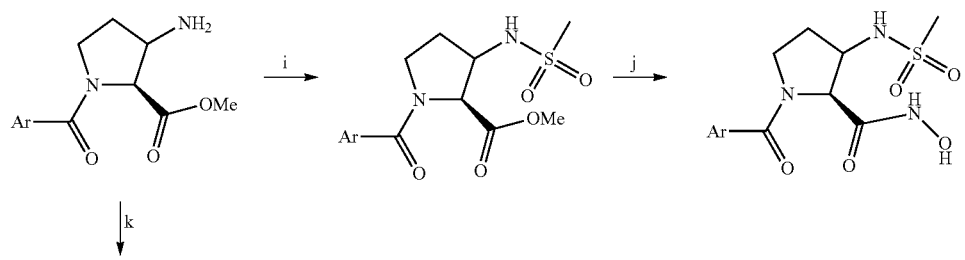
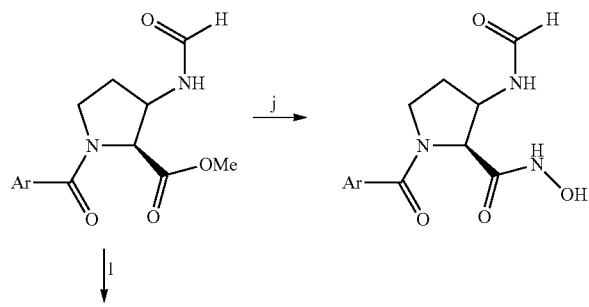

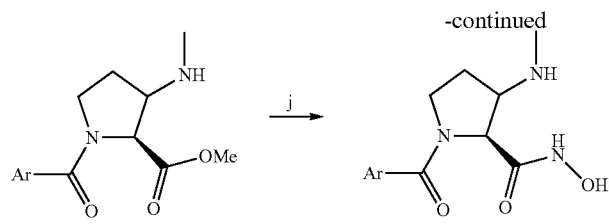

Scheme 5. Reagents and conditions.
(a) Protection (Boc₂O, base);
(b) Methyl ester formation ((trimethylsilyl)diazomethane (TMSCHN₂, MeOH);
(c) Azide substitution (DPPA, DIAD, triphenylphosphine (Ph₃P));
(d) Deprotection (4M HCl/Dioxane);
(e) Coupling (ArCOOH, HATU, DIEA, dimethylformamide (DMF));
(f) Amidation (Me₃Al, NH₂—OBn•HCl, Toluene)(Bn = benzyl);
(g) Hydroxamate formation (10% palladium on carbon (Pd/C), H₂, EtOH);
(h) Reduction (10% Pd/C, H₂, EtOH).
(i) Sulfonamidation (CH₃SO₂Cl, Pyridine);
(j) Hydroxamate formation (NH₂OH•HCl, NaOMe, MeOH).
(k) N-Formylation (HCOOH, Ac₂O);
(l) Reduction (BH₃•(CH₃)₂S, THF, MeOH).

3-hydroxyproline is reacted with di-tert-butyl dicarbonate (Boc₂O) in the presence of an organic or inorganic base to provide a Boc-protected amino acid. The transformation is typically carried out in an inert organic solvent, such as tetrahydrofuran (THF), at low temperatures, e.g., from 0 to 25° C., such as 0° C. Suitable organic base includes triethylamine (TEA), and a suitable inorganic base includes sodium bicarbonate.

The methyl ester of Boc-protected hydroxyproline carboxylic acid is generated by alkylation with a suitable methylating reagent such as trimethylsilyl-diazomethane. Transformation is typically carried out at low temperatures, e.g., 0° C., and after the addition, the reaction is allowed to warm to ambient temperature, e.g., about 25° C.

Inversion of the trans-hydroxy proline to cis-hydroxy proline is achieved by reaction with p-nitrobenzoic acid, phosphine and diisopropyl azodicarboxylate (DIAD) in a suitable solvent such as tetrahydrofuran, dioxane, and alike followed by deacylation with a suitable alkaline reagent such as LiOH in MeOH.

Reaction of cis-3-hydroxyproline methyl ester with DIAD, triphenylphosphine and diphenylphosphoryl azide provides the desired 3-azido proline methyl ester. Transformation is typically carried out at low temperatures, e.g., 0° C., and after the addition, the reaction is allowed to warm to ambient temperature, e.g., about 25° C.

The substituted proline methyl ester is then treated with hydrochloric acid in dioxane to remove the t-butoxycarbonyl protecting group (Boc) and produce the salt. The deprotection is typically conducted at ambient temperatures (e.g., 0° C.—r.t.) for 4-6 hours.

The HCl salt is then condensed with an optionally substituted aromatic carboxylic acids under coupling conditions utilizing O-(7-azabenzotriazol-1-yl)-N,N,N',N'-tetramethyluronium hexafluorophosphate (HATU), diisopropyethylamine (DIEA), in N,N-dimethylformamide (DMF). This reaction is typically carried out at temperatures in the range of about 0° C. to about 25° C. The reaction is continued until completion, which typically occurs in 24 hours.

The coupled product is then converted to the N-benzyloxyamide derivative by treatment with O-benzyl hydroxylamine and trimethyl aluminium in a non-polar organic solvent such as toluene. The reaction is carried out at ambient temperature to 80° C. for about 2 to 8 hours.

The N-benzyloxyamide derivative is then converted to the N-hydroxyamide derivative by hydrogenation to remove the benzyloxy protecting group (OBz). Reaction is carried out in a polar organic solvent such as ethanol. The hydrogenation is carried out at in the presence of a palladium (II) catalyst under hydrogen atmosphere. The hydrogenation conveniently may be carried at ambient temperatures in about 16 hours.

Alternately the azido functionality can be reduced to the amine in the presence of palladium on carbon. The reaction is carried out in a polar organic solvent such as ethanol. The hydrogentation is carried out at ambient temperatures in 2-3 hours.

The sulfonamide is generated in the presence of methanesulfonyl chloride using pyridine as the organic base. Reaction is typically carried out at temperatures in the range of about 0° C. to about 25° C. The reaction is completed in about 24 hours.

The sulfonamide bearing methyl ester can be directly converted into the hydroxamate with methanolic hydroxylamine HCl and NaOMe. The reaction is carried out at ambient temperature for about 2 to 6 hours.

The amine functionality can be transformed to the N-formylated methyl ester in the presence of a mixed anhydride, from formic acid and acetic anhydride. The reaction is carried out at room temperature and is typically completed in 4-24 hours.

The N-formylamine bearing methyl ester can be directly converted into the hydroxamate with methanolic hydroxylamine HCl and NaOMe. The reaction is carried out at ambient temperature for about 2 to 6 hours.

The reduction of the N-formylamine to N-methyl amine is accomplished in the presence of a borane-methylsulfide complex. The reaction is carried out in an inert inorganic solvent like THF. Methanol is added to complete the transformation which is typically carried out at ambient temperatures for about 12 hours.

The N-methylamine bearing methyl ester can be directly converted into the hydroxamate with methanolic hydroxylamine HCl and NaOMe. The reaction is carried out at ambient temperature for about 2 to 6 hours.

Scheme 6:

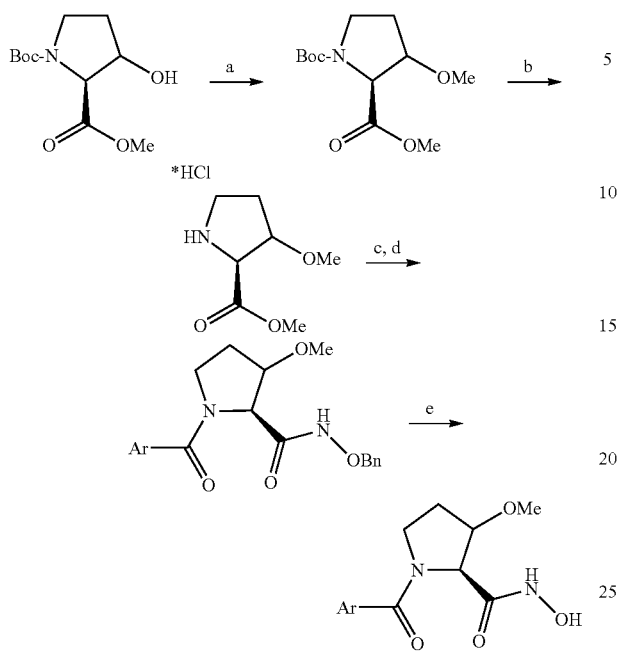

Scheme 6: Reagents and conditions.
(a) O-alkylation (MeI, Ag₂O);
(b) Deprotection (4M HCl/Dioxane);
(c) Coupling (ArCOOH, HATU, DIEA, DMF);
(d) Amidation (Me₃Al, NH₂—OBn•HCl, Toluene);
(e) Hydroxamate formation (10% Pd(OH)₂/C, EtOH).

The methoxy proline can be generated by alkylating the hydroxyproline in the presence of Methyl iodide and Silver (II) oxide. The reaction is typically carried out in an organic solvent like DMF at ambient temperatures for about 24 hours.

The 3-methoxy substituted proline methyl ester is then treated with hydrochloric acid in dioxane to remove the t-butoxycarbonyl protecting group (Boc) and produce the salt. The deprotection is typically conducted at low to ambient temperatures (e.g., 0° C.—r.t.) for 4-6 hours.

The HCl salt is then condensed with an optionally substituted aromatic carboxylic acids under coupling conditions utilizing O-(7-azabenzotriazol-1-yl)-N,N,N',N'-tetramethyluronium hexafluorophosphate (HATU), diisopropyethylamine (DIEA), in N,N-dimethylformamide (DMF). This reaction is typically carried out at temperatures in the range of about 0° C. to about 25° C. The reaction is continued until completion, which typically occurs in 24 hours.

The methyl ester can be directly converted into the hydroxamate with methanolic hydroxylamine HCl and NaOMe. The reaction is carried out at ambient temperature for about 2 to 6 hours.

Scheme 7:

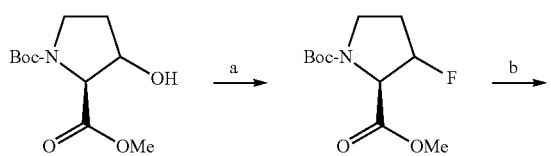

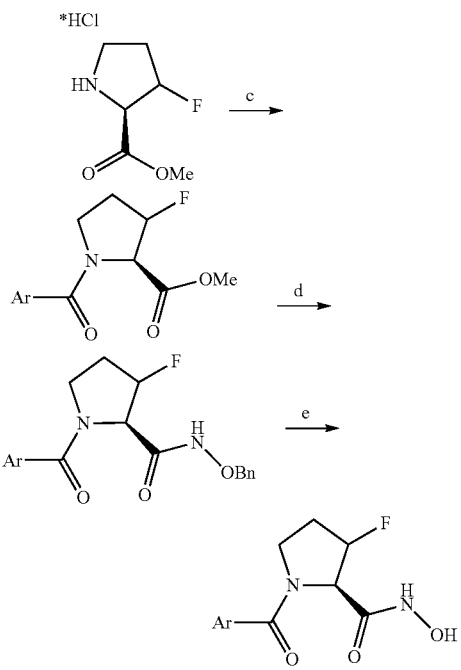

Scheme 7: Reagents and conditions.
(a) Fluorine substitution (dimethylaminosulfurtrifluoride (DAST), dichloromethane (DCM));
(b) Deprotection (4M HCl/Dioxane);
(c) Coupling (ArCOOH, HATU, DIEA, DMF);
(d) Amidation (Me₃Al, NH₂—OBn•HCl, Toluene);
(e) Hydroxamate formation (10% Pd(OH)₂/C, EtOH).

The hydroxy proline is converted to the fluoroproline by reacting with a fluorinating reagent (dimethylaminosulfurtrifluoride(DAST)) in an inert organic solvent like DCM. The reaction is typically initiated at −78° C. and progresses at ambient temperatures for about 24 hours.

The 3-fluoroproline methyl ester is then treated with hydrochloric acid in dioxane to remove the t-butoxycarbonyl protecting group (Boc) and produce the salt. The deprotection is typically conducted at low to ambient temperatures (e.g., 0° C.—r.t.) for 4-6 hours.

The HCl salt is then condensed with an optionally substituted aromatic carboxylic acids under coupling conditions utilizing O-(7-azabenzotriazol-1-yl)-N,N,N',N'-tetramethyluronium hexafluorophosphate (HATU), diisopropyethylamine (DIEA), in N,N-dimethylformamide (DMF). This reaction is typically carried out at temperatures in the range of about 0° C. to about 25° C. The reaction is continued until completion, which typically occurs in 24 hours.

The coupled product is then converted to the N-benzyloxyamide derivative by treatment with O-benzyl hydroxylamine and trimethyl aluminium in a non-polar organic solvent such as toluene. The reaction is carried out at ambient temperature to 80° C. for about 2 to 24 hours.

The N-benzyloxyamide derivative is then converted to the N-hydroxyamide derivative by hydrogenation to remove the benzyloxy protecting group (OBz). Reaction is carried out in a polar organic solvent such as ethanol. The hydrogenation is carried out at in the presence of a palladium (II) catalyst under hydrogen atmosphere. The hydrogenation conveniently may be carried at ambient temperatures in about 16 hours.

Scheme 8, additional synthesis of compounds of Formula I (a):

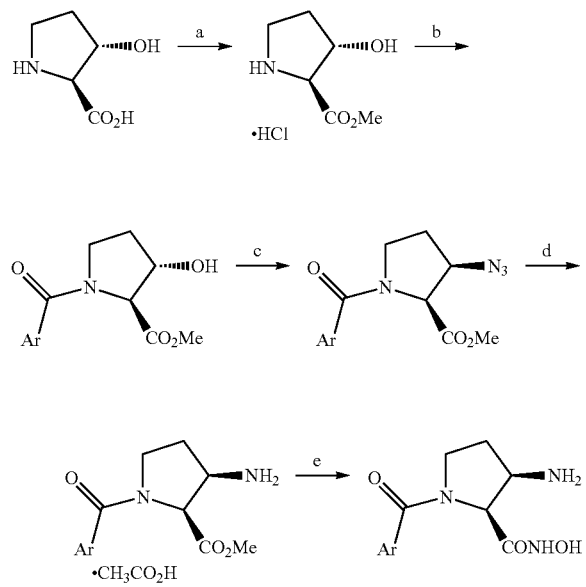

Reagents and conditions.
(a) Methyl ester formation (SOCl₂, MeOH);
(b) Coupling (ArCO₂H, HOBt, DIEA, EDC, DCM);
(c) Azide substitution (DPPA, DIAD, Ph₃P);
(d) Azide reduction (10% Pd/C, H₂, THF/H₂O/AcOH);
(e) Hydroxamate formation (50% Aq. NH₂OH, Dioxane,).

The methyl ester of hydroxyproline carboxylic acid is generated by alkylation with a suitable methylating reagent such as thionyl chloride and methanol. Transformation is typically carried out at low temperatures, e.g., 0° C., and after the addition, the reaction is allowed to warm to ambient temperature, e.g., about 25° C.

The salt is then condensed with an optionally substituted aromatic carboxylic acids under coupling conditions utilizing 1-hydroxybenzotriazole hydrate (HOBT), EDC (carbodiimide), and suitable organic bases like diisopropyethylamine (DIEA). This reaction is typically carried out in suitable inert organic solvents like N,N-dimethylformamide at temperatures in the range of about 0° C. to about 25° C., The reaction is continued until completion, which typically occurs in about 24 hours.

Reaction of 3-hydroxyproline methyl ester with DIAD, triphenylphosphine and diphenylphosphoryl azide provides the desired 3-azido proline methyl ester. Transformation is typically carried out at low temperatures, e.g., 0° C., and after the addition, the reaction is allowed to warm to ambient temperature, e.g., about 25° C.

The azide is then converted to the amine by hydrogenation. Reaction is carried out in a solvent mixture such as THF/water/acetic acid. The hydrogenation is carried out at in the presence of 10% palladium on carbon under hydrogen atmosphere. The hydrogenation conveniently may be carried at ambient temperatures in about 16 hours.

The methyl ester can be directly converted into the hydroxamate with a hydroxylamine reagent, such as 50% aqueous (aq). Hydroxylamine in dioxane. The reaction is carried out at ambient temperature for about 2 to 6 hours.

General syntheses of compounds of Formula I(b) and I(c) is illustrated by Schemes 9 and 10 below.

Scheme 9:

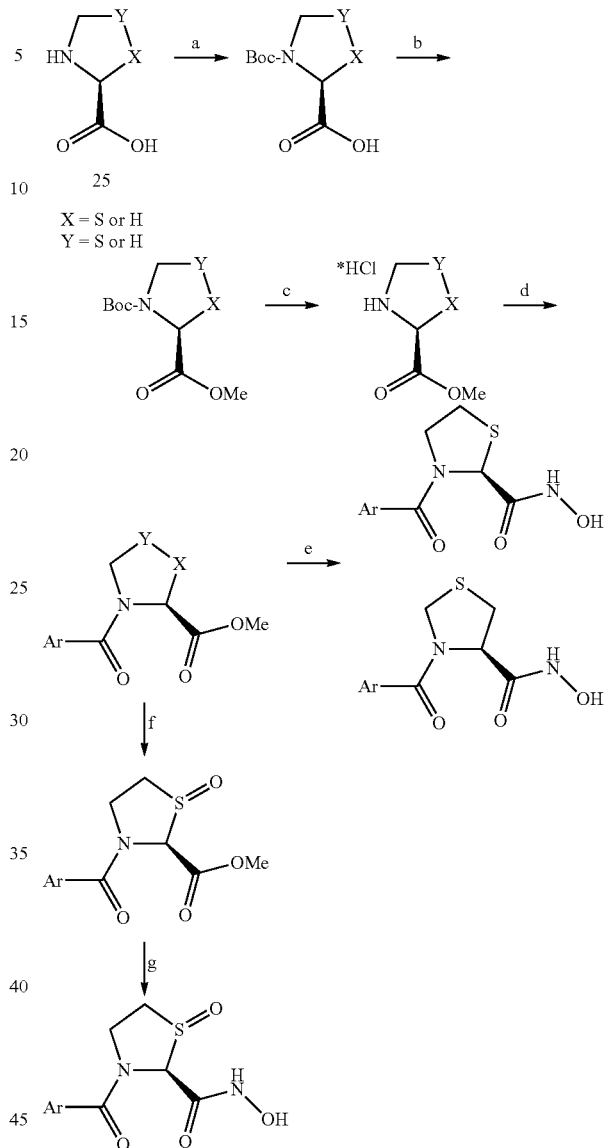

X = S or H
Y = S or H

Scheme 9: Reagents and conditions.
(a) Protection (Boc₂O, base);
(b) Methyl ester formation (TMSCHN₂, MeOH);
(c) Deprotection (4 M HCl/Dioxane);
(d) Coupling (ArCOOH, HATU, DIEA, DMF);
(e) Hydroxamate formation (NH₂OH•HCl, NaOMe, MeOH);
(f) Oxidation (3-chloroperoxybenzoic acid (MCPBA), DCM);
(g) Hydroxamate formation (50% NH₂OH, KCN(cat.), MeOH).

2-Thiazolidine or 4-thiazolidine carboxylic acid is reacted with di-tert-butyl dicarbonate (Boc₂O) in the presence of an organic or inorganic base to provide a Boc-protected amino acid. The transformation is typically carried out in an inert organic solvent, such as tetrahydrofuran (THF), at low temperatures, e.g., from 0 to 25° C., such as 0° C. Suitable organic base includes triethylamine (TEA), and a suitable inorganic base includes sodium bicarbonate.

The methyl ester of Boc-protected thiazolidine carboxylic acid is generated by alkylation with a suitable methylating reagent such as trimethylsilyl-diazomethane. Transformation is typically carried out at low temperatures, e.g., 0° C., and after the addition, the reaction is allowed to warm to ambient temperature, e.g., about 25° C.

The thiazolidine methyl ester is then treated with hydrochloric acid in dioxane to remove the t-butoxycarbonyl protecting group (Boc) and produce the salt. The deprotection is typically conducted at low to ambient temperatures (e.g., 0° C.—r.t.) for 4-6 hours.

The HCl salt is then condensed with an optionally substituted aromatic carboxylic acids under coupling conditions utilizing O-(7-azabenzotriazol-1-yl)-N,N,N',N'-tetramethyluronium hexafluorophosphate (HATU), diisopropyethylamine (DIEA), in N,N-dimethylformamide (DMF). This reaction is typically carried out at temperatures in the range of about 0° C. to about 25° C. The reaction is continued until completion, which typically occurs in 24 hours.

The methyl ester can be directly converted into the hydroxamate with a hydroxylamine reagent, such as hydroxylamine hydrochloride and NaOMe. The reaction is carried out at ambient temperature for about 2 to 6 hours.

Alternately the thiazolidine can be oxidized to the sulfoxide in the presence of 3-chloroperoxybenzoic acid (MCPBA) in an inert organic solvent like DCM. The reaction is typically carried out in the range of −10° C.-4° C. for 2-3 hours.

The sulfone bearing methyl ester can be directly converted into the hydroxamate with a hydroxylamine reagent, such as 50% aqueous (aq). Hydroxylamine in dioxane in the presence of catalytic amounts of KCN. The reaction is carried out at ambient temperature for about 2 to 6 hours.

Scheme 10:

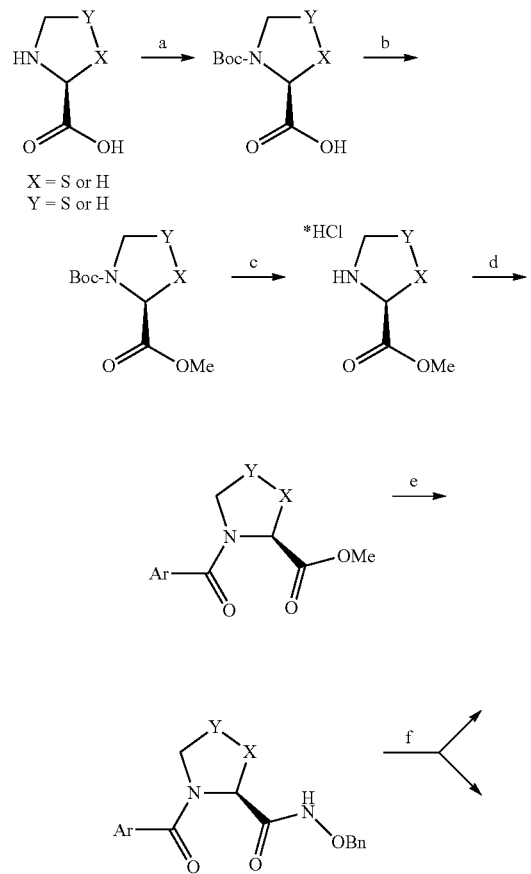

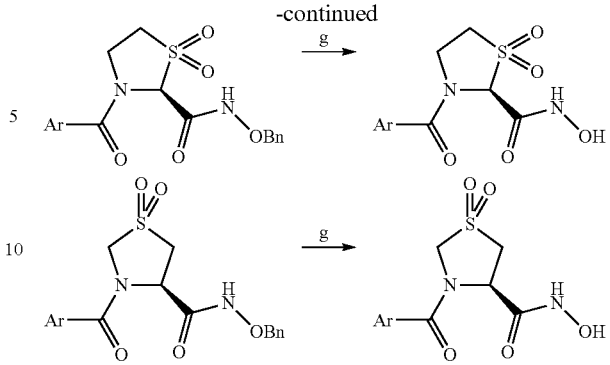

Scheme 10: Reagents and conditions.
(a) Protection (Boc₂O, base);
(b) Methyl ester formation (TMSCHN₂, MeOH);
(c) Deprotection (4 M HCl/Dioxane);
(d) Coupling (ArCOOH, HATU, DIEA, DMF);
(e) Amidation (Me₃Al, NH₂—OBn·HCl, Toluene);
(f) Oxidation (MCPBA, DCM);
(g) Hydroxamate formation (10% Pd(OH)₂, EtOH).

2-Thiazolidine or 4-thiazoilidine carboxylic acid is reacted with di-tert-butyl dicarbonate (Boc2O) in the presence of an organic or inorganic base to provide a Boc-protected amino acid. The transformation is typically carried out in an inert organic solvent, such as tetrahydrofuran (THF), at low temperatures, e.g., from 0 to 25° C., such as 0° C. Suitable organic base includes triethylamine (TEA), and a suitable inorganic base includes sodium bicarbonate.

The methyl ester of Boc-protected thiazolidine carboxylic acid is generated by alkylation with a suitable methylating reagent such as trimethylsilyl-diazomethane. Transformation is typically carried out at low temperatures, e.g., 0° C., and after the addition, the reaction is allowed to warm to ambient temperature, e.g., about 25° C.

The thiazolidine methyl ester is then treated with hydrochloric acid in dioxane to remove the t-butoxycarbonyl protecting group (Boc) and produce the salt. The deprotection is typically conducted at low to ambient temperatures (e.g., 0° C.—r.t.) for 4-6 hours.

The HCl salt is then condensed with an optionally substituted aromatic carboxylic acids under coupling conditions utilizing O-(7-azabenzotriazol-1-yl)-N,N,N',N'-tetramethyluronium hexafluorophosphate (HATU), diisopropyethylamine (DIEA), in N,N-dimethylformamide (DMF). This reaction is typically carried out at temperatures in the range of about 0° C. to about 25° C. The reaction is continued until completion, which typically occurs in 24 hours.

The coupled product is then converted to the N-benzyloxyamide derivative by treatment with O-benzyl hydroxylamine hydrochloride and trimethyl aluminium in a non-polar organic solvent such as toluene. The reaction is carried out at ambient temperature to 80° C. for about 2 to 24 hours.

The 2-thiazolidine or 4-thiazolidine can be oxidized to the corresponding sulfone in the presence of 3-chloroperoxybenzoic acid (MCPBA) in an inert organic solvent like DCM. The reaction is typically carried out at ambient temperatures for about 24 hours.

In each case the N-benzyloxyamide derivative is then converted to the N-hydroxyamide derivative by hydrogenation to remove the benzyloxy protecting group (OBz). Reaction is carried out in a polar organic solvent such as ethanol. The hydrogenation is carried out at in the presence of a palladium (II) catalyst under hydrogen atmosphere. The hydrogenation conveniently may be carried at ambient temperatures in about 6-8 hours.

General synthesis of compounds of Formula I(d) illustrated in Scheme 11 below:

Scheme 11:

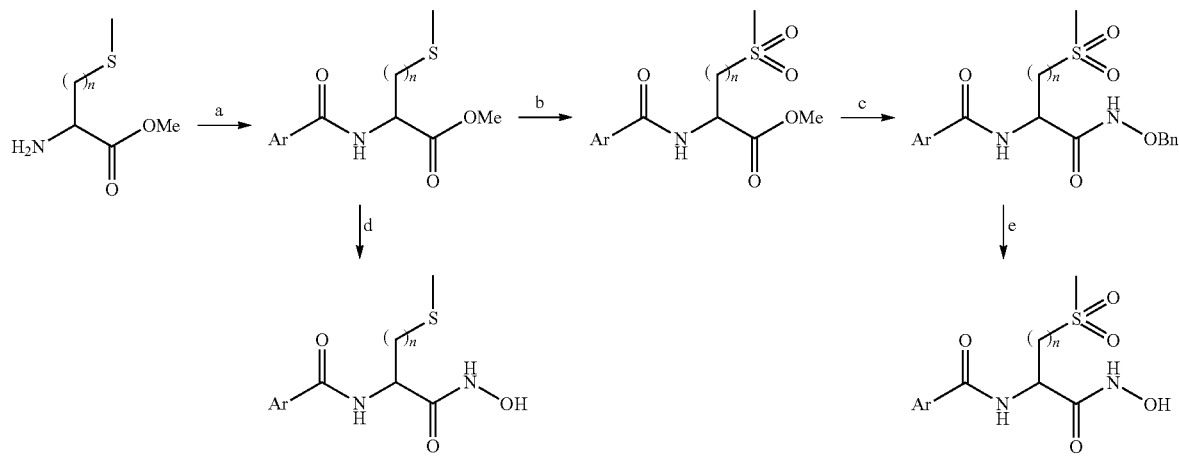

Reagents and conditions.
(a) Coupling (ArCOOH, HATU, DIEA, DMF).
(b) Oxidation (MCPBA, DCM).
(c) Amidation (Me₃Al, NH₂—OBn•HCl, toluene).
(d) Hydroxamate formation (NH₂OH•HCl, NaOMe, MeOH).
(e) Hydroxamate formation (10% Pd(OH)₂, EtOH).

The HCl salt is then condensed with an optionally substituted aromatic carboxylic acids under coupling conditions utilizing O-(7-azabenzotriazol-1-yl)-N,N,N',N'-tetramethyluronium hexafluorophosphate (HATU), diisopropyethylamine (DIEA), in N,N-dimethylformamide (DMF). This reaction is typically carried out at temperatures in the range of about 0° C. to about 25° C. The reaction is continued until completion, which typically occurs in 24 hours.

The methyl ester can be directly converted into the hydroxamate with a hydroxylamine reagent, hydroxylamine hydrochloride and NaOMe in methanol. The reaction is carried out at ambient temperature for about 2 to 6 hours.

Alternately the methionine or cysteine sulfur can be oxidized to the sulfone in the presence of 3-chloroperoxybenzoic acid (MCPBA) in an inert organic solvent like DCM. The reaction is typically carried out at ambient temperatures for about 24 hours.

The methyl ester is then converted to the N-benzyloxyamide derivative by treatment with O-benzyl hydroxylamine hydrochloride and trimethyl aluminium in a non-polar organic solvent such as toluene. The reaction is carried out at ambient temperature to 80° C. for about 2 to 24 hours.

In each case the N-benzyloxyamide derivative is then converted to the N-hydroxyamide derivative by hydrogenation to remove the benzyloxy protecting group (OBz). Reaction is carried out in a polar organic solvent such as ethanol. The hydrogenation is carried out at in the presence of a palladium (II) catalyst under hydrogen atmosphere. The hydrogenation conveniently may be carried at ambient temperatures in about 6-8 hours.

Scheme 12
below illustrate methods for preparing compounds Formula I (g)

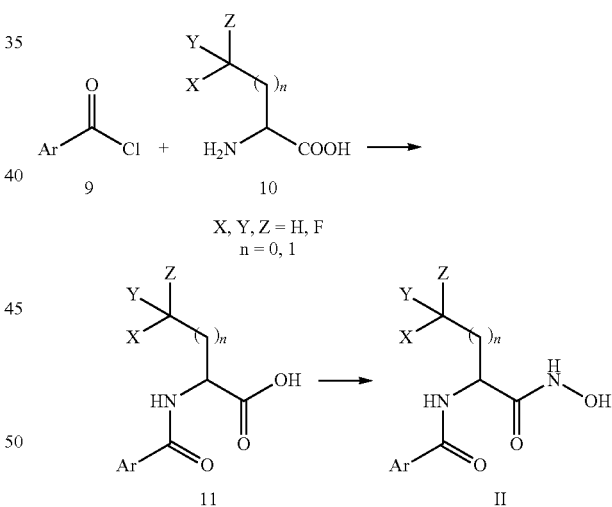

X, Y, Z = H, F
n = 0, 1

As shown in Scheme 12, to an aromatic acyl chloride (commercial or generated from respective carboxylic acid, e.g., with oxalyl chloride and catalytic DMF) is reacted with the amino acid (10) in a mixture of organic solvent and water in the presence of inorganic base to provide a amide (11). Suitable inorganic bases include sodium hydroxide, sodium bicarbonate, and the like. Suitable inert organic solvents include dichloromethane, THF, and the like. The reaction conveniently may be conducted at ambient temperature in about 2 to 24 hours.

The methyl ester of N-acyl amino acid (11) can be generated by alkylation with a suitable methylating reagent such as trimethylsilyl-diazomethane. Transformation is typically carried out at low temperatures, e.g., 0° C., and after the addition, the reaction is allowed to warm to ambient temperatures, e.g., about 25° C. (Scheme 12). This methyl ester is then converted to the N-hydroxyamide derivative by treatment with aqueous hydroxylamine (e.g., aqueous 50% hydroxylamine) in a polar organic solvent such as dioxane and the like. The reaction is carried out at ambient temperature for about 2 to 6 hours.

Synthesis of compounds of Formula I(g) is further illustrated by Scheme 13 below.

Scheme 13:

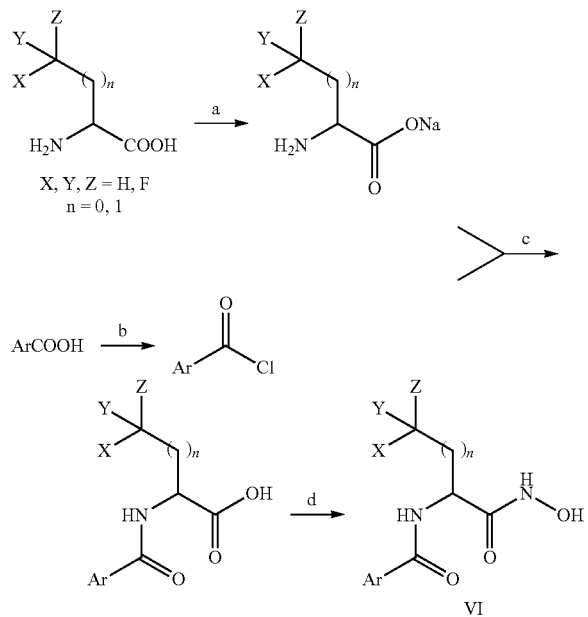

Reagents and conditions:
(a) 1 N NaOH;
(b) (COCl)$_2$, DMF (cat), DCM, 0° C.;
(c) THF;
(d) 1. TMSCHN$_2$, MeOH, 0° C. to rt,
    2. NH$_2$OH, MeOH.

Aromatic acyl chloride (commercial or generated from respective carboxylic acid, e.g., with oxalyl chloride and catalytic DMF) is reacted with the amino acid in a mixture of organic solvent and water in the presence of inorganic base to provide a amide utilizing a suitable inorganic base like sodium hydroxide. The reaction is carried out in an inert organic solvent like dichloromethane. The reaction may be conducted at ambient temperature in about 2 to 24 hours.

The methyl ester of N-acyl amino acid can be generated by alkylation with a suitable methylating reagent such as trimethylsilyl-diazomethane. Transformation is typically carried out at low temperatures, e.g., 0° C., and after the addition, the reaction is allowed to warm to ambient temperatures, e.g., about 25° C. This methyl ester is then converted to the N-hydroxyamide derivative by treatment with aqueous hydroxylamine (e.g., aqueous 50% hydroxylamine) in a polar organic solvent such as dioxane. The reaction is carried out at ambient temperature for about 2 to 6 hours.

Also provided are compositions that can be prepared by mixing one or more compounds described herein, or pharmaceutically acceptable salts or tautomers thereof, with pharmaceutically acceptable carriers, excipients, binders, diluents or the like, to treat or ameliorate a variety of bacterial infections. A therapeutically effective dose or amount refers to that amount of one or more compounds described herein sufficient to result in amelioration of symptoms of the infection. The pharmaceutical compositions of the instant invention can be manufactured by methods well known in the art such as conventional granulating, mixing, dissolving, encapsulating, lyophilizing, emulsifying or levigating processes, among others. The compositions can be in the form of, for example, granules, powders, tablets, capsule syrup, suppositories, injections, emulsions, elixirs, suspensions or solutions. The instant compositions can be formulated for various routes of administration, for example, by oral administration, by transmucosal administration, by rectal administration, or subcutaneous administration as well as intrathecal, intravenous, intramuscular, intraperitoneal, intranasal, intraocular or intraventricular injection. The compound or compounds of the instant invention can also be administered in a local rather than a systemic fashion, such as injection as a sustained release formulation. The following dosage forms are given by way of example and should not be construed as limiting the instant invention.

For oral, buccal, and sublingual administration, powders, suspensions, granules, tablets, pills, capsules, gelcaps, and caplets are acceptable as solid dosage forms. These can be prepared, for example, by mixing one or more compounds of the instant invention, or pharmaceutically acceptable salts or tautomers thereof, with at least one additive or excipient such as a starch or other additive. Suitable additives or excipients are sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi synthetic polymers or glycerides, methyl cellulose, hydroxypropylmethyl cellulose, and/or polyvinylpyrrolidone. Optionally, oral dosage forms can contain other ingredients to aid in administration, such as an inactive diluent, or lubricants such as magnesium stearate, or preservatives such as paraben or sorbic acid, or anti oxidants such as ascorbic acid, tocopherol or cysteine, a disintegrating agent, binders, thickeners, buffers, sweeteners, flavoring agents or perfuming agents. Additionally, dyestuffs or pigments can be added for identification. Tablets and pills can be further treated with suitable coating materials known in the art.

Liquid dosage forms for oral administration can be in the form of pharmaceutically acceptable emulsions, syrups, elixirs, suspensions, slurries and solutions, which can contain an inactive diluent, such as water. Pharmaceutical formulations can be prepared as liquid suspensions or solutions using a sterile liquid, such as, but not limited to, an oil, water, an alcohol, and combinations of these. Pharmaceutically suitable surfactants, suspending agents, emulsifying agents, can be added for oral or parenteral administration.

As noted above, suspensions can include oils. Such oils include peanut oil, sesame oil, cottonseed oil, corn oil, olive oil and mixtures of oils. Suspension preparation can also contain esters of fatty acids such as ethyl oleate, isopropyl myristate, fatty acid glycerides and acetylated fatty acid glycerides. Suspension formulations can include alcohols, such as, but not limited to, ethanol, isopropyl alcohol, hexadecyl alcohol, glycerol and propylene glycol. Ethers, such as but not limited to, poly(ethyleneglycol), petroleum hydrocarbons such as mineral oil and petrolatum; and water can also be used in suspension formulations.

For nasal administration, the pharmaceutical formulations can be a spray or aerosol containing and appropriate solvents and optionally other compounds such as, but not limited to, stabilizers, antimicrobial agents, antioxidants, pH modifiers, surfactants, bioavailablity modifiers and combinations of these. A propellant for an aerosol formulation can include compressed air, nitrogen, carbon dioxide, or a hydrocarbon based low boiling solvent. The compound or compounds of the instant invention are conveniently delivered in the form of an aerosol spray presentation from a nebulizer or the like.

Injectable dosage forms generally include aqueous suspensions or oil suspensions which can be prepared using a suitable dispersant or wetting agent and a suspending agent. Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Generally, the oil or fatty acid is non volatile, including natural or synthetic oils, fatty acids, mono, di or tri glycerides.

For injection, the pharmaceutical formulation can be a powder suitable for reconstitution with an appropriate solution as described above. Examples of these include freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi dose containers.

For rectal administration, the pharmaceutical formulations can be in the form of a suppository, an ointment, an enema, a tablet or a cream for release of compound in the intestines, sigmoid flexure and/or rectum. Rectal suppositories are prepared by mixing one or more compounds of the instant invention, or pharmaceutically acceptable salts or tautomers of the compound, with acceptable vehicles, for example, cocoa butter or polyethylene glycol, which is present in a solid phase at normal storing temperatures, and present in a liquid phase at those temperatures suitable to release a drug inside the body, such as in the rectum. Oils can also be employed in the preparation of formulations of the soft gelatin type and suppositories. Water, saline, aqueous dextrose and related sugar solutions, and glycerols can be employed in the preparation of suspension formulations which can also contain suspending agents such as pectins, carbomers, methyl cellulose, hydroxypropyl cellulose or carboxymethyl cellulose, as well as buffers and preservatives.

Besides those representative dosage forms described above, pharmaceutically acceptable excipients and carries are generally known to those skilled in the art and are thus included in the instant invention. Such excipients and carriers are described, for example, in "Remingtons Pharmaceutical Sciences" Mack Pub. Co., New Jersey (1991).

The formulations of the invention can be designed for to be short acting, fast releasing, long acting, and sustained releasing. Thus, the pharmaceutical formulations can also be formulated for controlled release or for slow release.

The instant compositions can also comprise, for example, micelles or liposomes, or some other encapsulated form, or can be administered in an extended release form to provide a prolonged storage and/or delivery effect. Therefore, the pharmaceutical formulations can be compressed into pellets or cylinders and implanted intramuscularly or subcutaneously as depot injections or as implants such as stents. Such implants can employ known materials such as silicones and biodegradable polymers.

The compositions can contain, for example, from about 0.1% by weight, to about 90% or more by weight, of the active material, depending on the method of administration. Where the compositions comprise dosage units, each unit can contain, for example, from about 5 to 500 mg or more of the active ingredient. The dosage as employed for adult human treatment can range, for example, from about 10 to 3000 mg per day, depending on the route and frequency of administration.

Specific dosages can be adjusted depending on conditions of infection, the age, body weight, general health conditions, sex, and diet of the subject, dose intervals, administration routes, excretion rate, and combinations of drugs. Any of the above dosage forms containing effective amounts are well within the bounds of routine experimentation and therefore, well within the scope of the instant invention. Generally, the total daily dose can typically range from about 0.1 mg/kg/day to about 500 mg/kg/day in single or in divided doses. Typically, dosages for humans can range from about 10 mg to about 3000 mg per day, in a single or multiple doses.

A therapeutically effective dose or amount can vary depending upon the route of administration and dosage form. Some compositions of the instant invention provide a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ can be determined by standard pharmaceutical procedures in animal cell cultures or experimental models.

In one embodiment, the invention provides methods of treating or preventing a bacterial infection in a subject, such as a mammal, e.g., a human or non human mammal, comprising administering an effective amount of one or more compounds described herein to the subject. Suitable subjects that can be treated include domestic or wild animals, companion animals, such as dogs, cats and the like; livestock, including horses, cows and other ruminants, pigs, poultry, rabbits and the like; primates, for example monkeys, such as rhesus monkeys and cynomolgus (also known as crab eating or long tailed) monkeys, marmosets, tamarins, chimpanzees, macaques and the like; and rodents, such as rats, mice, gerbils, guinea pigs and the like. In one embodiment, the compound is administered in a pharmaceutically acceptable form, optionally in a pharmaceutically acceptable carrier. The compounds described herein can be used for the treatment or prevention of infectious disorders caused by a variety of bacterial organisms, including infections by pathogenic bacterial species. Infections of Gram negative aerobic and anaerobic bacteria that may be treated include those set forth in Example A.

Infections that can be treated with the described compounds include central nervous system infections, external ear infections, infections of the middle ear, such as acute otitis media, infections of the cranial sinuses, eye infections, infections of the oral cavity, such as infections of the teeth, gums and mucosa, upper respiratory tract infections, lower respiratory tract infections, genitourinary infections, gastrointestinal infections, gynecological infections, bacteremia, septicemia, bone and joint infections, skin and skin structure infections, bacterial endocarditis, burns, antibacterial prophylaxis of surgery, and antibacterial prophylaxis in immunosuppressed patients, such as patients receiving cancer chemotherapy, or organ transplant patients. These infections can be treated in hospital or community settings via various routes of administration as described herein.

The compounds or compositions described herein can also be used prophylactically. The compounds or compositions described herein can also be used empirically, i.e. when a patient exhibits symptoms consistent with an infection, but a true infection has not yet diagnosed, for example by blood tests. Accordingly, one or more of the present compounds or compositions can be administered to an individual deemed to be at risk for developing a microbial infection or having conditions consistent with a microbial infection. Individuals at risk for developing a microbial infection include individuals who have been exposed to a particular microorganism, such as a pathogenic bacterial species; individuals having a compromised immune system, such as individuals suffering from an immunodeficiency disease or taking immunocompromising medication; patients on antimicrobial therapy and individuals having a history of repeated or chronic infection, such as children who have repeated infections of the middle ear.

Another embodiment provides a method of killing or preventing the growth of bacteria that includes contacting a bacteria with either a non-therapeutic amount or a therapeutically effective amount of one or more of the present compounds. Such methods can occur in vivo or in vitro. In vitro contact can involve a screening assay to determine the efficacy of the one or more compounds against selected bacteria at various amounts or concentrations. In vivo contact with a therapeutically effective amount of the one or more compounds can involve treatment or prophylaxis of a bacterial infection in the animal in which the contact occurs. The effect of the one or more compounds on the bacteria and/or host animal can also be determined or measured.

Included within the scope of the invention are all isomers (e.g. stereoisomers, diastereoisomers, epimers, geometrical isomers) of the compounds described herein as well as any wholly or partially equilibrated mixtures thereof (e.g. racemic or optically active mixtures). The present invention also covers the individual isomers of the compounds represented by the formulas herein as mixtures with isomers thereof in which one or more chiral centers are inverted.

Stereoisomeric mixtures, e.g. mixtures of diastereomers, can be separated into their corresponding isomers in a known manner by means of suitable separation methods. Diastereomeric mixtures for example can be separated into their individual diastereomers by means of fraction crystallization, chromatography, solvent distribution, and similar procedures. This separation can take place either at the level of one of the starting compounds or in a compound of formula I itself. Enantiomers can be separated through the formation of diastereomeric salts, for example by salt formation with an enantiomerically pure chiral acid, or by means of chromatography, for example by HPLC, using chiral chromatographic media.

It is understood that some of the compounds described herein can exhibit the phenomenon of tautomerism. As the chemical structures sometimes only represent one of the possible tautomeric forms, it should be understood that the invention encompasses any tautomeric form of the represented structure.

In addition, the compounds described herein can exist in unsolvated as well as solvated forms with pharmaceutically acceptable solvents such as water, ethanol, and the like. In general, the solvated forms are considered equivalent to the unsolvated forms for the purposes of the present invention.

Certain compounds described herein are also useful as intermediates for preparing other described compounds and such intermediates are included within the scope of the present invention. Specific compounds are described throughout with particular reference to the Examples and the following table:

TABLE 2

| Compound/ Example No. | Name | Structure |
|---|---|---|
| 1 | (2S,3S)-3-Azido-N-hydroxy-1-(4'-propylbiphenylcarbonyl)pyrrolidine-2-carboxamide | 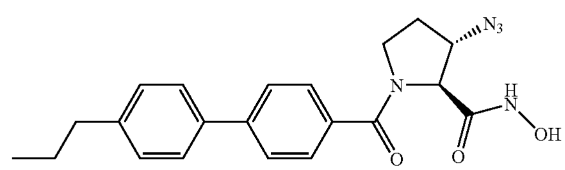 |
| 2 | (2S,3S)-3-Amino-N-hydroxy-1-(4'-propylbiphenylcarbonyl)pyrrolidine-2-carboxamide | 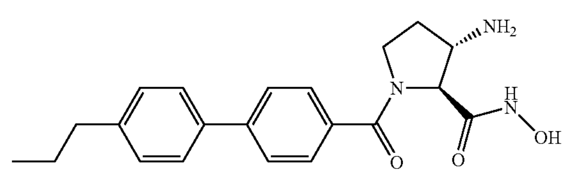 |
| 3 | (2S,3S)-N-Hydroxy-3-(methylsulfonamido)-1-(4'-propylbiphenylcarbonyl)pyrrolidine-2-carboxamide | 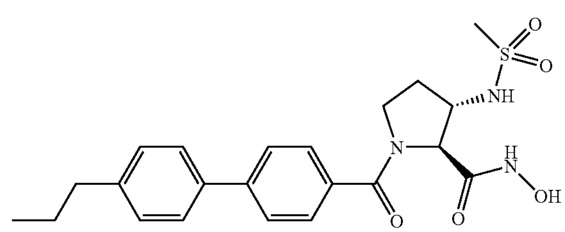 |

TABLE 2-continued

| Compound/Example No. | Name | Structure |
|---|---|---|
| 4 | (2S,3S)-3-Formamido-N-hydroxy-1-(4'-propylbiphenylcarbonyl)pyrrolidine-2-carboxamide | 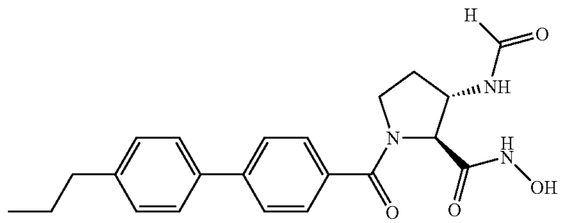 |
| 5 | (2S,3S)-Methyl-3-(methylamino)-1-(4'-propylbiphenylcarbonyl)pyrrolidine-2-carboxamide | 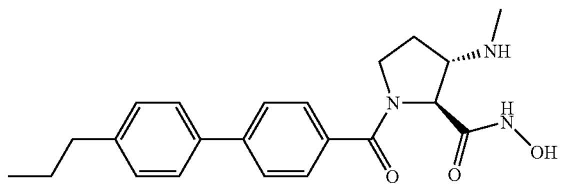 |
| 6 | (2S,3S)-3-Fluoro-N-hydroxy-1-(4'-propylbiphenylcarbonyl)pyrrolidine-2-carboxamide | 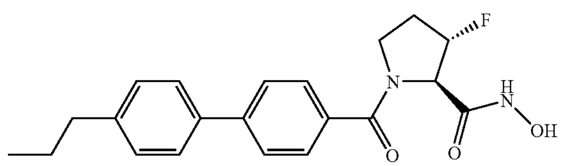 |
| 7 | (2S,3S)-N-Hydroxy-3-methoxy-1-(4'-propylbiphenylcarbonyl)pyrrolidine-2-carboxamide | 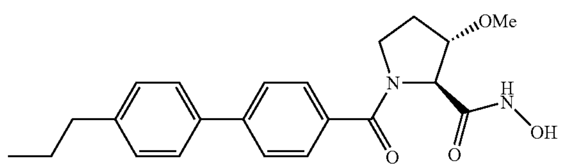 |
| 8 | (2S,3R)-N-Hydroxy-3-methoxy-1-(4'-propylbiphenylcarbonyl)pyrrolidine-2-carboxamide | 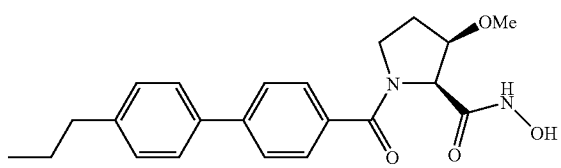 |
| 9 | (2S,4R)-N,4-Dihydroxy-4-(methoxymethyl)-1-(4'-propylbiphenylcarbonyl)pyrrolidine-2-carboxamide | 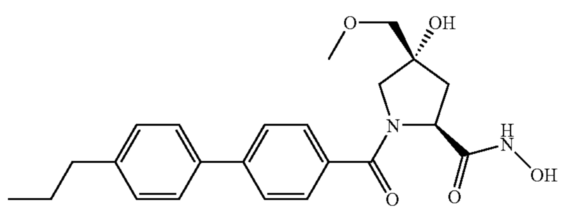 |
| 10 | (2S,3R,4S)-N,3,4-Trihydroxy-1-(4'-propylbiphenylcarbonyl)pyrrolidine-2-carboxamide | 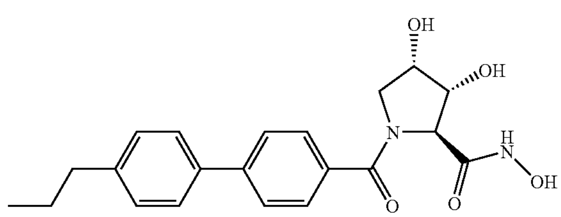 |
| 11 | (2S,3S,4R)-4-Amino-N,3-dihydroxy-1-(4'-propylbiphenylcarbonyl)pyrrolidine-2-carboxamide | 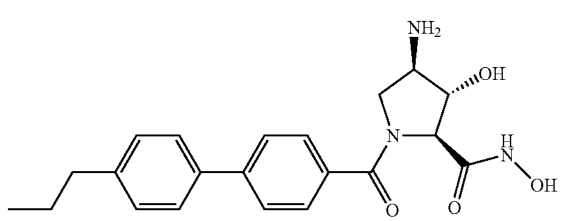 |

TABLE 2-continued

| Compound/Example No. | Name | Structure |
|---|---|---|
| 12 | (2S,3R,4S)-4-Amino-N,3-dihydroxy-1-(4'-propylbiphenylcarbonyl)pyrrolidine-2-carboxamide | 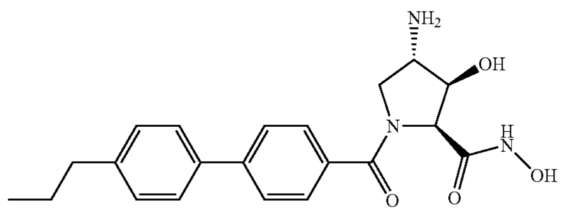 |
| 13 | (S)-N-Hydroxy-3-(4'-propylbiphenylcarbonyl)thiazolidine-2-carboxamide | 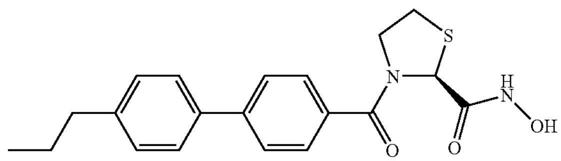 |
| 14 | (S)-N-Hydroxy-3-(4'-propylbiphenylcarbonyl)thiazolidine-sulfoxide-2-carboxamide | 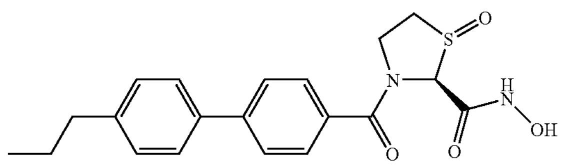 |
| 15 | (S)-N-Hydroxy-3-(4'-propylbiphenylcarbonyl)thiazolidine-sulfone-2-carboxamide | 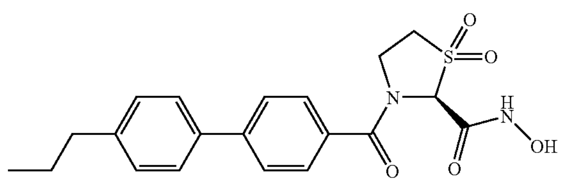 |
| 16 | (S)-N-Hydroxy-3-(4'-propylbiphenylcarbonyl)thiazolidine-2-carboxamide | 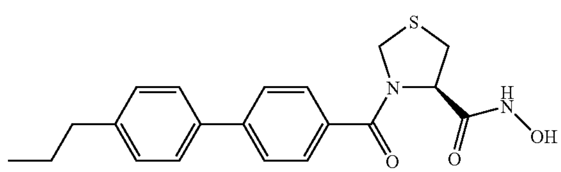 |
| 17 | (S)-N-Hydroxy-3-(4'-propylbiphenylcarbonyl)thiazolidine-sulfone-4-carboxamide | 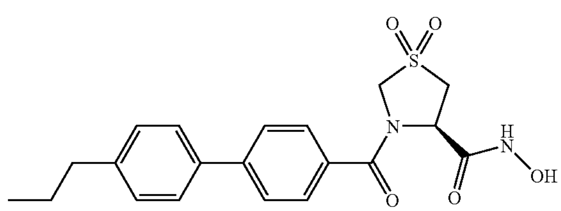 |
| 18 | (R)-N-Hydroxy-3-(4'-propylbiphenylcarbonyl)thiazolidine-2-carboxamide | 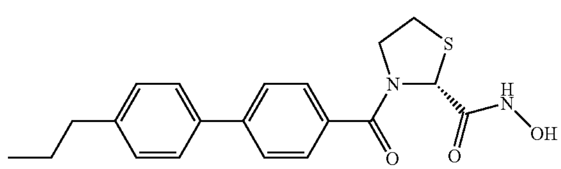 |
| 19 | (R)-N-Hydroxy-3-(4'-propylbiphenylcarbonyl)thiazolidine-sulfone-2-carboxamide | 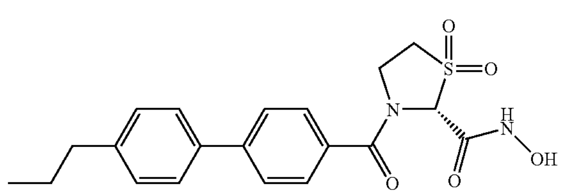 |

TABLE 2-continued

| Compound/Example No. | Name | Structure |
|---|---|---|
| 20 | DL-4'-Propyl-biphenyl-4-carboxylic acid (2,2,2-trifluoro-1-hydroxycarbamoyl-ethyl)-amide | 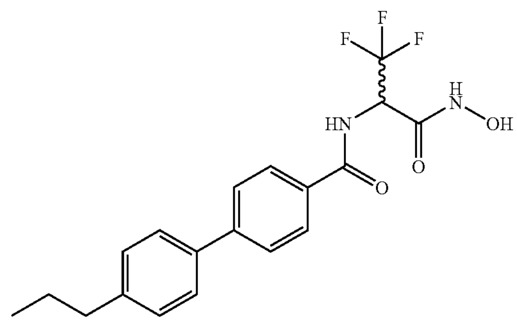 |
| 21 | DL-4'-Propyl-biphenyl-4-carboxylic acid (2-fluoro-1-hydroxycarbamoyl-ethyl)-amide | 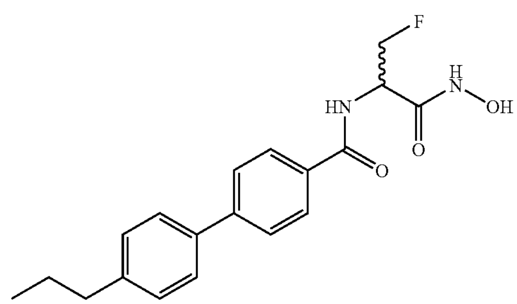 |
| 22 | DL-4'-Ethoxy-biphenyl-4-carboxylic acid (2,2,2-trifluoro-1-hydroxycarbamoyl-ethyl)-amide | 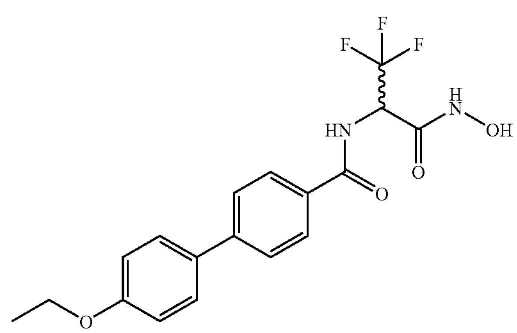 |
| 23 | DL-3',5'-Difluoro-biphenyl-4-carboxylic acid (2,2,2-trifluoro-1-hydroxycarbamoyl-ethyl)-amide | 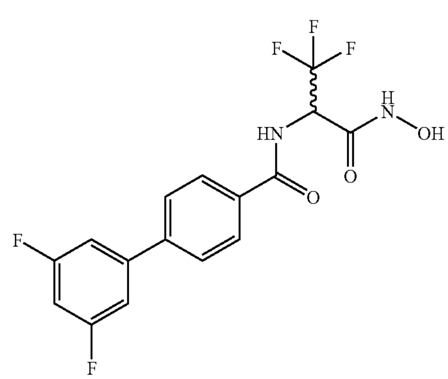 |

TABLE 2-continued

| Compound/ Example No. | Name | Structure |
|---|---|---|
| 24 | DL-4-Thiophen-3-yl-N-(2,2,2-trifluoro-1-hydroxycarbamoyl-ethyl)-benzamide | 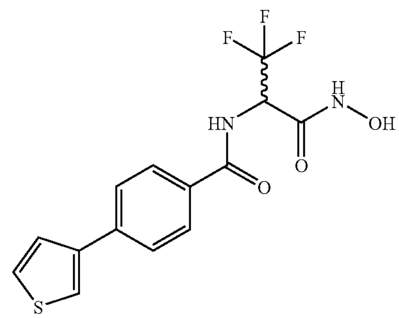 |
| 25 | DL-4'-Fluoro-N-(1,1,1-trifluoro-3-(hydroxyamino)-3-oxopropan-2-yl)biphenyl-4-carboxamide | 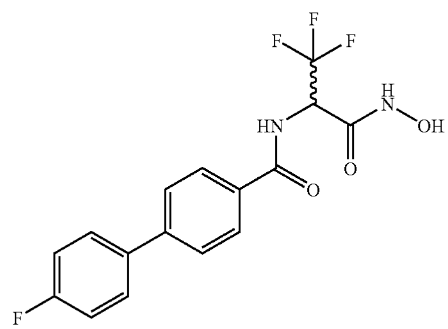 |
| 26 | (S)-N-(1-(Hydroxyamino)-4-(methylthio)-1-oxobutan-2-yl)-4'-propylbiphenyl-4-carboxamide | 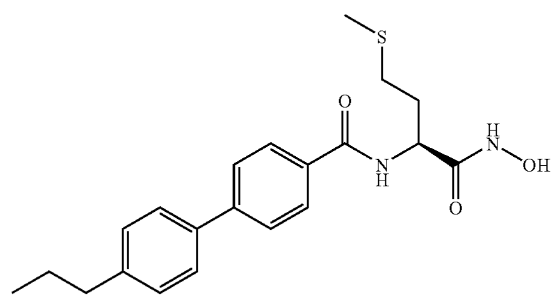 |
| 27 | (S)-N-(1-(Hydroxyamino)-4-(methylsulfone)-1-oxobutan-2-yl)-4'-propylbiphenyl-4-carboxamide | 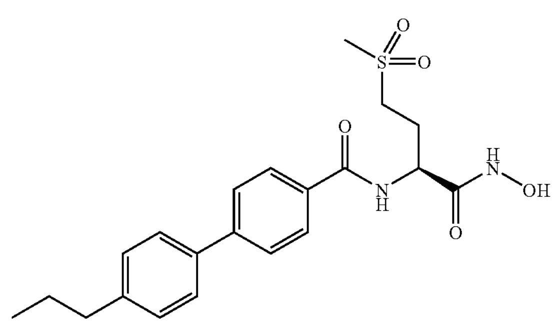 |
| 28 | (S)-N-(1-(Hydroxyamino)-3-(methylthio)-1-oxopropan-2-yl)-4'-propylbiphenyl-4-carboxamide | 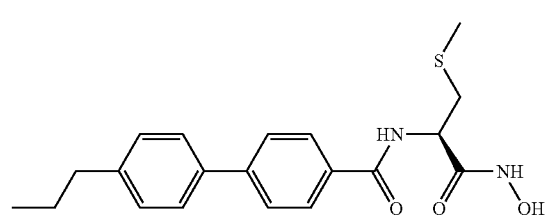 |

TABLE 2-continued

| Compound/Example No. | Name | Structure |
|---|---|---|
| 29 | (S)-N-(1-(Hydroxyamino)-3-(methylsulfone)-1-oxopropan-2-yl)-4'-propylbiphenyl-4-carboxamide | 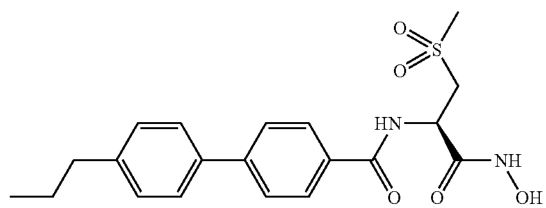 |
| 30 | N-(2-(Hydroxyamino)-2-oxo-1-(thiophen-2-yl)ethyl)-4'-propylbiphenyl-4-carboxamide | 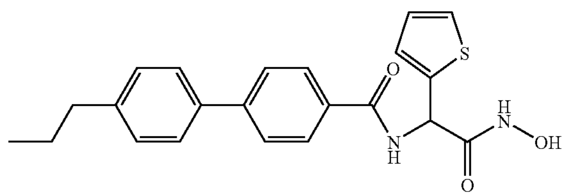 |
| 31 | (S)-3-(1H-Imidazol-1-yl)-2-(4'-propylbiphenyl-4-ylcarboxamido)propanoic acid | 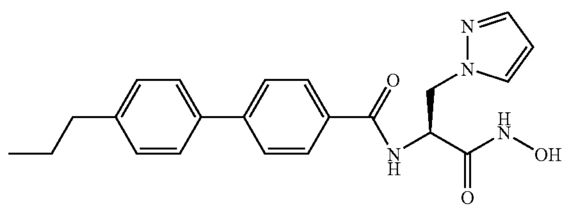 |
| 32 | Methyl 4-(3-(trifluoromethylthio)phenylcarbamoyl)furan-3-carboxylate | 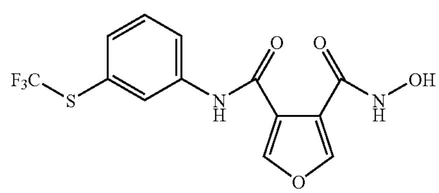 |
| 33 | (S)-3-(4'-Ethoxybiphenylcarbonyl)-N-hydroxythiazolidinesulfone-2-carboxamide | 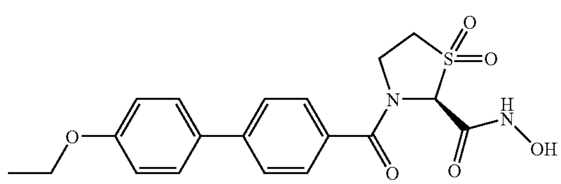 |
| 34 | (2S,3R)-3-Amino-N-hydroxy-1-(4'-ethylbiphenylcarbonyl)pyrrolidine-2-carboxamide | 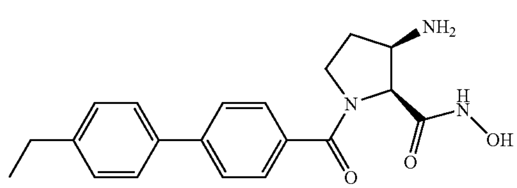 |
| 35 | (S)-N-Hydroxy-3-(4-phenoxybenzoyl)thiazolidinesulfone-2-carboxamide | 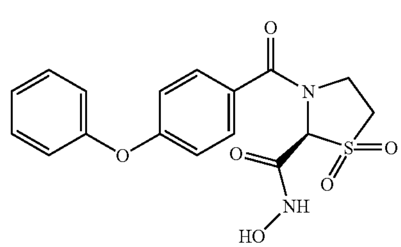 |

TABLE 2-continued

| Compound/Example No. | Name | Structure |
|---|---|---|
| 36 | (S)-3-(3',5'-Difluorobiphenylcarbonyl)-N-hydroxythiazolidinesulfone-2-carboxamide | 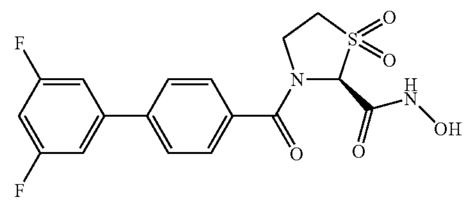 |
| 37 | (S)-3-(4'-Fluorobiphenylcarbonyl)-N-hydroxythiazolidinesulfone-2-carboxamide | 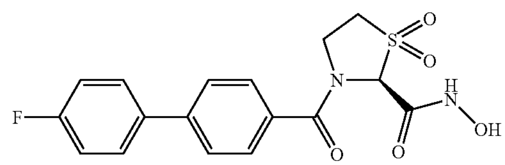 |
| 38 | (S)-3-(4'-(Trifluoromethyl)biphenylcarbonyl)-N-hydroxythiazolidinesulfone-2-carboxamide | 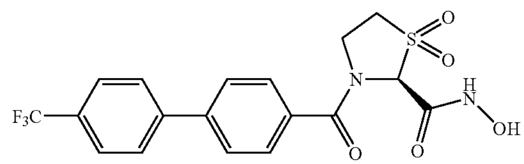 |
| 39 | (2S,3R)-3-Hydroxy-N-hydroxy-1-(4'-propylbiphenylcarbonyl)pyrrolidine-2-carboxamide | 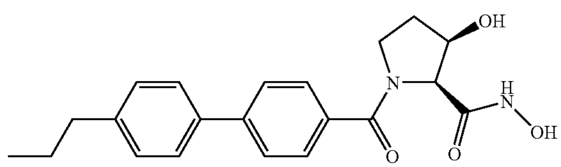 |
| 40 | (2S,3R)-3-Hydroxy-N-hydroxy-1-(4-methoxy-3-trifluoromethylsulfanyl-benzoyl)-pyrrolidine-2-carboxamide | 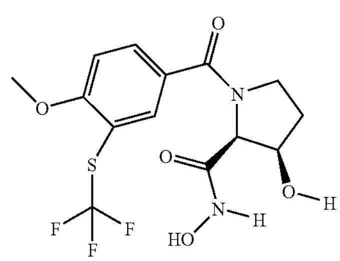 |

EXAMPLES

General Methods

Method A: To a stirred solution of the carboxylic acid (20.3 mmol) in tetrahydrofuran (75 ml) was added di-tert-butyl dicarbonate (2.5 equivalents (eq.), 50.8 mmol) followed by the addition of sodium bicarbonate (6 eq., 122 mmol) in water (75 ml). The carboxylic acids are commercially available from vendors like Aldrich, Acros, Anaspec, CNH technologies, etc. The addition is typically carried out at low temperatures, e.g. 0° C., after which the reaction was brought to rt and let to stir for 16 h. The reaction was concentrated to remove all solvent, diluted with excess water and extracted with ether. The aqueous layer was acidified with 6N HCl and extracted with DCM (2×) and once with n-butanol. All organic extracts were combined, concentrated, and co-evaporated with toluene. The residue was then dried under high vacuum to give the desired Boc-protected carboxylic acid.

Method B: The Boc-protected acid (7.35 mmol, 1 eq.) was taken into THF-MeOH (1:1) and the reaction cooled to 0° C. 2M TMSCHN$_2$ in ether (7.35 ml, 2 eq.) was added with stirring in one portion, and the reaction stirred at 0° C. for 2 h. The reaction was monitored by thin layer chromatography (TLC) (eluent: 4:1 hexanes-ethyl acetate). Solvent was removed under vacuum. The residue was purified by SiO$_2$ column chromatography (gradient 20%-40% ethyl acetate in hexanes) to provide the desired methyl ester.

Method C: DIAD (1.5 eq) was added to a mixture of the trans-hydroxyproline methyl ester (1.0 eq.), benzoic acid (1.5 eq.) and triphenylphosphine (1.5 eq.) in THF at 0° C. The reaction was slowly warmed to rt and stirred for an additional 16 h. Solvents were removed under vacuum, and the residue triturated with ether at 0° C. to remove triphenylphosphine oxide. Upon filtration, the filtrate was concentrated and subjected to column chromatography (SiO$_2$, gradient 25%-35% ethyl acetate/hexanes) to give the desired O-benzoyl protected intermediate.

Method D: The cis-O-benzoyl protected methyl ester was taken into MeOH and 0.5M sodium methoxide was added with stirring at 0° C. The reaction was stirred at rt for 2 h. It was then neutralized with Amberlite H+ resin, filtered, concentrated under high pressure and purified by SiO$_2$ column chromatography (gradient 10-20% acetone in DCM) to give the corresponding cis-3-hydroxyproline methyl ester.

Method E: DIAD (23.88 mmol, 1.3 eq.) was added dropwise with stirring to a solution of cis-3-hydroxyproline methyl ester# (18.36 mmol, 1 eq.) and triphenylphosphine (22.9 mmol, 1.25 eq.) in THF (100 mL) at 0° C. Then a solution of diphenylphosphoryl azide (22.9 mmol, 1.25 eq.) in THF (20 ml) was added. The reaction was slowly warmed to rt and stirred for 16 h. The solvent was then removed under vacuum, and the residue triturated with cold ether to remove triphenylphosphine oxide. Upon filtration, the filtrate was concentrated and subjected to column chromatography ($SiO_2$, gradient 15%-20% ethyl acetate/hexanes) to give the desired trans-3-azido-proline compound.

Method F: The Boc-protected methyl ester was taken into excess 4M HCl/dioxane (25 ml) and the reaction stirred at rt for 4 h. It was then concentrated, and the residue triturated with ether to precipitate the desired hydrochloric acid salt. This salt was dried under high vacuum.

Method G: Carboxylic acid (0.91 mmol), DMF (20 mL), and DIEA (0.64 ml, 3.67 mmol) are combined and stirred at rt. Amine (1.19 mmol) and HATU (451 mg, 1.19 mmol) are added to the stirring mixture. The combined mixture is stirred for 18 h. Ethyl acetate (100 ml) is added. The diluted mixture is washed consecutively with 10% citric acid solution, brine, saturated sodium bicarbonate solution, and again with brine. The ethyl acetate layer is dried over sodium sulfate and concentrated in vacuo. The crude product is used in the next reaction without further purification. In cases where purification was performed, the compounds were purified by column chromatography ($SiO_2$, gradient 30-40% ethyl acetate/hexanes).

Method H: Methyl ester (0.76 mmol), hydroxylamine hydrochloride (524 mg, 7.54 mmol), and MeOH are stirred at rt. Sodium methoxide (98%, 499 mg, 9.05 mmol) is added, and the reaction is monitored by HPLC. If the reaction is not completed within 2 h, an additional charge of sodium methoxide (98%, 499 mg, 9.05 mmol) is added and the reaction is monitored again by HPLC. The crude mixture is concentrated, dissolved in dimethyl sulfoxide (DMSO), and purified by preparative-HPLC.

Method I: 2M Trimethylaluminium in toluene (4 eq.) was slowly added to a suspension of the O-benzylhydroxylamine hydrochloride (4 eq.) in toluene at 0° C. under nitrogen. The reaction was brought to rt slowly and stirred for 1 h. This mixture was then added to a solution of the methyl ester # (1 eq.) in toluene at rt. The combined mixture was heated at 54° C. for 1-2 h, and the reaction was monitored by TLC (7:3 hexanes/ethyl acetate). Solvent was removed under vacuum, and the residue taken into excess ethyl acetate, washed with 10% citric acid (2×) and brine once. The organic extract was dried over sodium sulfate, filtered, concentrated and purified by column chromatography ($SiO_2$, gradient 0-10% acetone/DCM) to provide the protected hydroxamate intermediate.

Method J: To a solution of the protected hydroxamate (1.37 mmol) in ethanol (25 ml) under a nitrogen atmosphere, 10%/wt of 10% Pd/C (70 mg) was added and the reaction evacuated and stabilized to a hydrogen atmosphere. The reaction was stirred for 12 h, filtered through a pad of Celite and the filtrate concentrated to provide the desired final inhibitor.

Method K: To a solution of the methyl ester (8.93 mmol) in ethanol (50 ml), with small amounts of MeOH to dissolve the compound, under a nitrogen atmosphere, 10% Pd/C (350-400 mg; ca. 10% weight of the substrate) was added and the reaction evacuated and stabilized to a hydrogen atmosphere. The reaction is stirred for 2-3 h, filtered through a pad of Celite and the filtrate concentrated to provide the desired free amine compound.

Method L: To a cold solution of the 3-aminoproline intermediate (0.137 mmol, 1 eq.) in pyridine, methanesulfonyl chloride (1 eq.) was added slowly, and the reaction was stirred at 0° C. for 30 min. It was slowly brought to rt and stirred for an additional 16 h. The reaction was concentrated, and the residue was taken into excess ethyl acetate. The organic mixture was washed with 10% citric acid and brine. The combined organic extracts were dried over sodium sulfate, filtered, concentrated and purified by column chromatography ($SiO_2$, gradient 15-25% acetone/DCM) to provide the desired sulfonamide.

Method M: A 5:1 mixture of formic acid and acetic anhydride was heated at 60° C. for 1-1.5 h. The mixture was cooled and added to the 3-aminoproline intermediate, and the mixture stirred for 8-24 h. The reaction was monitored by HPLC. It was concentrated under vacuum, co-evaporated with toluene and DCM, and the residue purified by column chromatography ($SiO_2$, gradient 0-30% acetone/DCM, then 2.5%-5% MeOH/DCM) to provide the N-formyl compound.

Method N: A solution of the N-formyl intermediate (1.78 mmol, 1 eq.) in tetrahydrofuran was cooled to 0° C. Commercially available borane-methylsulfide complex (3.36 mmol, 2 eq.) was added drop-wise and the mixture stirred at rt for 5 h. It was then quenched with MeOH (15 ml) and stirred at rt for an additional 16 h. 2M HCl/MeOH was added, and the reaction mixture refluxed for 3 h. The reaction was concentrated, and excess DCM was added. Under stirring conditions at 0° C. sodium bicarbonate was slowly added till the ph of the reaction was ~8. The organic layer was separated and the aqueous layer thoroughly washed with DCM. The organic extracts were combined, dried over sodium sulfate, filtered, concentrated and purified by column chromatography ($SiO_2$, 0-20% acetone/DCM, then 2.5%-5% MeOH/DCM) to provide the desired N-methylated intermediate.

Method O: To a solution of the 3-hydroxyproline methyl ester in DCM at −78° C., DAST (4 eq.) was added dropwise with stirring. The reaction was slowly warmed to rt. It was stirred at rt for 16 h, then diluted with more DCM and washed with cold saturated sodium bicarbonate, dried over sodium sulfate, filtered, concentrated and purified by column chromatography ($SiO_2$, 20-30% ethyl acetate/hexanes) to provide the desired 3-fluoroproline intermediate.

Method P: To a solution of the protected hydroxamate (0.65 mmol) in ethanol (25 ml) under a nitrogen atmosphere, 10%/wt of 10% $Pd(OH)_2$/C was added, and the reaction vessel was charged with hydrogen. The reaction was stirred for 8 h, filtered through a pad of Celite, and the filtrate concentrated to provide the desired final inhibitor.

Method Q: To a solution of the 3-hydroxyproline compound (4 g, 1 eq.) in DMF (50 ml), was added methyl iodide (5.3 ml, 5 eq.) and silver oxide (11.3 g, 3 eq.), and the reaction was stirred for 16 h. The reaction mixture was then diluted with ethyl acetate and filtered through Celite. The filtrate was washed with brine, 10% sodium thiosulfate, saturated sodium bicarbonate, and dried over sodium sulfate. The organic extracts were concentrated and purified by column chromatography ($SiO_2$, gradient 20-40% ethyl acetate/hexanes) to provide the desired intermediate.

Method R: HPLC analysis conditions are as follows. YMC-Pak Pro C18, S-3 µm, 120A, 50×4.6 mm I.D. Column; gradient eluent 0%-90% MeCN in water (both solvents containing 0.1% TFA) over 8.5 min, 1.5 mL/min.

Method S: The methyl ester (1 eq.) was taken into DCM and the reaction was cooled to 40° C. MCPBA (2 eq.) in DCM was added very slowly. The temperature of the reaction was maintained below −5° C. for 2 h during which the reaction was monitored for completion by TLC in hexanes/ethyl acetate (2:3). The reaction provided both the sulfone and the sulfoxide intermediates. Upon completion, excess DCM was added to the reaction mixture and washed with cold saturated sodium bicarbonate. The organic layer was dried over sodium sulfate, filtered and concentrated. The residue obtained was purified by column chromatography ($SiO_2$, hexanes/ethyl acetate and acetone/DCM) to afford the desired oxidized intermediate(s).

Method T: The methyl ester was taken into a mixture of THF-MeOH (1:1 volume by volume). 50% aq. hydroxylamine/water followed by catalytic amounts of potassium cyanide was then added to the reaction mixture. The reaction was allowed to stir at rt for 16 h. Solvents were removed under vacuum, and the residue was taken into water and the compound extracted into the ethyl acetate layer. The organic layer was dried over sodium sulfate, filtered, concentrated and purified by preparative HPLC to give the final inhibitor.

Method U: A solution of anhydrous DMSO (22.7 mL, 320 mmol) in anhydrous DCM (600 mL) is stirred at −78° C. under nitrogen. Oxalyl chloride (13.9 mL, 159 mmol) is slowly added at a rate to maintain a temperature below −65° C. The mixture is stirred for an additional 15 min, and alcohol (126 mmol) in DCM (125 mL) is added. After an additional 30 min of stirring, triethylamine (85.0 mL, 610 mmol) is added. The mixture is stirred while slowly warming to rt (ca. 80 min). This is diluted with DCM and washed with 10% citric acid solution. The DCM layer is separated, washed with brine, dried over sodium sulfate, and concentrated under vacuum. The crude product is purified by column chromatography ($SiO_2$, 30%-50% ethyl acetate in hexanes).

Method V: Ketone (1.08 mmol), Zn (566 mg, 8.66 mmol), bis(cyclopentadienyl)zirconium dichloride (380 mg, 1.30 mmol), and THF (2 mL are combined and stirred at rt under nitrogen. Dibromomethane (0.17 mL, 2.44 mmol) is slowly added to the mixture. The internal temperature slowly increased to ca. 30° C. The reaction mixture is stirred for 3 h, and is quenched with water. The solution is extracted twice with ether. The organic layers are combined, dried over sodium sulfate, and concentrated under vacuum. The crude material is purified by column chromatography ($SiO_2$, 30% ethyl acetate in hexanes).

Method W: Alkene (0.362 mmol), 4-methylmorpholine N-oxide (47 mg, 0.401 mmol), 2.5% $OsO_4$ in tert-butyl alcohol (t-BuOH) (0.46 mL, 0.037 mmol), acetone (4 mL), and water (0.25 mL) were combined and stirred at rt for 18 h. The reaction mixture was concentrated under vacuum. The crude product was purified by column chromatography (10% MeOH in DCM).

Method X: Alcohol (1.62 mmol), 2,6-di-tert-butyl-4-methylpyridine (664 mg, 3.23 mmole), and anhydrous DCM (10 mL) are combined and stirred at 4° C. Trimethyloxonium tetrafluoroborate (239 mg, 1.62 mmole) is added to the reaction mixture, and the combination mixture is stirred for 1 h at 4° C. The mixture is warmed to room temperature and allowed to stir for an additional 4 h. The mixture is diluted with DCM and washed with saturated, aqueous $NaHCO_3$ solution. The organic layer is dried over sodium sulfate, and concentrated under vacuum. The crude material is purified by column chromatography (3% MeOH in DCM).

Method Y: Methyl ester (0.921 mmol), lithium hydroxide monohydrate (50.8 mg, 1.21 mmol), water (10 mL), and MeOH (10 mL) are combined and stirred at reflux for 1 hour. The mixture is cooled, and acidified with 10% HCl to pH=1. The aqueous mixture is extracted with EtOAc, dried over sodium sulfate, and concentrated under vacuum. The crude product is used in the next reaction without further purification.

Method Z: An appropriate O-benzyl, N-benzyl or N-benzyl carbamate (0.311 mmol), 10% Pd on carbon (33 mg, 0.031 mmol), and EtOH (5 mL) are combined and stirred under $H_2$ at rt for 8 h. The mixture was filtered through Celite and concentrated in vacuo. The crude material is used in the next reaction without further purification, unless specifically stated.

Method AA: Tetrahydropyranyl protected alcohol or tert-butoxycarbonyl protecting group (Boc) protected amine (0.580 mmol) and 20% TFA in DCM (50 ml) is stirred at rt for 2 h. The reaction is concentrated in vacuo and used without further purification unless specifically stated.

Method BB: Methyl ester (54.63 mmol), NaOH (54.74 mmol), water (300 mL), and MeOH (300 mL) are combined and stirred at 4° C. for 18 h. The aqueous layer is washed with ether. The extracted aqueous layer is acidified to pH 1 with 1 N HCl. The acidic solution is extracted with ethyl acetate. The ethyl acetate layer is dried over sodium sulfate, concentrated in vacuo, and used in the next step without further purification.

Method CC: Alkene (1.14 mmol), MCPBA (77% max, 2.28 mmol), and DCM (50 mL) are combined and stirred at 4° C. The reaction is slowly warmed to rt, and then stirred at rt for and additional 18 h. The reaction mixture is concentrated in vacuo, and purified by column chromatography ($SiO_2$, 0-20% MeOH in DCM). Two separate diastereomeric epoxides are obtained.

Method DD: Epoxide (0.74 mmol), sodium azide (1.45 g, 22.26 mmol), DMF (10 mL), and water (2 mL) are combined and stirred at 80° C. for 18 h. Water is added to the reaction mixture, and the mixture is extracted with ethyl acetate. The ethyl acetate layer is washed with water and brine, dried over sodium sulfate, and concentrated in vacuo. The compound was used in the next reaction without further purification.

Method EE: 4-(4-n-Propylphenyl)benzoic acid (130 mg, 0.53 mmol), DCM (8 ml), DMF (1 drop), and oxalyl chloride (0.09 ml, 1.03 mmol) are combined and stirred at rt for 1 h. The reaction mixture is concentrated in vacuo, and the residue is redissolved in DCM (8 mL). The amine (0.47 mmol) is dissolved in pyridine and combined with the DCM mixture. The combined mixture is stirred at rt for 18 h, and diluted with ethyl acetate. The ethyl acetate solution is washed with water, dried over sodium sulfate, and concentrated in vacuo. The compound was used in the next reaction without further purification.

Method FF: To a stirred solution or suspension of the acid (1 mmol, 1 eq) in DCM (3-5 mL) was added few drops of DMF. The resulting solution was cooled to 0° C. in ice bath followed by addition of 2M $(COCl)_2$ in toluene (1 mL, 2 eq.). This mixture was stirred at 0° C. for 3 h, and solvents were removed under vacuum to yield relatively pure acid chloride. The residue was suspended in anhydrous THF (2-3 mL), and resulting suspension was cooled to 0° C. To this suspension was added amino acid (0.5 mmol) dissolved in 1N NaOH solution (1-2 mL). The resulting mixture was stirred at rt for 16 h followed by addition of 1N HCl to pH 3. The resulting mixture was extracted with EtOAc (3×10 mL). The combined organic phase was washed with saturated aq. $NaHCO_3$, brine, and dried over $Na_2SO_4$. Solvent was removed under vacuum to yield a mixture of the product along with starting acid as indicated by TLC and mass spectrometry (MS) analysis.

The above mixture was dissolved in MeOH (3-5 mL) followed by cooling to 0° C. To this mixture was added 2M solution of $TMSCHN_2$ in diethyl ether (4 ml, 8 eq.). This mixture was stirred at 0° C. for 10 min, and then for 20 min at rt. The yellow solution was concentrated under reduced pressure and purified by column chromatography to yield pure methyl ester.

Method GG: To a stirred solution of above ester (1 mmol) in MeOH (3-5 mL) was added a 50% aq. solution of $NH_2OH$ (1-2 mL). This mixture was stirred at rt for 30 min to 16 h, at which time the reaction was complete as detected by HPLC. The reaction was concentrated under reduced pressure and the resulting residue was suspended in MeOH/water to prepare a clear solution. This solution was then purified via preparative HPLC to yield the pure product.

Method HH: HPLC analysis conditions are as follows. YMC-Pak Pro C18, S-3 μm, 120A, 50×4.6 mm I.D. Column; gradient eluent 2%-98% MeCN in water (both solvents containing 0.1% TFA) over 5 min, 2.0 mL/min.

Method II: HPLC analysis conditions are as follows. YMC-Pak Pro C18, S-3 μm, 120A, 50×4.6 mm I.D. Column; gradient eluent 2%-98% MeCN in water (both solvents containing 0.1% TFA) over 6 min, 1.5 mL/min.

Example 1

Step 1: (2S,3S)-1-(tert-Butoxycarbonyl)-3-hydroxypyrrolidine-2-carboxylic acid was prepared from (2S,3S)-3-Hydroxypyrrolidine-2-carboxylic acid following Method A (yield=91%). The resulting product was used without purification. 1H NMR (DMSO-d6): 5.64-5.63 (d, 1H), 4.42 (bs, 1H), 4.13-4.10 (d, 1H), 3.64-3.48 (m, 2H), 2.11-1.99 (m, 2H), 1.58-1.52 (d, 9H). HPLC: Rt=3.868 min following Method R. ES–MS: calcd. for $C_{10}H_{17}NO_5$ (231.25). Found: 230.2 [M−H].

Step 2: (2S,3S)-1-tert-Butyl 2-methyl 3-hydroxypyrrolidine-1,2-dicarboxylate was prepared from (2S,3S)-1-(tert-butoxycarbonyl)-3-hydroxypyrrolidine-2-carboxylic acid following Method B (quantitative yield). 1H NMR ($CDCl_3$): 4.44-4.42 (m, 2H), 4.3-4.2 (d, 1H), 3.75 (s, 3H), 3.68-3.56 (m, 2H), 2.18-2.08 (m, 1H), 1.94-1.75 (m, 1H), 1.47-1.41 (d, 9H). HPLC: Rt=4.45 min following Method R. ES–MS: calcd. for $C_{11}H_{19}N_2O_6$ (245.13). Found 268.3 [M+Na].

Step 3: (2S,3S)-1-tert-Butyl 2-methyl 3-azidopyrrolidine-1,2-dicarboxylate was prepared from (2S,3S)-1-tert-butyl 2-methyl 3-hydroxypyrrolidine-1,2-dicarboxylate following Methods C, D and E (overall yield=90%). 1H NMR (DMSO-d6): 4.65-4.61 (m, 1H), 4.26-4.25 (d, J=2.73 Hz, 1H), 3.89-3.87 (d, J=7.41 Hz, 3H), 3.83-3.52 (m, 2H), 2.32-2.12 (m, 2H), 1.47-1.42 (d, J=20.6 Hz, 9H). HPLC: Rt=5.94 following Method R. ES–MS: calcd. for $C_{11}H_{18}N_4O_4$ (270.29). Found: 271.4 [M+H].

Step 4: (2S,3S)-Methyl 3-azidopyrrolidine-2-carboxylate hydrochloride salt was prepared from (2S,3S)-1-tert-butyl 2-methyl 3-azidopyrrolidine-1,2-dicarboxylate following Method F (quantitative yield). 1H NMR (DMSO-d6): 4.9-4.84 (m, 1H), 4.53-4.51 (d, J=5.77 Hz, 1H), 3.75 (s, 3H), 3.5-3.45 (t, J=7.42 Hz. 2H), 2.5-2.43 (dd, J=7.42 & 7.14 Hz, 1H), 2.13-2.06 (m, 1H). ES–MS: calcd. for $C_6H_{10}N_4O_2$ (170.29). Found: 171.2.

Step 5: (2S,3S)-Methyl 3-azido-1-(4'-propylbiphenylcarbonyl)pyrrolidine-2-carboxylate was prepared from (2S,3S)-methyl 3-azidopyrrolidine-2-carboxylate and 4-(p-n-propylphenyl)-benzoic acid following Method G (yield=75%). 1H NMR (DMSO-d6): 7.95-7.92 (d, J=8.24 Hz, 2H), 7.83-7.81 (d, J=7.97 Hz, 4H), 7.51-7.48 (d, J=7.97 Hz, 2H), 4.74-4.71 (m, 1H), 4.63-4.62 (d, J=3.3 Hz, 1H), 3.92 (s, 3H), 3.89-3.5 (m, 2H), 2.69-2.68 (t, J=1.65 & 1.92 Hz, 2H), 2.44-2.37 (m, 1H), 2.23-2.18 (m, 1H), 1.85-1.78 (m, 2H), 1.13-1.08 (t, J=3.42 Hz, 3H). HPLC: Rt=6.36 following Method R. ES–MS: calcd. for $C_{22}H_{24}N_4O_3$ (392.45). Found: 393.1 [M+H].

Step 6: (2S,3S)-3-Azido-N-hydroxy-1-(4'-propylbiphenylcarbonyl)pyrrolidine-2-carboxamide was prepared from (2S,3S)-methyl 3-azido-1-(4'-propylbiphenylcarbonyl)pyrrolidine-2-carboxylate following Method H (yield=25%). 1H NMR (DMSO-d6): 10.96 (bs, 1H), 9.06 (bs, 1H), 7.81-7.61 (m, 6H), 7.31-7.29 (d, J=7.97 Hz, 2H), 6.53 (bs, 1H), 4.36-4.1 (m, 1H), 3.67-3.57 (m, 2H), 2.62-2.57 (t, J=7.42 Hz, 2H), 2.26 (bs, 1H), 1.98 (bs, 1H), 1.65-1.58 (m, 2H), 0.93-0.88 (t, J=7.14 & 7.42 Hz, 3H). HPLC: Rt=6.36 following Method R. ES–MS: calcd. for $C_{21}H_{23}N_5O_3$ (393.45). Found: 416.2 [M+Na].

Example 2

Step 1: (2S,3S)-1-(tert-Butoxycarbonyl)-3-hydroxypyrrolidine-2-carboxylic acid was prepared from (2S,3S)-3-Hydroxypyrrolidine-2-carboxylic acid following Method A (yield=91%). The resulting product was used without purification. 1H NMR (DMSO-d6): 5.64-5.63 (d, 1H), 4.42 (bs, 1H), 4.13-4.1 (d, 1H), 3.64-3.48 (m, 2H), 2.11-1.99 (m, 2H), 1.58-1.52 (d, 9H). HPLC: Rt=3.868 min following Method R. ES–MS: calcd. for $C_{10}H_{17}NO_5$ (231.25). Found: 230.2 [M−H].

Step 2: (2S,3S)-1-tert-Butyl 2-methyl 3-hydroxypyrrolidine-1,2-dicarboxylate was prepared from (2S,3S)-1-(tert-butoxycarbonyl)-3-hydroxypyrrolidine-2-carboxylic acid following Method B (quantitative yield). 1H NMR ($CDCl_3$): 4.44-4.42 (m, 2H), 4.3-4.2 (d, 1H), 3.75 (s, 3H) 3.68-3.56 (m, 2H), 2.18-2.08 (m, 1H), 1.94-1.75 (m, 1H), 1.47-1.41 (d, 9H). HPLC: Rt=4.45 min following Method R. ES–MS: calcd. for $C_{11}H_{19}N_2O_5$ (245.13). Found: 268.3 [M+Na].

Step 3: (2S,3S)-1-tert-Butyl 2-methyl 3-azidopyrrolidine-1,2-dicarboxylate was prepared from (2S,3S)-1-tert-butyl 2-methyl 3-hydroxypyrrolidine-1,2-dicarboxylate following Methods C, D and E (overall yield=90%). 1H NMR (DMSO-d6): 4.65-4.61 (m, 1H), 4.26-4.25 (d, J=2.73 Hz, 1H), 3.89-3.87 (d, J=7.41 Hz, 3H), 3.83-3.52 (m, 2H), 2.32-2.12 (m, 2H), 1.47-1.42 (d, J=20.6 Hz, 9H). HPLC: Rt=5.94 min following Method R. ES–MS: calcd. for $C_{11}H_{18}N_4O_4$ (270.29). Found: 271.4 [M+H].

Step 4: (2S,3S)-Bethyl 3-azidopyrrolidine-2-carboxylate hydrochloride salt was prepared from (2S,3S)-1-tert-butyl 2-methyl 3-azidopyrrolidine-1,2-dicarboxylate following Method F (quantitative yield). 1H NMR (DMSO-d6): 4.9-4.84 (m, 1H), 4.53-4.51 (d, J=5.77 Hz, 1H), 3.75 (s, 3H), 3.5-3.45 (t, J=7.42 Hz. 2H), 2.5-2.43 (dd, J=7.42 & 7.14 Hz, 1H), 2.13-2.06 (m, 1H). ES–MS: calcd. for $C_5H_{10}N_4O_2$ (170.29). Found: 171.2

Step 5: (2S,3S)-Methyl 3-azido-1-(4'-propylbiphenylcarbonyl)pyrrolidine-2-carboxylate was prepared from (2S,3S)-methyl 3-azidopyrrolidine-2-carboxylate and 4-(p-n-propylphenyl)-benzoic acid following Method G (yield=75%). 1H NMR (DMSO-d6): 7.95-7.92 (d, J=8.24 Hz, 2H), 7.83-7.81 (d, J=7.97 Hz, 4H), 7.51-7.48 (d, J=7.97 Hz, 2H), 4.74-4.71 (m, 1H), 4.63-4.62 (d, J=3.3 Hz, 1H), 3.92 (s, 3H), 3.89-3.5 (m, 2H), 2.69-2.68 (t, J=1.65 & 1.92 Hz, 2H), 2.44-2.37 (m, 1H), 2.23-2.18 (m, 1H), 1.85-1.78 (m, 2H), 1.13-1.08 (t, J=3.42 Hz, 3H). HPLC: Rt=7.19 min following Method R ES–MS: calcd. for $C_{22}H_{24}N_4O_3$ (392.45). Found: 393.1 [M+H].

Step 6: (2S,3S)-3-Mzido-N-(benzyloxy)-1-(4'-propylbiphenylcarbonyl)pyrrolidine-2-carboxamide was prepared from (2S,3S)-methyl 3-azido-1-(4'-propylbiphenylcarbonyl) pyrrolidine-2-carboxylate following Method I (yield=89%).

1H NMR (DMSO-d6): 11.79 (bs, 1H), 7.95-7.76 (m, 5H), 7.63-7.48 (m, 8H), 5.02 (bs, 1H), 4.51 (bs, 2H), 4.44-4.28 (m, 1H), 3.92 (s, 3H), 3.86-3.77 (m, 2H), 2.82-2.77 (t, J=7.14 & 7.97 Hz, 2H), 2.4 (bs, 1H), 2.16 (bs, 1H), 1.88-1.75 (m, 2H), 1.13-1.08 (t, J=7.42 & 7.14 Hz, 3H). HPLC: Rt=7.19 min following Method R. ES–MS: calcd. for $C_{28}H_{29}N_5O_3$ (483.56). Found: 484.1 [M+H].

Step 7: (2S,3S)-3-Amino-N-hydroxy-1-(4'-propylbiphenylcarbonyl)pyrrolidine-2-carboxamide was prepared from (2S,3S)-3-azido-N-(benzyloxy)-1-(4'-propylbiphenylcarbonyl)pyrrolidine-2-carboxamide following Method J (yield=30-40%). 1H NMR (DMSO-d6): 11.1 (bs, 1H), 9.312 (bs, 1H), 8.52 (bs, 2H), 7.96-7.82 (m, 6H), 7.52-7.5 (d, J=8.24 Hz, 2H), 4.79 (bs, 1H), 4.05 (bs, 1H), 3.91-3.85 (m, 2H), 2.82-2.77 (t, J=7.69 & 7.42 Hz, 2H), 2.48 (m, 1H), 2.23 (bs, 1H), 1.85-1.75 (m, 2), 1.13-1.08 (t, J=7.42 & 7.14 Hz, 3H). HPLC: Rt=5.12 min following Method R. ES–MS: calcd. for $C_{21}H_{25}N_3O_3$ (367.45). Found: 368.3 [M+H].

Example 3

Step 1: (2S,3S)-1-(tert-Butoxycarbonyl)-3-hydroxypyrrolidine-2-carboxylic acid was prepared from (2S,3S)-3-Hydroxypyrrolidine-2-carboxylic acid following Method A (yield=91%). The resulting product was used without purification. 1H NMR (DMSO-d6): 5.64-5.63 (d, 1H), 4.42 (bs, 1H), 4.13-4.1 (d, 1H), 3.64-3.48 (m, 2H), 2.11-1.99 (m, 2H), 1.58-1.52 (d, 9H). HPLC: Rt=3.868 min following Method R. ES–MS: calcd. for $C_{10}H_{17}NO_5$ (231.25). Found: 230.2 [M–H].

Step 2: (2S,3S)-1-tert-Butyl 2-methyl 3-hydroxypyrrolidine-1,2-dicarboxylate was prepared from (2S,3S)-1-(tert-butoxycarbonyl)-3-hydroxypyrrolidine-2-carboxylic acid following Method B (quantitative yield). 1H NMR (CDCl$_3$): 4.44-4.42 (m, 2H), 4.3-4.2 (d, 1H), 3.75 (s, 3H), 3.68-3.56 (m, 2H), 2.18-2.08 (m, 1H), 1.94-1.75 (m, 1H), 1.47-1.41 (d, 9H). HPLC: Rt=4.45 min following Method R. ES–MS: calcd. for $C_{11}H_{19}NO_5$ (245.13). Found 268.3 [M+Na].

Step 3: (2S,3S)-1-tert-Butyl 2-methyl 3-azidopyrrolidine-1,2-dicarboxylate was prepare from (2S,3S)-1-tert-butyl 2-methyl 3-hydroxypyrrolidine-1,2-dicarboxylate following Methods C, D and E (overall yield=90%). 1H NMR (DMSO-d6): 4.65-4.61 (m, 1H), 4.26-4.25 (d, J=2.73 Hz, 1H), 3.89-3.87 (q, J=7.41 Hz, 3H), 3.83-3.52 (m, 2H), 2.32-2.12 (m, 2H), 1.47-1.42 (d, J=20.6 Hz, 9H). HPLC: Rt=5.94 min following Method R. ES–MS: calcd. for $C_{11}H_{18}N_4O_4$ (270.29). Found: 271.4 [M+H].

Step 4: (2S,3S)-Methyl 3-azidopyrrolidine-2-carboxylate hydrochloride salt was prepared from (2S,3S)-1-tert-butyl 2-methyl 3-azidopyrrolidine-1,2-dicarboxylate following Method F (quantitative yield). 1H NMR (DMSO-d6): 4.9-4.84 (m, 1H), 4.53-4.51 (d, J=5.77 Hz, 1H), 3.75 (s, 3H), 3.5-3.45 (t, J=7.42 Hz. 2H), 2.5-2.43 (dd, J=7.42 & 7.14 Hz, 1H), 2.13-2.06 (m, 1H). ES–MS: calcd. for $C_6H_{10}N_4O_2$ (170.29). Found: 171.2

Step 5: (2S,3S)-Methyl 3-azido-1-(4'-propylbiphenylcarbonyl)pyrrolidine-2-carboxylate was prepared from (2S,3S)-methyl 3-azidopyrrolidine-2-carboxylate and 4-(p-n-propylphenyl)-benzoic acid following Method G (yield=75%). 1H NMR (DMSO-d6): 7.95-7.92 (d, J=8.24 Hz, 2H), 7.83-7.81 (d, J=7.97 Hz, 4H), 7.51-7.48 (d, J=7.97 Hz, 2H), 4.74-4.71 (m, 1H), 4.63-4.62 (d, J=3.3 Hz, 1H), 3.92 (s, 3H), 3.89-3.5 (m, 2H), 2.69-2.68 (t, J=1.65 & 1.92 Hz, 2H), 2.44-2.37 (m, 1H), 2.23-2.18 (m, 1H), 1.85-1.78 (m, 2H), 1.13-1.08 (t, J=3.42 Hz, 3H). HPLC: Rt=7.19 min following Method R. ES–MS: calcd. for $C_{22}H_{24}N_4O_3$ (392.45). Found: 393.1 [M+H].

Step 6: (2S,3S)-Methyl-3-amino-1-(4'-propylbiphenylcarbonyl)pyrrolidine-2-carboxylate was prepared from (2S,3S)-methyl 3-azido-1-(4'-propylbiphenylcarbonyl)pyrrolidine-2-carboxylate following Method K (quantitative yield). 1H NMR (DMSO-d6): 7.74-7.60 (m, 7H), 7.38-7.29 (m, 3H), 4.15-4.13 (d, J=4.12 Hz, 1H), 3.72-3.46 (m, 3H), 3.68-3.67 (d, J=1.37 Hz, 3H), 2.62-2.57 (t, J=7.42 Hz, 2H), 2.1-1.97 (m, 2H), 1.7-1.58 (m, 2H), 0.93-0.88 (t, J=7.14 & 7.42 Hz, 3H). HPLC: Rt=5.48 min following Method R. ES–MS: calcd. for $C_{22}H_{24}N_4O_3$ (366). Found: 367.2 [M+H].

Step 7: (2S,3S)-Methyl-3-(methylsulfonamido)-1-(4'propylbiphenylcarbonyl)pyrrolidine-2-carboxylate was prepared from (2S,3S)-methyl-3-amino-1-(4'propylbiphenylcarbonyl)pyrrolidine-2-carboxylate following Method L (yield=67%). 1H NMR (DMSO-d6): 7.82-7.60 (m, 6H), 7.38-7.36 (d, J=8.24 Hz, 1H), 7.32-7.29 (d, J=7.97 Hz, 2H), 4.37-4.35 (d, J=4.7 Hz, 1H), 4.08-4.01 (t, J=6.04 & 7.69 Hz, 1H), 4.01-3.62 (m, 2H), 3.69 (bs, 3H), 2.99 (bs, 3H), 2.5-2.49 (t, J=1.92 & 1.65 Hz, 2H), 2.2-2.16 (dd, J=6.04-6.59 Hz, 1H), 1.98-1.87 (m, 2H), 1.68-1.5 (m, 2H), 0.93-0.84 (t, J=7.14 & 7.42 Hz, 3H). HPLC: Rt=6.47 min following Method R. ES–MS: calcd. for $C_{23}H_{28}N_2O_5S$ (444.54). Found: 445.2 [M+H].

Step 8: (2S,3S)—N-Hydroxy-3-(methylsulfonamido)-1-(4'-propylbiphenylcarbonyl)pyrrolidine-2-carboxamide was prepared from (2S,3S)-methyl-3-(methylsulfonamido)-1-(4'-propylbiphenylcarbonyl)pyrrolidine-2-carboxylate following Method H (yield=40%). 1H NMR (DMSO-d6): 11.06 (bs, 1H), 7.94-7.80 (m, 7H), 7.62-7.6 (d, J=7.69 Hz, 1H), 7.50-7.48 (d, J=8.24 Hz, 2H), 4.45-4.44 (m, 1H), 4.45-4.44 (d, J=3.84 Hz, 1H), 4.13-4.11 (d, J=4.67 Hz, 1H), 3.83-3.78 (t, J=6.59 & 6.86 Hz, 2H), 3.17 (bs, 3H), 2.81-2.76 (t, J=7.42 & 7.69 Hz, 2H), 2.45-2.39 (m, 1H), 2.06-1.74 (m, 2H), 1.12-1.07 (t, J=7.14 & 7.42 Hz, 3H). HPLC: Rt=6.47 min following Method R. ES–MS calcd. for $C_{22}H_{27}N_3O_5S$ (445.54). Found: 446.3 [M+H].

Example 4

Step 1: (2S,3S)-1-(tert-Butoxycarbonyl)-3-hydroxypyrrolidine-2-carboxylic acid was prepared from (2S,3S)-3-hydroxypyrrolidine-2-carboxylic acid following Method A (yield=91%). The resulting product was used without purification. 1H NMR (DMSO-d6): 5.64-5.63 (d, 1H), 4.42 (bs, 1H), 4.13-4.1 (d, 1H), 3.64-3.48 (m, 2H), 2.11-1.99 (m, 2H), 1.58-1.52 (d, 9H). HPLC: Rt=3.868 min following Method R. ES–MS: calcd. for $C_{10}H_{17}NO_5$ (231.25). Found: 230.2 [M–H].

Step 2: (2S,3S)-1-tert-Butyl 2-methyl 3-hydroxypyrrolidine-1,2-dicarboxylate was prepared from (2S,3S)-1-(tert-butoxycarbonyl)-3-hydroxypyrrolidine-2-carboxylic acid following Method B (quantitative yield). 1H NMR (CDCl$_3$): 4.44-4.42 (m, 2H), 4.3-4.2 (d, 1H), 3.75 (s, 3H), 3.68-3.56 (m, 2H), 2.18-2.08 (m, 1H), 1.94-1.75 (m, 1H), 1.47-1.41 (d, 9H). HPLC: Rt=4.45 min following Method R. ES-MS: calcd. for $C_{11}H_{19}NO_5$ (245.13). Found: 268.3 [M+Na].

Step 3: (2S,3S)-1-tert-Butyl 2-methyl 3-azidopyrrolidine-1,2-dicarboxylate was prepared from (2S,3S)-1-tert-butyl 2-methyl 3-hydroxypyrrolidine-1,2-dicarboxylate following Methods C, D and E (overall yield=90%). 1H NMR (DMSO-d6): 4.65-4.61 (m, 1H), 4.26-4.25 (d, J=2.73 Hz, 1H), 3.89-3.87 J=7.41 Hz, 3H), 3.83-3.52 (m, 2H), 2.32-2.12 (m, 2H), 1.47-1.42 (d, J=20.6 Hz, 9H). HPLC: Rt=5.94 min following Method R. ES-MS: calcd. for $C_{11}H_{18}N_4O_4$ (270.29). Found: 271.4 [M+H].

Step 4: (2S,3S)-Methyl 3-azidopyrrolidine-2-carboxylate hydrochloride salt was prepared from (2S,3S)-1-tert-butyl 2-methyl 3-azidopyrrolidine-1,2-dicarboxylate following Method F (quantitative yield) 1H NMR (DMSO-d6): 4.9-4.84 (m, 1H), 4.53-4.51 (d, J=5.77 Hz, 1H), 3.75 (s, 3H), 3.5-3.45 (t, J=7.42 Hz. 2H), 2.5-2.43 (dd, J=7.42 & 7.14 Hz, 1H), 2.13-2.06 (m, 1H). ES–MS: calcd. for $C_6H_{10}N_4O2$ (170.29). Found: 171.2.

Step 5: (2S,3S)-Methyl 3-azido-1-(4'-propylbiphenylcarbonyl)pyrrolidine-2-carboxylate was prepared from (2S,3S)-methyl 3-azidopyrrolidine-2-carboxylate and 4-(p-n-propylphenyl)-benzoic acid following Method G (yield=75%). 1H NMR (DMSO-d6): 7.95-7.92 (d, J=8.24 Hz, 2H), 7.83-7.81 (d, J=7.97 Hz, 4H), 7.51-7.48 (d, J=7.97 Hz, 2H), 4.74-4.71 (m, 1H), 4.63-4.62 (d, J=3.3 Hz, 1H), 3.92 (s, 3H), 3.89-3.5 (m, 2H), 2.69-2.68 (t, J=1.65 & 1.92 Hz, 2H), 2.44-2.37 (m, 1H), 2.23-2.18 (m, 1H), 1.85-1.78 (m, 2H), 1.13-1.08 (t, J=3.42 Hz, 3H). HPLC: Rt=7.19 min following ES–MS: calcd. for $C_{22}H_{24}N_4O_3$ (392.45). Found: 393.1 [M+H].

Step 6: (2S,3S)-Methyl-3-amino-1-(4'-propylbiphenylcarbonyl)pyrrolidine-2-carboxylate was prepared from (2S,3S)-methyl 3-azido-1-(4'-propylbiphenylcarbonyl)pyrrolidine-2-carboxylate following Method K (quantitative yield). 1H NMR (DMSO-d6): 7.74-7.60 (m, 7H), 7.38-7.29 (m, 3H), 4.15-4.13 (d, J=4.12 Hz, 1H), 3.72-3.46 (m, 3H), 3.68-3.67 (d, J=1.37 Hz, 3H), 2.62-2.57 (t, J=7.42 Hz, 2H), 2.1-1.97 (m, 2H), 1.7-1.58 (m, 2H), 0.93-0.88 (t, J=7.14 & 7.42 Hz, 3H). HPLC: Rt=5.48 min following Method R. ES–MS: calcd. for $C_{22}H_{24}N_4O_3$ (366). Found: 367.2 [M+H].

Step 7: (2S,3S)-Methyl-3-formamido-1-(4'-propylbiphenylcarbonyl)pyrrolidine-2-carboxylate was prepared from (2S,3S)-methyl-3-amino-1-(4'-propylbiphenylcarbonyl)pyrrolidine-2-carboxylate following Method M (yield=80%). 1H NMR (DMSO-d6): 8.82-8.8 (d, J=7.42 Hz, 2H), 8.27 (bs, 1H), 7.96-7.93 (d, J=7.69 Hz, 2H), 7.84-7.81 (d, J=8.24 Hz, 4H), 7.51-7.49 (d, J=7.42 Hz, 2H), 4.7-4.63 (dd, J=6.59 & 6.32 Hz, 1H), 4.48-4.46 (d, J=5.22 Hz, 1H), 3.863-3.86 (d, J=1.098 Hz, 3H), 3.88-3.67 (m, 2H), 2.82-2.77 (t, J=7.97 & 7.42 Hz, 2H), 2.34-2.28 (dd, J=6.87 & 6.59 Hz, 1H), 2.1-2.03 (dd, J=6.87 & 5.77 Hz, 1H), 1.88-1.75 (m, 2H), 1.13-1.08 (t, J=7.42 & 7.14 Hz, 3H). HPLC: Rt=6.25 min following Method R. ES–MS: calcd. for $C_{23}H_{26}N_2O_4$ (394.16). Found: 417.3 [M+Na].

Step 8: (2S,3S)-3-Formamido-N-hydroxy-1-(4'-propylbiphenylcarbonyl)pyrrolidine-2-carboxamide was prepared from (2S,3S)-methyl-3-formamido-1-(4'-propylbiphenylcarbonyl)pyrrolidine-2-carboxylate following Method H (yield=33%). 1H NMR (DMSO-d6): 10.97 (bs, 1H), 8.76-8.74 (d, J=7.14 Hz, 1H), 8.22 (bs, 1H), 7.94-7.81 (m, 6H), 7.61-7.58 (d, J=7.42 Hz, 1H), 7.51-7.48 (d, J=7.97 Hz, 2H), 4.56 (bs, 1H), 4.42 (bs, 1H), 3.82-3.77 (m, 2H), 2.36-2.32 (m, 1H), 2.81-2.76 (t, J=7.69 Hz, 2H), 2.1-2.03 (dd, J=6.87 & 5.77 Hz, 1H), 1.96-1.94 (m, 1H), 1.87-1.77 (m, 2H), 1.12-1.07 (t, J=7.42 Hz, 3H). HPLC: Rt=5.64 min following Method R. ES–MS: calcd. for $C_{22}H_{25}N_3O_4$ (395.46). Found: 396.3 [M+H].

Example 5

Step 1: (2S,3S)-1-(tert-Butoxycarbonyl)-3-hydroxypyrrolidine-2-carboxylic acid was prepared from (2S,3S)-3-Hydroxypyrrolidine-2-carboxylic acid following Method A (yield=91%). The resulting product was used without purification. 1H NMR (DMSO-d6): 5.64-5.63 (d, 1H), 4.42 (bs, 1H), 4.13-4.1 (d, 1H), 3.64-3.48 (m, 2H), 2.11-1.99 (m, 2H), 1.58-1.52 (d, 9H). HPLC: Rt=3.868 min following Method R. ES–MS: calcd. for $C_{10}H_{17}NO_5$ (231.25). Found: 230.2 [M−H].

Step 2: (2S,3S)-1-tert-Butyl 2-methyl 3-hydroxypyrrolidine-1,2-dicarboxylate was prepared from (2S,3S)-1-(tert-butoxycarbonyl)-3-hydroxypyrrolidine-2-carboxylic acid following Method B (quantitative yield). 1H NMR (CDCl₃): 4.44-4.42 (m, 2H), 4.3-4.2 (d, 1H), 3.75 (s, 3H), 3.68-3.56 (m, 2H), 2.18-2.08 (m, 1H), 1.94-1.75 (m, 1H), 1.47-1.41 (d, 9H). HPLC: Rt=4.45 min following Method R. ES–MS: calcd. for $C_{11}H_{19}N_2O_5$ (245.13). Found: 268.3 [M+Na].

Step 3: (2S,3S)-1-tert-Butyl 2-methyl 3-azidopyrrolidine-1,2-dicarboxylate was prepared from (2S,3S)-1-tert-butyl 2-methyl 3-hydroxypyrrolidine-1,2-dicarboxylate following Methods C, D and E (overall yield=90%). 1H NMR (DMSO-d6): 4.65-4.61 (m, 1H), 4.26-4.25 (d, J=2.73 Hz, 1H), 3.89-3.87 (d, J=7.41 Hz, 3H), 3.83-3.52 (m, 2H), 2.32-2.12 (m, 2H), 1.47-1.42 (d, J=20.6 Hz, 9H). HPLC: Rt=5.94 min following Method R. ES–MS: calcd. for $C_{11}H_{18}N_4O_4$ (270.29). Found: 271.4 [M+H].

Step 4: (2S,3S)-Methyl 3-azidopyrrolidine-2-carboxylate hydrochloride salt was prepared from (2S,3S)-1-tert-butyl 2-methyl 3-azidopyrrolidine-1,2-dicarboxylate following Method F (quantitative yield). 1H NMR (DMSO-d6): 4.9-4.84 (m, 1H), 4.53-4.51 (d, J=5.77 Hz, 1H), 3.75 (s, 3H), 3.5-3.45 (t, J=7.42 Hz. 2H), 2.5-2.43 (dd, J=7.42 & 7.14 Hz, 1H), 2.13-2.06 (m, 1H). ES–MS: calcd. for $C_6H_{10}N_4O_2$ (170.29). Found: 171.2.

Step 5: (2S,3S)-Methyl 3-azido-1-(4'-propylbiphenylcarbonyl)pyrrolidine-2-carboxylate was prepared from (2S,3S)-methyl 3-azidopyrrolidine-2-carboxylate and 4-(p-n-propylphenyl)-benzoic acid following Method G (yield=75%). 1H NMR (DMSO-d6): 7.95-7.92 (d, J=8.24 Hz, 2H), 7.83-7.81 (d, J=7.97 Hz, 4H), 7.51-7.48 (d, J=7.97 Hz, 2H), 4.74-4.71 (m, 1H), 4.63-4.62 (d, J=3.3 Hz, 1H), 3.92 (s, 3H), 3.89-3.5 (m, 2H), 2.69-2.68 (t, J=1.65 & 1.92 Hz, 2H), 2.44-2.37 (m, 1H), 2.23-2.18 (m, 1H), 1.85-1.78 (m, 2H), 1.13-1.08 (t, J=3.42 Hz, 3H). HPLC: Rt=7.19 min following Method R. ES–MS: calcd. for $C_{22}H_{24}N_4O_3$ (392.45). Found: 393.1 [M+H].

Step 6: (2S,3S)-Methyl-3-amino-1-(4'-propylbiphenylcarbonyl)pyrrolidine-2-carboxylate was prepared from (2S,3S)-methyl 3-azido-1-(4'-propylbiphenylcarbonyl)pyrrolidine-2-carboxylate following Method K (quantitative yield). 1H NMR (DMSO-d6): 7.74-7.60 (m, 7H), 7.38-7.29 (m, 3H), 4.15-4.13 (d, J=4.12 Hz, 1H), 3.72-3.46 (m, 3H), 3.68-3.67 (d, J=1.37 Hz, 3H), 2.62-2.57 (t, J=7.42 Hz, 2H), 2.1-1.97 (m, 2H), 1.7-1.58 (m, 2H), 0.93-0.88 (t, J=7.14 & 7.42 Hz, 3H). HPLC: Rt=5.48 min following Method R. ES–MS: calcd. for $C_{22}H_{24}N_4O_3$ (366). Found: 367.2 [M+H].

Step 7: (2S,3S)-Methyl-3-formamido-1-(4'-propylbiphenylcarbonyl)pyrrolidine-2-carboxylate was prepared from (2S,3S)-methyl-3-amino-1-(4'-propylbiphenylcarbonyl)pyrrolidine-2-carboxylate following Method M (yield=80%). 1H NMR (DMSO-d6): 8.82-8.8 (d, J=7.42 Hz, 2H), 8.27 (bs, 1H), 7.96-7.93 (d, J=7.69 Hz, 2H), 7.84-7.81 (d, J=8.24 Hz, 4H), 7.51-7.49 (d, J=7.42 Hz, 2H), 4.7-4.63 (dd, J=6.59 & 6.32 Hz, 1H), 4.48-4.46 (d, J=5.22 Hz, 1H), 3.863-3.86 (d, J−1.098 Hz, 3H), 3.88-3.67 (m, 2H), 2.82-2.77 (t, J=7.97 & 7.42 Hz, 2H), 2.34-2.28 (dd, J=6.87 & 6.59 Hz, 1H), 2.1-2.03 (dd, J=6.87 & 5.77 Hz, 1H), 1.88-1.75 (m, 2H), 1.13-1.08 (t, J=7.42 & 7.14 Hz, 3H). HPLC: Rt=6.25 min following Method R. ES–MS: calcd. for $C_{23}H_{26}N_2O_4$ (394.16). Found: 417.3 [M+Na].

Step 8: (2S,3S)-Methyl-3-(methylamino)-1-(4'-propylbiphenylcarbonyl)pyrrolidine-2-carboxylate was prepared from (2S,3S)-methyl-3-formamido-1-(4'-propylbiphenylcarbonyl)pyrrolidine-2-carboxylate following Method N (yield=59%). 1H NMR (DMSO-d6): 7.74-7.71 (d, J=8.24 Hz, 2H), 7.63-7.58 (dd, J=6.59 & 6.87 Hz, 4H), 7.31-7.28 (d, J=7.97 Hz, 2H), 5.78-5.74 (m, 1H), 4.32-4.31 (d, J=3.02 Hz, 1H), 3.72-3.58 (m, 1H), 3.68 (bs, 3H), 3.57-3.5 (m, 1H), 3.2-3.15 (t, J=6.04 & 5.22 Hz, 1H), 2.62-2.56 (t, J=7.42 & 7.69 Hz, 2H), 2.05-1.97 (m, 1H), 1.81-1.77 (m, 1H), 1.68-1.55 (m, 2H), 0.93-0.88 (t, J=7.14 & 7.42 Hz, 3H). HPLC: Rt=5.55 min following Method R. ES–MS: calcd. for $C_{23}H_{28}N_2O_3$ (380.21). Found: 381.2 [M+H].

Step 9: (2S,3S)—N-Hydroxy-3-(methylamino)-1-(4'-propylbiphenylcarbonyl)pyrrolidine-2-carboxamide was prepared from (2S,3S)-methyl-3-(methylamino)-1-(4'-propylbiphenylcarbonyl)pyrrolidine-2-carboxylate following Method H (yield=20%). 1H NMR (DMSO-d6): 11.19 (bs, 1H), 9.36-9.25 (m, 2H), 7.95-7.81 (m, 5H), 7.51-7.48 (d, J=8.24 Hz, 2H), 4.88 (bs, 1H), 4.0-3.85 (m, 3H), 2.88 (s, 3H), 2.81-2.76 (t, J=7.14 & 7.97 Hz, 2H), 2.5-2.34 (m, 2H), 1.87-1.75 (m, 2H), 1.13-1.08 (t, J=7.14 & 7.42 Hz, 3H). HPLC: Rt=5.187 min following Method R. ES–MS: calcd. for $C_{22}H_{27}N_3O_3$ (381.476). Found: 382.3 [M+H].

Example 6

Step 1: (2S,3S)-1-(tert-Butoxycarbonyl)-3-hydroxypyrrolidine-2-carboxylic acid was prepared from (2S,3S)-3-Hydroxypyrrolidine-2-carboxylic acid following Method A (yield=91%). The resulting product was used without purification. 1H NMR (DMSO-d6): 5.64-5.63 (d, 1H), 4.42 (bs, 1H), 4.13-4.1 (d, 1H), 3.64-3.48 (m, 2H), 2.11-1.99 (m, 2H), 1.58-1.52 (d, 9H). HPLC: Rt=3.868 min following Method R. ES–MS: calcd. for $C_{10}H_{17}NO_5$ (231.25). Found: 230.2 [M–H].

Step 2: (2S,3S)-1-tert-Butyl 2-methyl 3-hydroxypyrrolidine-1,2-dicarboxylate was prepared from (2S,3S)-1-(tert-butoxycarbonyl)-3-hydroxypyrrolidine-2-carboxylic acid following Method B (quantitative yield). 1H NMR (DMSO-d6): 4.44-4.42 (m, 2H), 4.3-4.2 (d, 1H), 3.75 (s, 3H), 3.68-3.56 (m, 2H), 2.18-2.08 (m, 1H), 1.94-1.75 (m, 1H), 1.47-1.41 (d, 9H). HPLC: Rt=4.45 min following Method R. ES–MS: calcd. for $C_{11}H_{19}N_2O_5$ (245.13). Found: 268.3 [M+Na].

Step 3: (2S,3R)-1-tert-Butyl 2-methyl 3-hydroxypyrrolidine-1,2-dicarboxylate was prepared from (2S,3S)-1-tert-butyl 2-methyl 3-hydroxypyrrolidine-1,2-dicarboxylate following Methods C and D (overall yield=90%). 1H NMR (DMSO-d6): 4.65-4.61 (m, 1H), 4.26-4.25 (d, J=2.73 Hz, 1H), 3.89-3.87 (d, J=7.41 Hz, 3H), 3.83-3.52 (m, 2H), 2.32-2.12 (m, 2H), 1.47-1.42 (d, J=20.6 Hz, 9H). HPLC: Rt=5.94 min following Method R. ES–MS: calcd. for $C_{11}H_{18}N_4O_4$ (270.29). Found: 271.4 [M+H].

Step 4: (2S,3S)-1-tert-Butyl 2-methyl 3-fluoropyrrolidine-1,2-dicarboxylate was prepared from (2S,3R)-1-tert-butyl 2-methyl 3-hydroxypyrrolidine-1,2-dicarboxylate following Method O (yield=46%). 1H NMR (DMSO-d6): 5.74-5.23 (m, 1H), 4.4-4.3 (dd, J=22.52 & 23.08 Hz, 1H), 3.69 (s, 3H), 3.66-3.31 (m, 2H), 2.15-1.93 (m, 2H), 1.4-1.33 (d, J=21.42 Hz, 9H). HPLC: Rt=5 min following Method R. ES–MS: calcd. for $C_{11}H_{18}FNO_4$ (247.26).

Step 5: (2S,3S)-Methyl 3-fluoropyrrolidine-2-carboxylate hydrochloride salt was prepared from (2S,3S)-1-tert-butyl 2-methyl 3-fluoropyrrolidine-1,2-dicarboxylate following Method F (quantitative yield). 1H NMR (DMSO-d6): 5.86-5.68 (dd, J=1.65 & 2.74 Hz, 1H), 4.93-4.85 (d, J=22.8 Hz, 1H), 3.98 (s, 3H), 3.68-3.49 (m, 2H), 2.49-2.3 (m, 2H). ES–MS: calcd. for $C_6H_{10}FNO_2$ (147.15). Found 148.2 [M+H].

Step 6: (2S,3S)-Methyl 3-fluoro-1-(4'-propylbiphenylcarbonyl)pyrrolidine-2-carboxylate was prepared from (2S,3S)-methyl 3-fluoropyrrolidine-2-carboxylate hydrochloride salt and 4-(p-n-propylphenyl)-benzoic acid following Method G (yield=78%). 1H NMR (DMSO-d6): 7.75-7.72 (d, J=8.24 Hz, 2H), 7.66-7.61 (d, J=6.32 & 5.77 Hz, 4H), 7.31-7.29 (d, J=7.97 Hz, 2H), 5.52-5.34 (d, J=52.47 Hz, 1H), 4.74-4.66 (d, J=22.53 Hz, 1H), 3.72 (s, 3H), 3.83-3.34 (m, 2H), 2.62-2.56 (t, J=7.69 Hz, 2H), 2.24-2.06 (m, 2H), 1.67-1.55 (m, 2H), 0.93-0.88 (t, J=7.14 & 7.42 Hz, 3H).

HPLC: Rt=7.10 min following Method R. ES–MS: calcd. for $C_{22}H_{24}FNO_3$ (369.17). Found: 370 [M+H].

Step 7: (2S,3S)—N-(Benzyloxy)-3-fluoro-1-(4'-propylbiphenylcarbonyl)pyrrolidine-2-carboxamide was prepared from (2S,3S)-methyl 3-fluoro-1-(4'-propylbiphenylcarbonyl)pyrrolidine-2-carboxylate following Method I (yield=60%). 1H NMR (DMSO-d6): 11.82 (bs, 1H), 7.95-7.77 (m, 6H), 7.66-7.49 (m, 7H), 5.45-5.28 (d, J=52.74 Hz, 1H), 5.03 (bs, 1H), 4.81-4.74 (m, 2H), 3.9-3.89 (d, J=5.77 Hz, 2H), 2.82-2.77 (t, J=7.69 & 7.42 Hz, 2H), 2.41-2.32 (m, 2H), 1.85-1.78 (m, 2H), 1.13-1.09 (t, J=5.77 & 7.14 Hz, 3H). HPLC: Rt=7.06 min following Method R. ES–MS: calcd. for $C_{28}H_{29}FN_2O_3$ (460.54).

Step 8: (2S,3S)-3-Fluoro-N-hydroxy-1-(4'-propylbiphenylcarbonyl)pyrrolidine-2-carboxamide was prepared from (2S,3S)—N-(benzyloxy)-3-fluoro-1-(4'-propylbiphenylcarbonyl)pyrrolidine-2-carboxamide following Method P (yield=25%). 1H NMR (DMSO-d6): 11.2 (bs, 1H), 7.94-7.81 (m, 6H), 7.6-7.57 (d, J=6.87 Hz, 1H), 7.51-7.48 (d, J=8.24 Hz, 2H), 5.49-5.32 (d, J=52.2 Hz, 1H), 4.87-4.8 (d, J=22.53 Hz, 1H), 3.93-3.79 (m, 2H), 2.82-2.77 (t, J=7.42 & 7.69 Hz, 2H), 2.43-2.34 (m, 2H), 1.87-1.80 (m, 2H), 1.13-1.09 (t, J=7.42 Hz, 3H). HPLC: Rt=6.09 min following Method R. ES–MS: calcd. for $C_{21}H_{23}FN_2O_3$ (370.42). Found 371 [M+H].

Example 7

Step 1: (2S,3S)-1-(tert-Butoxycarbonyl)-3-hydroxypyrrolidine-2-carboxylic acid was prepared from (2S,3S)-3-Hydroxypyrrolidine-2-carboxylic acid following Method A (yield=91%). The resulting product was used without purification. 1H NMR (DMSO-d6): 5.64-5.63 (d, 1H), 4.42 (bs, 1H), 4.13-4.1 (d, 1H), 3.64-3.48 (m, 2H), 2.11-1.99 (m, 2H), 1.58-1.52 (d, 9H). HPLC: Rt=3.87 min following Method R. ES–MS: calcd. for $C_{10}H_{17}NO_5$ (231.25). Found: 230.2 [M–H].

Step 2: (2S,3S)-1-tert-Butyl 2-methyl 3-hydroxypyrrolidine-1,2-dicarboxylate was prepared from (2S,3S)-1-(tert-butoxycarbonyl)-3-hydroxypyrrolidine-2-carboxylic acid following Method B (quantitative yield). 1H NMR (DMSO-d6): 4.44-4.42 (m, 2H), 4.3-4.2 (d, 1H), 3.75 (s, 3H), 3.68-3.56 (m, 2H), 2.18-2.08 (m, 1H), 1.94-1.75 (m, 1H), 1.47-1.41 (d, 9H). HPLC: Rt=4.45 min following Method R. ES–MS: calcd. for $C_{11}H_{19}N_2O_5$ (245.13). Found: 268.3 [M+Na].

Step 3: (2S,3S)-1-tert-Butyl 2-methyl 3-methoxypyrrolidine-1,2-dicarboxylate was prepared from (2S,3S)-1-tert-butyl 2-methyl 3-hydroxypyrrolidine-1,2-dicarboxylate following Method Q (yield=90%). 1H NMR (DMSO-d6): 4.17-4.1 (d, J=2.2 Hz, 1H), 3.94-3.91 (d, J=10.16 Hz, 1H), 3.67-3.65 (dd, J=1.65 Hz, 3H), 3.47-3.41 (m, 1H), 3.7-3.26 (d, J=1.65 Hz, 3H), 1.93-1.90 (dd, J=4.67 & 3.57 Hz, 2H), 1.38-1.31 (dd, J=1.37 Hz, 9H). HPLC: Rt=4.93 min following Method R. ES–MS: calcd. for $C_{12}H_{21}NO_5$ (259.3). Found: 282.1 [M+Na].

Step 4: (2S,3S)-Methyl 3-methoxypyrrolidine-2-carboxylate hydrochloride salt was prepared from (2S,3S)-1-tert-butyl 2-methyl 3-methoxypyrrolidine-1,2-dicarboxylate following Method F (quantitative yield). 1H NMR (DMSO-d6):

4.4-4.38 (d, J=2.2 Hz, 1H), 4.24-4.2 (dd, J=4.94 & 3.57 Hz, 1H), 3.77 (s, 3H), 3.38-3.3 (m, 1H), 3.3 (s, 3H), 3.3-3.16 (m, 2H), 2.03-1.97 (dd, J=4.67 & 3.57 Hz, 2H). ES–MS: calcd. for $C_7H_{13}NO_3$ (159.18). Found: 160.4 [M+H].

Step 5: (2S,3S)-Methyl 3-methoxy-1-(4'-propylbiphenyl-carbonyl)pyrrolidine-2-carboxylate was prepared from (2S,3S)-methyl 3-methoxypyrrolidine-2-carboxylate hydrochloride salt and 4-(p-n-propylphenyl)-benzoic acid following Method G (quantitative yield). 1H NMR (DMSO-d6): 7.73-7.71 (d, J=8.24 Hz, 2H), 7.63-7.6 (dd, J=3.85 & 4.12 Hz, 4H), 7.31-7.28 (d, J=7.97 Hz, 2H), 4.5 (s, 1H), 4.02-4.0 (d, J=4.4 Hz, 1H), 3.68-3.62 (m, 2H), 3.33-3.32 (d, J=2.2 Hz, 3H), 2.61-2.56 (t, J=7.42 & 7.69 Hz, 2H), 2.06-1.98 (m, 2H), 1.65-1.57 (m, 2H), 0.93-0.88 (t, J=7.14 &7.42 Hz, 3H). HPLC: Rt=6.94 min following Method R. ES–MS: calcd. for $C_{23}H_{27}NO_4$ (381.46). Found: 382.3 [M+H].

Step 6: (2S,3S)—N-Hydroxy-3-methoxy-1-(4'-propylbiphenylcarbonyl)pyrrolidine-2-carboxamide was prepared from (2S,3S)-methyl 3-methoxy-1-(4'-propylbiphenylcarbonyl)pyrrolidine-2-carboxylate following Method H (yield=20%). 1H NMR (DMSO-d6): 11.1 (bs, 1H), 7.92-7.8 (m, 6H), 7.58-7.56 (d, J=7.97 Hz, 4H), 7.51-7.48 (d, J=8.24 Hz, 2H), 4.63 (s, 1H), 4.04 (bs, 1H), 3.86-3.67 (m, 2H), 3.5 (bs, 3H), 2.81-2.76 (t, J=7.42 & 7.97 Hz, 2H), 2.31-2.17 (m, 2H), 1.13-1.08 (t, J=7.14 & 7.42 Hz, 3H). HPLC: Rt=6.05 min following Method R. ES–MS: calcd. for $C_{22}H_{26}N_2O_4$ (382.46). Found: 383.3 [M+H].

Example 8

Step 1: (2S,3S)-1-(tert-Butoxycarbonyl)-3-hydroxypyrrolidine-2-carboxylic acid was prepared from (2S,3S)-3-Hydroxypyrrolidine-2-carboxylic acid following Method A (yield=91%). The resulting product was used without purification. 1H NMR (DMSO-d6): 5.64-5.63 (d, 1H), 4.42 (bs, 1H), 4.13-4.1 (d, 1H), 3.64-3.48 (m, 2H), 2.11-1.99 (m, 2H), 1.58-1.52 (d, 9H). HPLC: Rt=3.868 min following Method R. ES–MS: calcd. for $C_{10}H_{17}NO_5$ (231.25). Found: 230.2 [M–H].

Step 2: (2S,3S)-1-tert-Butyl 2-methyl 3-hydroxypyrrolidine-1,2-dicarboxylate was prepared from (2S,3S)-1-(tert-butoxycarbonyl)-3-hydroxypyrrolidine-2-carboxylic acid following Method B (quantitative yield). 1H NMR (DMSO-d6): 4.44-4.42 (m, 2H), 4.3-4.2 (d, 1H), 3.75 (s, 3H), 3.68-3.56 (m, 2H), 2.18-2.08 (m, 1H), 1.94-1.75 (m, 1H), 1.47-1.41 (d, 9H). HPLC: Rt=4.45 min following Method R. ES–MS: calcd. for $C_{11}H_{19}N_2O_5$ (245.13). Found: 268.3 [M+Na].

Step 5: (2S,3R)-1-tert-Butyl 2-methyl 3-methoxypyrrolidine-1,2-dicarboxylate was prepared from (2S,3S)-1-tert-butyl 2-methyl 3-hydroxypyrrolidine-1,2-dicarboxylate following Methods C, D and Q (yield=75%). 1H NMR (DMSO-d6): 4.17-4.1 (d, J=2.2 Hz, 1H), 3.94-3.91 (d, J=10.16 Hz, 1H), 3.67-3.65 (dd, J=1.65 Hz, 3H), 3.47-3.41 (m, 1H), 3.7-3.26 (d, J=1.65 Hz, 3H), 1.93-1.90 (dd, J=4.67 & 3.57 Hz, 2H), 1.38-1.31 (dd, J=1.37 Hz, 9H). HPLC: Rt=4.93 min following Method R. ES–MS: calcd. for $C_{12}H_{21}NO_5$ (259.3). Found: 282.1 [M+Na].

Step 6: (2S,3R)-Methyl 3-methoxypyrrolidine-2-carboxylate hydrochloride salt was prepared from (2S,3R)-1-tert-butyl 2-methyl 3-methoxypyrrolidine-1,2-dicarboxylate following Method F (quantitative yield). 1H NMR (DMSO-d6): 4.51-4.5 (d, J=3.85 Hz, 1H), 4.28-4.26 (dd, J=4.12 & 1/65 Hz, 1H), 3.77-3.76 (d, J=1.37 Hz, 3H), 3.27-3.24 (m, 2H), 3.23-3.22 (d, J=1.65 Hz, 1H), 2.23-2.15 (m, 1H), 2.04-1.92 (m, 2H). ES–MS: calcd. for $C_7H_{13}NO_3$ (159.18). Found: 160.4 [M+H].

Step 7: (2S,3R)-Methyl 3-methoxy-1-(4'-propylbiphenyl-carbonyl)pyrrolidine-2-carboxylate was prepared from (2S,3R)-methyl 3-methoxypyrrolidine-2-carboxylate hydrochloride salt and 4-(p-n-propylphenyl)-benzoic acid following Method G (yield=92%). 1H NMR (DMSO-d6): 7.74-7.72 (d, J=7.97 Hz, 2H), 7.63-7.6 (dd, J=1.92 & 2.47 Hz, 4H), 7.31-7.28 (d, J=8.24 Hz, 2H), 4.75-4.73 (d, J=6.32 Hz, 1H), 4.25-4.22 (t, J=5.77 & 5.22 Hz, 1H), 3.65 (m, 3H), 3.61-3.51 (m, 2H), 3.32-3.3 (d, J=9.34 Hz, 3H), 2.62-2.56 (t, J=7.42 & 7.69 Hz, 2H), 2.06-1.94 (m, 2H), 1.65-1.57 (m, 2H), 0.93-0.88 (t, J=7.42 & 7.14 Hz, 3H). HPLC: Rt=6.91 min following Method R. ES–MS: calcd. for $C_{23}H_{27}NO_4$ (381.46). Found: 382.3 [M+H].

Step 8: (2S,3R)—N-Hydroxy-3-methoxy-1-(4'-propylbiphenylcarbonyl)pyrrolidine-2-carboxamide was prepared from (2S,3R)-methyl 3-methoxy-1-(4'-propylbiphenylcarbonyl)pyrrolidine-2-carboxylate following Method H (yield=15%). 1H NMR (DMSO-d6): 10.89 (bs, 1H), 7.72-7.6 (m, 6H), 7.38-7.36 (d, J=7.97 Hz, 1H), 7.31-7.28 (d, J=8.24 Hz, 2H), 4.43 (s, 1H), 4.09-3.83 (m, 1H), 3.63-3.43 (m, 2H), 3.33-3.2 (m, 3H), 2.61-2.5 (m, 2H), 2.11-1.95 (m, 2H), 1.67-1.55 (m, 2H), 0.93-0.88 (t, J=7.14 & 7.42 Hz, 3H). HPLC: Rt=6.01 min following Method R. ES–MS: calcd. for $C_{22}H_{26}N_2O_4$ (382.46). Found: 383.3 [M+H].

Example 9

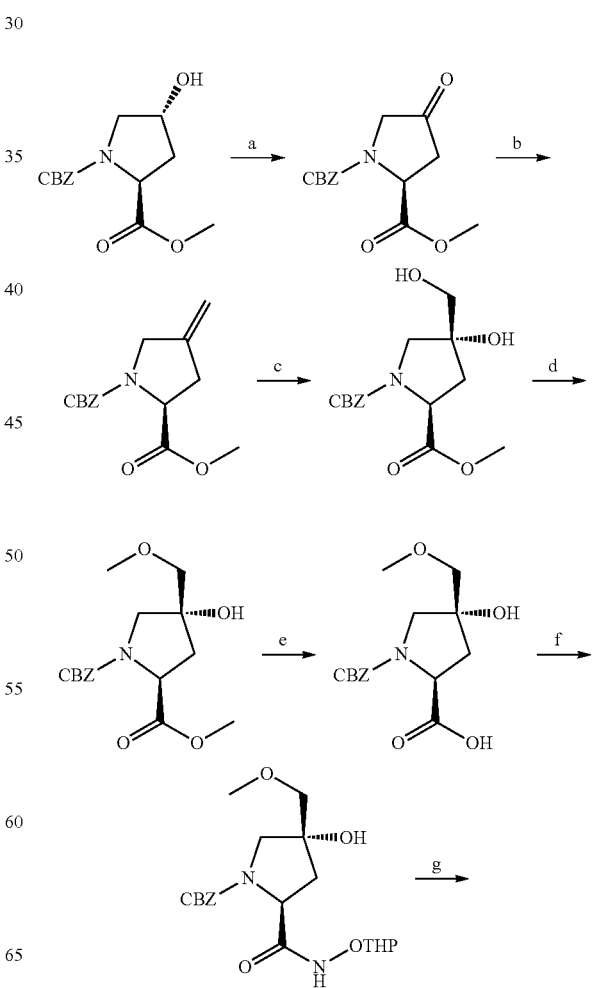

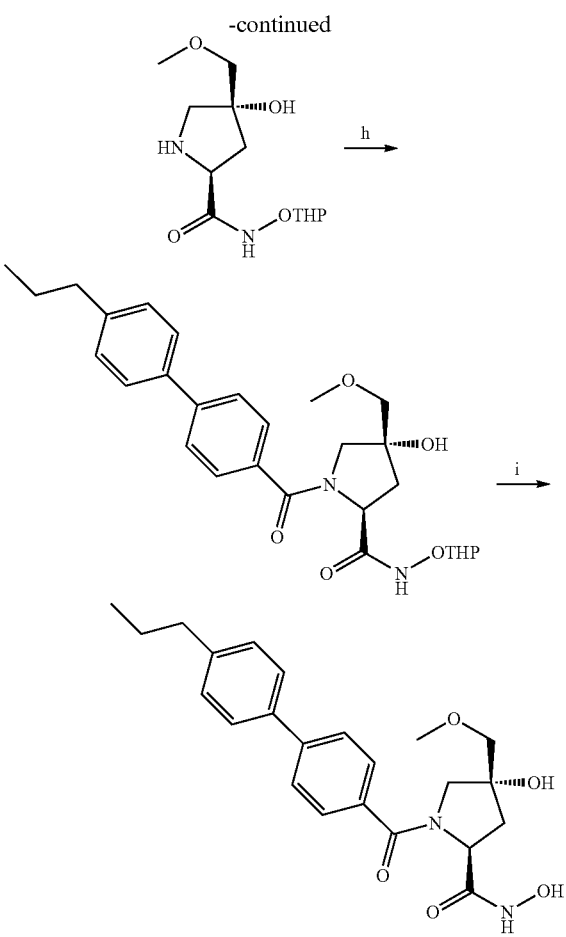

Reagents and conditions. Step 1: DMSO, oxalyl chloride, Et₃N, DCM, −78° C. to rt, 125 min; Step 2: Cp₂ZrCl₂, CH₂Br₂, Zn, THF, rt to 30° C., 3 h; Step 3: OsO₄, 4-methylmorpholin N-oxide (NMO), t-BuOH, acetone, water, rt, 18 h; Step 4: (CH₃)₃OBF₄, 2,6-di-tert-butyl-4-methylpyridine, DCM, 4° C. to rt, 5 h; Step 5: LiOH, MeOH, water, reflux, 1 h; Step 6: HATU, DIEA, DMF, O-(tetrahydro-2H-pyran-2-yl)hydroxylamine, rt, 18 h; Step 7: 10% Pd/C, EtOH, H₂, rt, 8 h; Step 8: 4-(4-n-propylphenyl)benzoic acid, oxalyl chloride, DMF, DCM, rt, 1 h; then DCM, pyridine, rt, 18 h; Step 9: TFA, DCM, rt, 2 h.

Step 1: (S)-1-Benzyl 2-methyl 4-oxopyrrolidine-1,2-dicarboxylate is prepared from (2S,4R)-1-benzyl 2-methyl 4-hydroxypyrrolidine-1,2-dicarboxylate (benzyloxycarbonyl (CBZ)-hydroxyproline methyl ester) following Method U (yield=73%). 1H NMR (300 MHz, CDCl₃) δ 7.42-7.29 (m, 5H), 5.20-5.09 (m, 2H), 4.94-4.81 (m, 1H), 4.07-3.59 (m, 5H), 3.04-2.87 (m, 1H), 2.67-2.56 (m, 1H).

Step 2: (S)-1-Benzyl 2-methyl 4-methylenepyrrolidine-1,2-dicarboxylate is prepared from (S)-1-benzyl 2-methyl 4-oxopyrrolidine-1,2-dicarboxylate following Method V (yield=81%). 1H NMR (300 MHz, CDCl₃) δ 7.42-7.23 (m, 5H), 5.24-4.97 (m, 4H), 4.63-4.48 (m, 1H), 4.22-4.10 (m, 2H), 3.78-3.56 (m, 3H), 3.07-2.88 (m, 1H), 2.72-2.58 (m, 1H).

Step 3: (2S,4R)-1-Benzyl 2-methyl 4-hydroxy-4-(hydroxymethyl)pyrrolidine-1,2-dicarboxylate is prepared from (S)-1-benzyl 2-methyl 4-methylenepyrrolidine-1,2-dicarboxylate following Method W (yield=98%). 1H NMR (300 MHz, CDCl₃) δ 7.40-7.24 (m, 5H), 5.22-4.96 (m, 2H), 4.61-4.42 (m, 1H), 3.82-3.44 (m, 7H), 2.37-1.86 (m, 2H); ESI(+) calcd. for $C_{15}H_{19}NNaO_6$ (332.11). Found 332.5.

Step 4: (2S,4R)-1-Benzyl 2-methyl 4-hydroxy-4-(methoxymethyl)pyrrolidine-1,2-dicarboxylate is prepared from (2S,4R)-1-benzyl 2-methyl 4-hydroxy-4-(hydroxymethyl)pyrrolidine-1,2-dicarboxylate following Method X (yield=60%). 1H NMR (300 MHz, CDCl₃) δ 7.40-7.21 (m, 5H), 5.32-4.97 (m, 2H), 4.61-4.42 (m, 1H), 3.80-3.28 (m, 10H), 2.69-1.87 (m, 2H).

Step 5: (2S,4R)-1-(Benzyloxycarbonyl)-4-hydroxy-4-(methoxymethyl)pyrrolidine-2-carboxylic acid is prepared from (2S,4R)-1-benzyl 2-methyl 4-hydroxy-4-(methoxymethyl)pyrrolidine-1,2-dicarboxylate following Method Y (yield=99%). 1H NMR (300 MHz, CDCl₃) δ 7.40-7.18 (m, 5H), 5.23-5.05 (m, 2H), 4.65-4.47 (m, 1H), 3.78-3.28 (m, 7H), 2.46-1.97 (m, 3H).

Step 6: (2S,4R)-Benzyl 4-hydroxy-4-(methoxymethyl)-2-(tetrahydro-2H-pyran-2-yloxycarbamoyl)pyrrolidine-1-carboxylate is prepared from (2S,4R)-1-(benzyloxycarbonyl)-4-hydroxy-4-(methoxymethyl)pyrrolidine-2-carboxylic acid and O-(tetrahydro-2H-pyran-2-yl)hydroxylamine following Method G (yield=59%). 1H NMR (300 MHz, CHCl₃) δ 7.57-7.18 (m, 5H), 5.33-5.07 (m, 2H), 4.64-4.45 (m, 1H), 4.09-3.21 (m, 7H), 2.44-1.98 (m, 3H); ESI(+) calcd. for $C_{15}H_{18}NO_6$ (308.11). Found 308.0

Step 7: (2S,4R)-4-Hydroxy-4-(methoxymethyl)-N-(tetrahydro-2H-pyran-2-yloxy) pyrrolidine-2-carboxamide is prepared from (2S,4R)-benzyl 4-hydroxy-4-(methoxymethyl)-2-(tetrahydro-2H-pyran-2-yloxycarbamoyl)pyrrolidine-1-carboxylate following Method Z (yield=99%). ESI(+) calcd. for $C_{12}H_{23}N_2O_5$ (275.16). Found 275.2.

Step 8: (2S,4R)-4-Hydroxy-4-(methoxymethyl)-1-(4'-propylbiphenylcarbonyl)-N-(tetrahydro-2H-pyran-2-yloxy)pyrrolidine-2-carboxamide from 4-(4-propylphenyl) benzoic acid is prepared from (2S,4R)-4-hydroxy-4-(methoxymethyl)-N-(tetrahydro-2H-pyran-2-yloxy)pyrrolidine-2-carboxamide and 4-(4-propylphenyl)benzoic acid following Method EE (yield=85%). ESI(−) calcd. for $C_{28}H_{35}N_2O_6$ (495.25). Found 495.2.

Step 9: (2S,4R)—N,4-Dihydroxy-4-(methoxymethyl)-1-(4'-propylbiphenylcarbonyl)pyrrolidine-2-carboxamide is prepared from (2S,4R)-4-hydroxy-4-(methoxymethyl)-1-(4'-propylbiphenylcarbonyl)-N-(tetrahydro-2H-pyran-2-yloxy) pyrrolidine-2-carboxamide following method AA, and purified by preparative-HPLC (yield=30%). 1H NMR (300 MHz, DMSO-d6) δ 10.72 (s, 1H), 8.86 (s, 1H), 7.80-7.48 (m, 6H), 7.26-7.38 (m, 2H), 5.01 (s, 1H), 4.49 (t, J=9.6 Hz, 1H), 3.78 (d, J=10.5 Hz, 1H), 3.27-2.42 (m, 7H), 2.07-1.91 (m, 2H), 1.73-1.55 (m, 2H), 1.33-1.20 (m, 1H), 0.91 (m, 3H); ESI(+) calcd. for $C_{23}H_{28}N_2NaO_5$ (435.19). Found 435.1.

Example 10

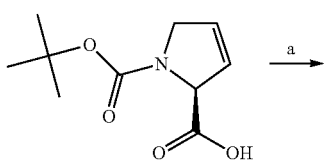

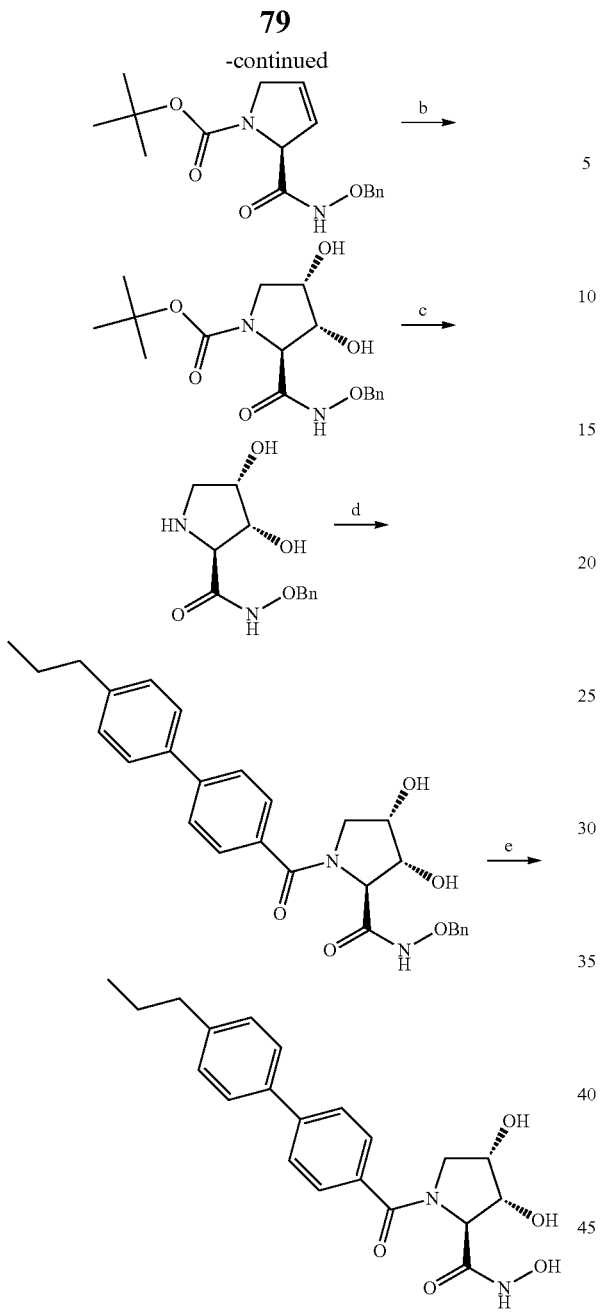

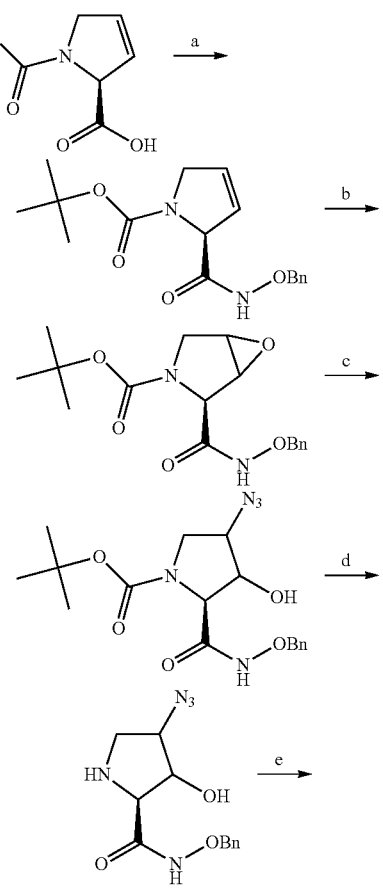

(yield=69%). 1H NMR (300 MHz, CHCl₃) δ 9.79 (s, 1H), 7.48-7.28 (m, 5H), 5.01-4.83 (m, 2H), 4.47-3.41 (m, 5H), 1.83-1.28 (m, 11H).

Step 3: (2S,3R,4S)—N-(benzyloxy)-3,4-dihydroxypyrrolidine-2-carboxamide is prepared from (2S,3R,4S)-tert-butyl 3,4-dihydroxy-2-(benzyloxycarbamoyl)pyrrolidine-1-carboxylate following Method AA (yield=100%). ESI(+) calcd. for $C_{12}H_{17}N_2O_4$ (253.12). Found 253.2.

Step 4: (2S,3R,4S)—N-(benzyloxy)-3,4-dihydroxy-1-(4'-propylbiphenylcarbonyl)pyrrolidine-2-carboxamide is prepared from (2S,3R,4S)—N-(benzyloxy)-3,4-dihydroxypyrrolidine-2-carboxamide and 4-(4-propylphenyl)benzoic acid following Method G (yield=93%). 1H NMR (300 MHz, CHCl₃) δ 7.70-6.90 (m, 13H), 4.97-4.78 (m, 2H), 4.66-4.37 (m, 2H), 4.30-4.07 (m, 2H), 3.83-3.45 (m, 2H), 2.96-2.78 (m, 2H), 2.74-2.48 (m, 2H), 1.90-1.53 (m, 2H), 1.13-0.85 (m, 3H).

Step 5: (2S,3R,4S)—N,3,4-Trihydroxy-1-(4'-propylbiphenylcarbonyl)pyrrolidine-2-carboxamide is prepared from (2S,3R,4S)—N-(benzyloxy)-3,4-dihydroxy-1-(4'-propylbiphenylcarbonyl)pyrrolidine-2-carboxamide following Method Z. The compound was purified by preparative-HPLC (yield=32%). 1H NMR (300 MHz, DMSO-d6) δ 10.78 (s, 1H), 7.87-7.46 (m, 6H), 7.40-7.19 (m, 2H), 4.26-3.22 (m, 7H), 2.70-2.37 (m, 2H), 1.74-1.46 (m, 2H), 1.03-0.76 (m, 3H); ESI(−) calcd. for $C_{21}H_{23}N_2O_5$ (383.16). Found 383.2.

Example 11

Reagents and conditions. Step 1: O-benylhydroxylamine, HATU, DIEA, DMF, rt, 18 h; Step 2: OsO₄, NMO, t-BuOH, acetone, water, rt, 18 h; Step 3: TFA, DCM, rt, 2 h; Step 4: 4-(4-n-propylphenyl)benzoic acid, HATU, DIEA, DMF, rt, 18 h; Step 5: 10% Pd/C, EtOH, H₂, rt, 8 h.

Step 1: (S)-tert-Butyl 2-(benzyloxycarbamoyl)-2,5-dihydro-1H-pyrrole-1-carboxylate is prepared from (S)-1-(tert-butoxycarbonyl)-2,5-dihydro-1H-pyrrole-2-carboxylic acid (Boc-3,4-dehydro-proline) and O-benzylhydroxylamine following Method G. 1H NMR (300 MHz, CHCl₃) δ 9.38 (s, 0.5H), 8.46 (s, 0.5H), 7.52-7.22 (m, 5H), 6.01-5.77 (m, 2H), 5.04-4.79 (m, 3H), 4.38-3.99 (m, 2H), 1.43 (s, 9).

Step 2: (2S,3R,4S)-tert-Butyl 3,4-dihydroxy-2-(benzyloxycarbamoyl)pyrrolidine-1-carboxylate is prepared from (S)-tert-butyl 2-(tetrahydro-2H-pyran-2-yloxycarbamoyl)-2,5-dihydro-1H-pyrrole-1-carboxylate following Method W -continued

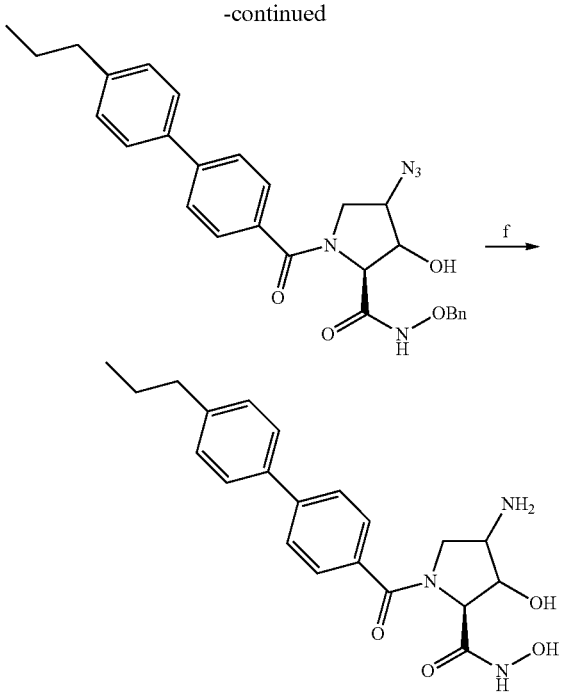

Reagents and conditions. Step 1: O-benylhydroxylamine, HATU, DIEA, DMF, rt, 18 h; Step 2: MCPBA, DCM, 0° C. to rt, 18 h; Step 3: sodium azide, DMF, water, 80° C., 18 h; Step 4: TFA, DCM, rt, 2 h; Step 5: 4-(4-n-propylphenyl)benzoic acid, HATU, DIEA, DMF, rt, 18 h; Step 6: 10% Pd/C, EtOH, H$_2$, rt, 8 h.

Step 1: (S)-tert-Butyl 2-(benzyloxycarbamoyl)-2,5-dihydro-1H-pyrrole-1-carboxylate is prepared from (S)-1-(tert-butoxycarbonyl)-2,5-dihydro-1H-pyrrole-2-carboxylic acid (Boc-3,4-dehydro-proline) and O-benzylhydroxylamine following Method G (yield=86%). 1H NMR (300 MHz, CHCl$_3$) δ 9.38 (s, 0.5H), 8.46 (s, 0.5H), 7.52-7.22 (m, 5H), 6.01-5.77 (m, 2H), 5.04-4.79 (m, 3H), 4.38-3.99 (m, 2H), 1.43 (s, 9H).

Step 2: (1R,2S,5S)-tert-Butyl 2-(benzyloxycarbamoyl)-6-oxa-3-azabicyclo[3.1.0]hexane-3-carboxylate is prepared from (S)-tert-butyl 2-benzyloxycarbamoyl-2,5-dihydro-1H-pyrrole-1-carboxylate following Method CC. (yield=31%). 1H NMR (300 MHz, CHCl$_3$) δ 9.83-9.00 (m, 1H), 8.14-7.26 (m, 5H), 5.22-4.79 (m, 2H); 4.54-3.24 (m, 5H), 1.38 (s, 9H); ESI(−) calcd. for C$_{17}$H$_{21}$N$_2$O$_5$ (333.15). Found 333.2

Step 3: (2S,3R,4R)-tert-Butyl 4-azido-2-(benzyloxycarbamoyl)-3-hydroxypyrrolidine-1-carboxylate is prepared from (1R,2S,5S)-tert-butyl 2-(benzyloxycarbamoyl)-6-oxa-3-azabicyclo[3.1.0]hexane-3-carboxylate following Method DD (yield=79%). 1H NMR (300 MHz, CHCl$_3$) δ 9.78-8.88 (m, 1H), 7.78-7.22 (m, 5H), 5.06-3.64 (m, 7H), 3.48-3.18 (m, 1H), 1.37 (m, 9H); ESI(−) calcd. for C$_{17}$H$_{22}$N$_5$O$_5$ (376.16). Found 376.2.

Step 4: (2S,3R,4R)-4-Azido-N-(benzyloxy)-3-hydroxypyrrolidine-2-carboxamide is prepared from (2S,3R,4R)-tert-butyl 4-azido-2-(benzyloxycarbamoyl)-3-hydroxypyrrolidine-1-carboxylate following Method AA (yield=100%). ESI(+) calcd. for C$_{12}$H$_{16}$N$_5$O$_3$ (287.13). Found 287.2.

Step 5: (2S,3R,4R)-4-Azido-N-(benzyloxy)-3-hydroxy-1-(4'-propylbiphenylcarbonyl)pyrrolidine-2-carboxamide is prepared from (2S,3R,4R)-4-azido-N-(benzyloxy)-3-hydroxypyrrolidine-2-carboxamide and 4-(4-propylphenyl) benzoic acid following Method G (yield=84%). ESI(−) calcd. for C$_{28}$H$_{28}$N$_5$O$_4$ (498.21). Found 498.2.

Step 6: (2S,3S,4R)-4-Amino-N,3-dihydroxy-1-(4'-propylbiphenylcarbonyl)pyrrolidine-2-carboxamide is prepared from (2S,3R,4R)-4-azido-N-(benzyloxy)-3-hydroxy-1-(4'-propylbiphenylcarbonyl)pyrrolidine-2-carboxamide following Method Z. The compound was purified by preparative-HPLC (yield=8%). 1H NMR (300 MHz, DMSO-d6) δ 9.23-9.10 (m, 1H), 7.74-7.38 (m, 8H), 7.34-7.16 (m, 2H), 6.48-6.16 (m, 1H), 4.20-3.38 (m, 6H), 2.64-2.40 (m, 2H), 0.94-0.69 (m, 3H); ESI(+) calcd. for C$_{21}$H$_{26}$N$_3$O$_4$ (384.19). Found 384.2.

Example 12

Step 1: (S)-tert-Butyl 2-(benzylocarbamoyl)-2,5-dihydro-1H-pyrrole-1-carboxylate is prepared from (S)-1-(tert-butoxycarbonyl)-2,5-dihydro-1H-pyrrole-2-carboxylic acid (Boc-3,4-dehydro-proline) and O-benzylhydroxylamine following Method G (yield=86%). 1H NMR (300 MHz, CHCl$_3$) δ 9.38 (s, 0.5H), 8.46 (s, 0.5H), 7.52-7.22 (m, 5H), 6.01-5.77 (m, 2H), 5.04-4.79 (m, 3H), 4.38-3.99 (m, 2H), 1.43 (s, 9H).

Step 2: (1S,2S,5R)-tert-Butyl 2-(benzyloxycarbamoyl)-6-oxa-3-azabicyclo[3.1.0]hexane-3-carboxylate is prepared from (S)-tert-butyl 2-(benzyloxycarbamoyl)-2,5-dihydro-1H-pyrrole-1-carboxylate following Method CC (yield=12%). 1H NMR (300 MHz, CHCl$_3$) δ 8.80-8.41 (m, 1H), 8.13-7.26 (m, 5H), 5.16-4.78 (m, 2H), 4.44-3.37 (m, 5H), 1.38 (s, 9H); ESI(−) calcd. for C$_{17}$H$_{21}$N$_2$O$_5$ (333.15). Found 333.2

Step 3: (2S,3S,4S)-tert-Butyl 4-azido-2-(benzyloxycarbamoyl)-3-hydroxypyrrolidine-1-carboxylate is prepared from (1S,2S,5R)-tert-butyl 2-(benzyloxycarbamoyl)-6-oxa-3-azabicyclo[3.1.0]hexane-3-carboxylate following Method DD (yield=66%). 1H NMR (300 MHz, CHCl$_3$) δ 9.80-8.86 (m, 1H), 7.81-7.21 (m, 5H), 5.05-3.65 (m, 7H), 3.48-3.17 (m, 1H), 1.37 (m, 9H); ESI(−) calcd. for C$_{17}$H$_{22}$N$_5$O$_5$ (376.16). Found 376.2.

Step 4: (2S,3S,4S)-4-Azido-N-(benzyloxy)-3-hydroxypyrrolidine-2-carboxamide is prepared from (2S,3S,4S)-tert-butyl 4-azido-2-(benzyloxycarbamoyl)-3-hydroxypyrrolidine-1-carboxylate following Method AA (yield=100%). ESI(+) calcd. for C$_{12}$H$_{16}$N$_5$O$_3$ (287.13). Found 287.2.

Step 5: (2S,3S,4S)-4-Azido-N-(benzyloxy)-3-hydroxy-1-(4'-propylbiphenylcarbonyl)pyrrolidine-2-carboxamide is prepared from (2S,3S,4S)-4-azido-N-(benzyloxy)-3-hydroxypyrrolidine-2-carboxamide and 4-(4-propylphenyl) benzoic acid following Method G (yield=105%). ESI(−) calcd. for C$_{28}$H$_{28}$N$_5$O$_4$ (498.21). Found 498.2.

Step 6: (2S,3R,4S)-4-Amino-N,3-dihydroxy-1-(4'-propylbiphenylcarbonyl)pyrrolidine-2-carboxamide is prepared from (2S,3S,4S)-4-azido-N-(benzyloxy)-3-hydroxy-1-(4'-propylbiphenylcarbonyl)pyrrolidine-2-carboxamide following Method Z (yield=10%). The compound was purified by preparative-HPLC. 1H NMR (300 MHz, DMSO-d6) δ 10.66 (s, 0.5H), 8.97 (s, 0.5H), 8.40-7.98 (m, 2H), 7.81-7.42 (m, 6H), 7.38-7.16 (m, 2H), 6.62-6.17 (m, 1H), 4.60-3.38 (m, 6H), 2.66-2.40 (m, 2H), 1.65-1.48 (m, 2H), 1.02-0.77 (m, 3H); ESI(+) calcd. for C$_{21}$H$_{26}$N$_3$O$_4$ (384.19). Found 384.4

Example 13

Step 1: (S)-3-tert-Butyl 2-methyl thiazolidine-2,3-dicarboxylate was prepared from (S)-3-(tert-butoxycarbonyl)thiazolidine-2-carboxylic acid following Method B using the commercially available Boc-protected carboxylic acid (yield=81%). ES–MS: calcd. for C$_{10}$H$_{17}$NO$_4$S (247.31).

Step 2: (S)-Methyl thiazolidine-2-carboxylate hydrochloride salt was prepared from (S)-3-tert-butyl 2-methyl thiazolidine-2,3-dicarboxylate following Method F (quantitative yield). 1H NMR (DMSO-d6): 5.67 (d, J=1.65 Hz, 1H), 3.96-3.95 (d, J=1.65 Hz, 1H), 3.75-3.70 (m, 2H), 3.4-3.35 (m, 2H). ES–MS: calcd. for $C_5H_9NO_2S$ (147.2). Found: 148.1[M+H].

Step 3: (S)-Methyl 3-(4'-propylbiphenylcarbonyl)thiazolidine-2-carboxylate was prepared from (S)-methyl thiazolidine-2-carboxylate hydrochloride salt and 4-(p-n-propylphenyl)-benzoic acid following Method G (yield=42%). 1H NMR (DMSO-d6): 7.76-7.73 (d, J=8.24 Hz, 2H), 7.64-7.61 (d, J=8.24 Hz, 4H), 7.32-7.29 (d, J=8.24 Hz, 2H), 5.575 (bs, 1H), 4.0 (bs, 1H), 3.89-3.82 (m, 1H), 3.7 (s, 3H), 3.18-3.14 (t, J=6.32 & 6.04 Hz, 2H), 2.62-2.56 (t, J=7.14 & 7.97 Hz, 2H), 1.67-1.55 (m, 2H), 0.93-0.88 (t, J=7.14 & 7.42 Hz, 3H). HPLC: Rt=7.27 min following Method R. ES–MS: calcd. for $C_{21}H_{23}NO_3S$ (369.48). Found: 392.2 [M+Na].

Step 4: (S)—N-Hydroxy-3-(4'-propylbiphenylcarbonyl) thiazolidine-2-carboxamide was prepared (S)-methyl 3-(4'-propylbiphenylcarbonyl)thiazolidine-2-carboxylate from following Method H (yield=15%). 1H NMR (DMSO-d6): 10.76 (bs, 1H), 9.05 (bs, 1H), 7.74-7.72 (d, J=8.24 Hz, 2H), 7.63-7.61 (d, J=8.24 Hz, 4H), 7.31-7.29 (d, J=7.97 Hz, 2H), 5.525 (bs, 1H), 3.89 (bs, 1H), 3.43 (bs, 1H), 3.17-3.06 (m, 1H), 2.62-2.57 (t, J=7.14 & 7.97 Hz, 2H), 1.68-1.55 (m, 2H), 0.93-0.88 (t, J=7.42 Hz, 3H). HPLC: Rt=6.09 min following Method R. ES–MS: calcd. for $C_{20}H_{22}N_2O_3S$ (370.47). Found: 371 [M+H].

Example 14

Step 1: (S)-3-tert-Butyl 2-methyl thiazolidine-2,3-dicarboxylate was prepared from (S)-3-(tert-butoxycarbonyl)thiazolidine-2-carboxylic acid following Method B using the commercially available Boc-protected carboxylic acid (yield=81%). ES–MS: calcd. for $C_{10}H_{17}NO_4S$ (247.31).

Step 2: (S)-Methyl thiazolidine-2-carboxylate hydrochloride salt was prepared from (S)-3-tert-butyl 2-methyl thiazolidine-2,3-dicarboxylate following Method F (quantitative yield) 1H NMR (DMSO-d6): 5.67 (d, J=1.65 Hz, 1H), 3.96-3.95 (d, J=1.65 Hz, 1H), 3.75-3.70 (m, 2H), 3.4-3.35 (m, 2H). ES–MS: calcd. for $C_5H_9NO_2S$ (147.2). Found: 148.1[M+H].

Step 3: (S)-Methyl 3-(4'-propylbiphenylcarbonyl)thiazolidine-2-carboxylate was prepared from (S)-methyl thiazolidine-2-carboxylate hydrochloride salt and 4-(p-n-propylphenyl)-benzoic acid following Method G (yield=42%). 1H NMR (DMSO-d6): 7.76-7.73 (d, J=8.24 Hz, 2H), 7.64-7.61 (d, J=8.24 Hz, 4H), 7.32-7.29 (d, J=8.24 Hz, 2H), 5.575 (bs, 1H), 4.0 (bs, 1H), 3.89-3.82 (m, 1H), 3.7 (s, 3H), 3.18-3.14 (t, J=6.32 & 6.04 Hz, 2H), 2.62-2.56 (t, J=7.14 & 7.97 Hz, 2H), 1.67-1.55 (m, 2H), 0.93-0.88 (t, J=7.14 & 7.42 Hz, 3H). HPLC: Rt=7.27 min following Method R. ES–MS: calcd. for $C_{21}H_{23}NO_3S$ (369.48). Found: 392.2 [M+Na].

Step 4: (S)-Methyl 3-(4'-propylbiphenylcarbonyl)thiazolidinesulfoxide-2-carboxylate was prepared from (S)-methyl 3-(4'-propylbiphenylcarbonyl)thiazolidine-2-carboxylate following Method S (yield=20%-30%). The two isomers were isolated as a mixture in the ratio of 2:1 by NMR. 1H NMR (DMSO-d6): 8.09-8.07 (m, 2H), 7.97-7.7 (m, 4H), 7.52-7.49 (d, J=7.97 Hz, 2H), 5.96 (bs, 0.33H), 5.94 (bs, 0.66H), 4.46 (bs, 1H), 3.95 (bs, 3H), 3.41-3.21 (m, 2H), 2.82-2.77 (t, J=7.42 & 7.69 Hz, 2H), 1.87-1.75 (m, 2H), 1.13-1.08 (t, J=7.42 Hz, 3H). HPLC: Rt=6.37 & 6.39 min following Method R. ES–MS: calcd. for $C_{21}H_{23}NO_4S$ (385.48). Found: 408.1 [M+Na].

Step 5: (S)—N-Hydroxy-3-(4'-propylbiphenylcarbonyl) thiazolidinesulfoxide-2-carboxamide was prepared from (S)-methyl 3-(4'-propylbiphenylcarbonyl)-2-thiazolidinesulfoxide-2-carboxylate following Method T (yield=40%). This was a diastereomeric mixture in the ratio of 2:1. 1H NMR (DMSO-d6): 11.52-11.28 (d, 1H), 9.55 (bs, 1H), 7.97-7.94 (d, J=7.97 Hz, 2H), 7.84-7.82 (d, J=8.24 Hz, 4H), 7.52-7.49 (d, J=7.97 Hz, 2H), 5.84 (bs, 0.33H), 5.45 (bs, 0.66H), 4.39 (bs, 2H), 3.25 (bs, 2H), 2.82-2.77 (t, J=7.42 & 7.69 Hz, 2H), 1.94-1.42 (m, 2H), 1.13-1.08 (t, J=7.42 min following Method R. ES–MS: calcd. for $C_{20}H_{22}N_2O_4S$ (386.47). Found: 385.2 [M–H].

Example 15

Step 1: (S)-3-tert-Butyl 2-methyl thiazolidine-2,3-dicarboxylate was prepared from (S)-3-(tert-butoxycarbonyl)thiazolidine-2-carboxylic acid following Method B using the commercially available Boc-protected carboxylic acid (yield=81%). ES–MS: calcd. for $C_{10}H_{17}NO_4S$ (247.31).

Step 2: (S)-Methyl thiazolidine-2-carboxylate hydrochloride salt was prepared from (S)-3-tert-butyl 2-methyl thiazolidine-2,3-dicarboxylate following Method F (quantitative yield). 1H NMR (DMSO-d6): 5.67 (d, J=1.65 Hz, 1H), 3.96-3.95 (d, J=1.65 Hz, 1H), 3.75-3.70 (m, 2H), 3.4-3.35 (m, 2). ES–MS: calcd. for $C_5H_9NO_2S$ (147.2). Found: 148.1[M+H].

Step 3: (S)-Methyl 3-(4'-propylbiphenylcarbonyl)thiazolidine-2-carboxylate was prepared from (S)-methyl thiazolidine-2-carboxylate hydrochloride salt and 4-(p-n-propylphenyl)-benzoic acid following Method G (yield=42%). 1H NMR (DMSO-d6): 7.76-7.73 (d, J=8.24 Hz, 2H), 7.64-7.61 (d, J=8.24 Hz, 4H), 7.32-7.29 (d, J=8.24 Hz, 2H), 5.575 (bs, 1H), 4.0 (bs, 1H), 3.89-3.82 (m, 1H), 3.7 (s, 3H), 3.18-3.14 (t, J=6.32 & 6.04 Hz, 2H), 2.62-2.56 (t, J=7.14 & 7.97 Hz, 2H), 1.67-1.55 (m, 2H), 0.93-0.88 (t, J=7.14 & 7.42 Hz, 3H). HPLC: Rt=7.27 min following Method R. ES–MS: calcd. for $C_{21}H_{23}NO_3S$ (369.48). Found: 392.2 [M+Na].

Step 4: (S)—N-(Benzyloxy)-3-(4'-propylbiphenylcarbonyl)thiazolidine-2-carboxamide was prepared from (S)-methyl 3-(4'-propylbiphenylcarbonyl)thiazolidine-2-carboxylate following Method I (yield=80%). 1H NMR (DMSO-d6): 11.38 (bs, 1H), 7.7-7.6 (m, 5H), 7.36-7.3 (m, 8H), 5.75 (bs, 1H), 4.78 (bs, 2H), 3.89 (bs, 1H), 3.3-3.1 (m, 2H), 2.62-2.57 (t, J=7.42 & 7.69 Hz, 2H), 1.67-1.55 (m, 2H), 0.93-0.88 (t, J=7.14 & 7.42 Hz, 3H). HPLC: Rt=7.115 min following Method R. ES–MS: calcd. for $C_{27}H_{28}N_2O_3S$ (460). Found: 461 [M+H].

Step 5: (S)—N-(Benzyloxy)-3-(4'-propylbiphenylcarbonyl)thiazolidinesulfone-2-carboxamide was prepared from (S)—N-(benzyloxy)-3-(4'-propylbiphenylcarbonyl)thiazolidine-2-carboxamide following Method S (yield=60%). 1H NMR (DMSO-d6): 11.96 (bs, 1H), 7.77-7.52 (m, 6H), 7.37-7.3 (m, 7H), 5.27 (bs, 1H), 4.80 (bs, 2H), 4.07-3.96 (m, 2H), 3.79-3.75 (t, J=6.32 Hz, 1H), 3.56-3.338 (m, 1H), 2.63-2.57 (t, J=8.24 & 7.14 Hz, 2H), 1.68-1.56 (m, 2H), 0.93-0.88 (t, J=7.42 & 7.14 Hz, 3H). HPLC: Rt=6.97 min following Method R. ES–MS: calcd. for $C_{27}H_{28}N_2O_5S$ (492.59). Found: 493.2 [M+H].

Step 6: (S)—N-Hydroxy-3-(4'-propylbiphenylcarbonyl) thiazoldinesulfone-2-carboxamide was prepared from (S)—N-(benzyloxy)-3-(4'-propylbiphenylcarbonyl)thiazolidinesulfone-2-carboxamide following Method P (yield=30%). The compound was isolated as containing 15%-20% of the opposite isomer, as analyzed by HPLC and using a chiral column. 1H NMR (DMSO-d6): 11.47 (bs, 1H), 9.68 (bs, 1H), 7.98-7.95 (d, J=8.24 Hz, 2H), 7.85-7.82 (d, J=7.97 Hz, 4H), 7.52-7.49 (d, J=7.97 Hz, 2H), 5.5 (bs, 1H), 4.27 (bs, 1H), 3.92 (bs, 1H), 3.69-3.65 (m, 2H), 2.82-2.77 (t, J=7.42 & 7.69 Hz, 2H), 1.85-1.78 (m, 2H), 1.13-1.08 (t, J=7.14 & 7.42 Hz, 3H).

HPLC: Rt=5.92 min following Method R. ES–MS: calcd. for $C_{20}H_{22}N_2O_5S$ (402.469). Found: 401.2 [M–H].

Example 16

Step 1: (S)-3-tert-butyl 4-methyl thiazolidine-3,4-dicarboxylate was prepared from (S)-3-(tert-butoxycarbonyl)thiazolidine-4-carboxylic acid following Method B using the commercially available Boc-protected carboxylic acid (yield=92%). 1H NMR (DMSO-d6): 4.94-4.81 (d, 1H), 4.74-4.68 (d, J=9.07 Hz, 1H), 4.56-4.54 (d, J=7.97 Hz, 1H), 3.86 (s, 3H), 3.61-3.58 (d, J=7.97 Hz, 1H), 3.34-3.31 (d, J=7.14 Hz, 1H), 1.6-1.54 (d, J=15.9 HZ, 9H). HPLC: Rt=5.125 min following Method R. ES–MS: calcd. for $C_{10}H_{17}NO_4S$ (247.09). Found: 270 [M+Na].

Step 2: (S)-Methyl thiazolidine-4-carboxylate hydrochloride salt was prepared from (S)-3-tert-butyl 4-methyl thiazolidine-3,4-dicarboxylate following Method F (quantitative yield) 1H NMR (DMSO-d6): 4.77-4.72 (t, J=6.87 & 6.59 Hz, 1H), 4.33-4.23 (dd, J=9.6 Hz, 1H), 3.76 (d, 3H), 3.39-3.23 (m, 2H). ES–MS: calcd. for $C_5H_9NO_2S$ (147.2). Found: 148.1 [M+H].

Step 3: (S)-Methyl 3-(4'-propylbiphenylcarbonyl)thiazolidine-4-carboxylate was prepared from (S)-methyl thiazolidine-4-carboxylate hydrochloride salt and 4-(p-n-propylphenyl)-benzoic acid following Method G (yield=75%). 1H NMR (DMSO-d6): 7.95-7.93 (d, J=7.97 Hz, 2H), 7.83-7.80 (d, J=8.24 Hz, 4H), 7.51-7.48 (d, J=7.97 Hz, 2H), 5.25 (bs, 1H), 4.85-4.83 (d, J=7.14 Hz, 2H), 3.88 (m, 3H), 3.76-3.66 (m, 1H), 3.49-3.38 (m, 1H), 2.81-2.76 (t, J=7.42 & 7.69 Hz, 2H), 1.85-1.75 (m, 2H), 1.13-1.08 (t, J=7.14 & 7.42 Hz, 3H). HPLC: Rt=7.19 min following Method R. ES–MS: calcd. for $C_{21}H_{23}NO_3S$ (369.48). Found: 392 [M+Na].

Step 4: (S)—N-Hydroxy-3-(4'-propylbiphenylcarbonyl)thiazolidine-4-carboxamide was prepared from (S)-methyl 3-(4'-propylbiphenylcarbonyl)thiazolidine-4-carboxylate following Method H (yield=40%). 1H NMR (DMSO-d6): 10.84 (bs, 1H), 7.75-7.73 (d, J=7.97 Hz, 2H), 7.64-7.61 (d, J=7.97 Hz, 4H), 7.32-7.29 (d, J=8.24 Hz, 2H), 4.86 (bs, 1H), 4.65 (bs, 2H), 3.35 (bs, 1H), 3.13-3.07 (dd, J=5.49 Hz, 1H), 2.62-2.57 (t, J=7.42 & 7.69 Hz, 2H), 1.68-1.55 (m, 2H), 0.93-0.88 (t, J=7.14 & 7.42 Hz, 3H). HPLC: Rt=6.09 min following Method R. ES–MS: calcd. for $C_{20}H_{22}N_2O_3S$ (370.47). Found: 371.4 [M+H].

Example 17

Step 1: (S)-3-tert-Butyl 4-methyl thiazolidine-3,4-dicarboxylate was prepared from (S)-3-(tert-butoxycarbonyl)thiazolidine-4-carboxylic acid following Method B using the commercially available Boc-protected carboxylic acid (yield 92%). 1H NMR (DMSO-d6): 4.94-4.81 (d, 1H), 4.74-4.68 (d, J=9.07 Hz, 1H), 4.56-4.54 (d, J=7.97 Hz, 1H), 3.86 (s, 3H), 3.61-3.58 (d, J=7.97 Hz, 1 h), 3.34-3.31 (d, J=7.14 Hz, 1H), 1.6-1.54 (d, J=15.9 HZ, 9H). HPLC: Rt=5.125 min following Method R. ES–MS: calcd. for $C_{10}H_{17}NO_4S$ (247.09). Found: 270[M+Na].

Step 2: (S)-Methyl thiazolidine-4-carboxylate hydrochloride salt was prepared from (S)-3-tert-butyl 4-methyl thiazolidine-3,4-dicarboxylate following Method F (quantitative yield). 1H NMR (DMSO-d6): 4.77-4.72 (t, J=6.87 & 6.59 Hz, 1H), 4.33-4.23 (dd, J=9.6 Hz, 1H), 3.76 (d, 3H), 3.39-3.23 (m, 2H), ES–MS: calcd. for $C_5H_9NO_2S$ (147.2). Found: 148.1 [M+H].

Step 3: (S)-Methyl 3-(1-(4'-propylbiphenyl carbonyl)thiazolidine-4-carboxylate was prepared from (S)-methyl thiazolidine-4-carboxylate hydrochloride salt and 4-(p-n-propylphenyl)-benzoic acid following Method G (yield=75%) 1H NMR (DMSO-d6): 7.95-7.93 (d, J=7.97 Hz, 2H), 7.83-7.80 (d, J=8.24 Hz, 4H), 7.51-7.48 (d, J=7.97 Hz, 2H), 5.25 (bs, 1H), 4.85-4.83 (d, J=7.14 Hz, 2H), 3.88 (m, 3H), 3.76-3.66 (m, 1H), 3.49-3.38 (m, 1H), 2.81-2.76 (t, J=7.42 & 7.69 Hz, 2H), 1.85-1.75 (m, 2H), 1.13-1.08 (t, J=7.14 & 7.42 Hz, 3H). HPLC: Rt=7.19 min following Method R. ES–MS: calcd. for $C_{21}H_{23}NO_3S$ (369.48). Found: 392 [M+Na].

Step 4: (S)-Methyl 3-(4'-propylbiphenylcarbonyl)thiazolidinesulfone-4-carboxylate was prepared from (S)-methyl 3-(1-(4'-propylbiphenyl carbonyl)thiazolidine-4-carboxylate following Method S (yield=70%). 1H NMR (DMSO-d6): 7.8-7.77 (d, J=8.24 Hz, 2H), 7.65-7.53 (m, 4H), 7.33-7.31 (d, J=7.69 Hz, 2H), 5.44 (bs, 1H), 4.91-4.8 (d, 2H), 4.0-3.97 (m, 1H), 3.75-3.69 (m, 1H), 3.73 (s, 3H), 2.62-2.57 (t, J=7.42 Hz, 2H), 1.68-1.56 (m, 2H), 0.93-0.88 (m, 3H). HPLC Rt=6.78 min following Method R. ES–MS: calcd. for $C_{21}H_{23}NO_5S$ (401.48). Found: 424 [M+Na].

Step 5: (S)—N-(Benzyloxy)-3-(4'-propylbiphenylcarbonyl)thiazolidinesulfone-4-carboxamide was prepared from (S)-methyl 3-(4'-propylbiphenylcarbonyl)thiazolidinesulfone-4-carboxylate following Method I (yield=60%). 1H NMR (DMSO-d6): 7.79-7.76 (d, J=8.24 Hz, 2H), 7.66-7.63 (d, J=7.97 Hz, 4H), 7.4-7.3 (m, 7H), 5.75 (bs, 1H), 4.81 (bs, 4H), 3.86-3.79 (dd, J=8.79 Hz, 1H), 3.56-3.41 (m, 1H), 2.63-2.58 (t, J=7.42 & 7.69 Hz, 2H), 1.68-1.56 (m, 2H), 0.93-0.89 (t, J=7.14 & 7.42 Hz, 3H). HPLC: Rt=6.97 min following Method R. ES–MS: calcd. for $C_{27}H_{28}N_2O_5S$ (492.59). Found: 515.2 [M+Na].

Step 6: (S)—N-Hydroxy-3-(4'-propylbiphenylcarbonyl)thiazolidinesulfone-4-carboxamide was prepared from (S)—N-(benzyloxy)-3-(4'-propylbiphenylcarbonyl)thiazolidinesulfone-4-carboxamide following Method P (yield=80%). 1H NMR (DMSO-d6): 11.07 (bs, 1H), 9.2 (bs, 1H), 7.8-7.76 (d, J=8.24 Hz, 2H), 7.65-7.63 (d, J=8.24 Hz, 4H), 7.32-7.3 (d, J=7.97 Hz, 2H), 5.2 (bs, 1H), 4.85 (bs, 2H), 3.9-3.83 (m, 1H), 3.47-3.41 (m, 1H), 2.62-2.57 (t, J=7.42 & 7.69 Hz, 2H), 1.68-1.55 (m, 2H), 0.93-0.88 (t, J=7.14 & 7.42 Hz, 3H). HPLC: Rt=5.99 min following Method R. ES–MS: calcd. for $C_{20}H_{22}N_2O_5S$ (402.47). Found: 401.4 [M+H].

Example 18

Step 1: (R)-3-tert-Butyl 2-methyl thiazolidine-2,3-dicarboxylate was prepared from (R)-3-(tert-butoxycarbonyl)thiazolidine-2-carboxylic acid following Method B using the commercially available Boc-protected carboxylic acid following Method F (yield=94%). 1H NMR (DMSO-d6): 5.43-5.37 (d, 1H), 3.96 (bs, 2H), 3.87 (s, 2H), 3.27 (bs, 2H), 1.59-1.53 (d, 9H). HPLC: Rt=5.31 (d, 1H), ES–MS: calcd. for $C_{10}H_{17}NO_4S$ (247.09). Found: 269.9 [M+Na].

Step 2: (R)-Methyl thiazolidine-2-carboxylate hydrochloride salt was prepared from (R)-3-tert-butyl 2-methyl thiazolidine-2,3-dicarboxylate following Method F (quantitative yield). 1H NMR (DMSO-d6): 5.66 (s, 1H), 3.95 (s, 3H), 3.74-3.70 (t, J=6.59 & 6.32 Hz, 2H), 3.39-3.37 (m, 2H). ES–MS: calcd. for $C_5H_9NO_2S$ (147.2). Found: 148.1[M+H].

Step 3: (R)-Methyl 3-(4'-propylbiphenylcarbonyl)thiazolidine-2-carboxylate was prepared from (R)-methyl thiazolidine-2-carboxylate following Method G (yield=92%) $^1$H NMR (DMSO-d$_6$): 8.24-8.17 (m, 2H), 7.98-7.80 (m, 4H), 7.51-7.48 (d, J=7.97 Hz, 2H), 5.77 (bs, 1H), 4.2 (bs, 1H), 4.09-4.01 (m, 1H), 3.9 (s, 3H), 3.37-3.33 (t, J=6.04-6.32 Hz, 2H), 2.81-2.76 (t, J=7.97 & 7.42 Hz, 2H), 1.87-1.74 (m, 2H), 1.12-1.07 (m, 3H). HPLC: Rt=7.16 min following Method R. ES–MS: calcd. for $C_{21}H_{23}NO_3S$ (369.48). Found: 370 [M+H].

Step 4: (R)—N-Hydroxy-3-(4'-propylbiphenylcarbonyl) thiazolidine-2-carboxamide was prepared from (R)-methyl 3-(4'-propylbiphenylcarbonyl)thiazolidine-2-carboxylate following Method H (yield=20%) 1H NMR (DMSO-d6): 10.9 (bs, 1H), 9.29 (bs, 1H), 7.94-7.91 (d, J=8.24 Hz, 2H), 7.83-7.80 (d, J=8.24 Hz, 4H), 7.51-7.48 (d, J=7.97 Hz, 2H), 5.72 (bs, 1H), 4.08 (bs, 1H), 3.77 (bs, 1H), 3.42-3.35 (m, 2H), 2.81-2.76 (t, J=7.42 & 7.69 Hz, 2H), 1.87-1.74 (m, 2H), 1.12-1.07 (t, J=7.42 & 7.14 Hz, 3H). HPLC: Rt=6.05 min following Method R. ES-MS: calcd. for $C_{20}H_{22}N_2O_3S$ (370.47). Found: 371.4 [M+H].

Example 19

Step 1: (R)-3-tert-Butyl 2-methyl thiazolidine-2,3-dicarboxylate was prepared from (R)-3-(tert-butoxycarbonyl)thiazolidine-2-carboxylic acid following Method B using the commercially available Boc-protected carboxylic acid (yield=94%) 1H NMR (DMSO-d6): 5.43-5.37 (d, 1H), 3.96 (bs, 2H), 3.87 (s, 2H), 3.27 (bs, 2H), 1.59-1.53 (d, 9H). HPLC: Rt=5.31 min following Method R. ES-MS: calcd. for $C_{10}H_{17}NO_4S$ (247.09). Found: 269.9 [M+Na].

Step 2: (R)-Methyl thiazolidine-2-carboxylate hydrochloride salt was prepared from (R)-3-tert-butyl 2-methyl thiazolidine-2,3-dicarboxylate following Method F (quantitative yield). 1H NMR (DMSO-d6): 5.66 (s, 1H), 3.95 (s, 3H), 3.74-3.70 (t, J=6.59 & 6.32 Hz, 2H), 3.39-3.37 (m, 2H). ES-MS: calcd. for $C_5H_9NO_2S$ (147.2). Found: 148.1 [M+H].

Step 3: (R)-Methyl 3-(4'-propylbiphenylcarbonyl)thiazolidine-2-carboxylate was prepared from (R)-methyl thiazolidine-2-carboxylate hydrochloride salt and 4-(p-n-propylphenyl)-benzoic acid following Method G (yield=92%) 1H NMR (DMSO-d6): 8.24-8.17 (m, 2H), 7.98-7.80 (m, 4H), 7.51-7.48 (d, J=7.97 Hz, 2H), 5.77 (bs, 1H), 4.2 (bs, 1H), 4.09-4.01 (m, 1H), 3.9 (s, 3H), 3.37-3.33 (t, J=6.04 & 6.32 Hz, 2H), 2.81-2.76 (t, J=7.97 & 7.42 Hz, 2H), 1.87-1.74 (m, 2H), 1.12-1.07 (m, 3H). HPLC: Rt=7.16 min following Method R. ES-MS: calcd. for $C_{21}H_{23}NO_3S$ (369.48). Found: 370 [M+H].

Step 4: (R)-Methyl 3-(4'-propylbiphenylcarbonyl)thiazolidinesulfone-2-carboxylate was prepared from (R)-methyl 3-(4'-propylbiphenylcarbonyl)thiazolidine-2-carboxylate following Method S (yield=30%). 1H NMR (DMSO-d6): 7.99-7.96 (d, J=8.24 Hz, 2H), 7.84-7.82 (d, J=7.97 Hz, 4H), 7.52-7.49 (d, J=7.97 Hz, 2H), 5.78 (bs, 1H), 4.34-4.2 (m, 1H), 4.04-3.95 (m, 1H), 3.99-3.98 (d, 3H), 3.87-3.58 (m, 1H), 2.81-2.76 (t, J=7.42 & 7.69 Hz, 2H), 1.87-1.75 (m, 2H), 1.12-1.07 (t, J=7.14 & 7.42 Hz, 3H). HPLC: Rt=6.87 min following Method R. ES-MS: calcd. for $C_{21}H_{23}NO_5S$ (401.48). Found: 424.2 [M+Na].

Step 5: (R)—N-(Benzyloxy)-3-(4'-propylbiphenylcarbonyl)thiazolidinesulfone-2-carboxamide was prepared from (R)-methyl 3-(4'-propylbiphenylcarbonyl)thiazolidinesulfone-2-carboxylate following Method I (yield=31%). HPLC: Rt=6.90 min following Method R. ES-MS: calcd. for $C_{27}H_{28}N_2O_5S$ (492.59). Found: 491.2 [M-H].

Step 6: (R)—N-Hydroxy-3-(4'-propylbiphenylcarbonyl) thiazolidinesulfone-2-carboxamide was prepared from (R)—N-(benzyloxy)-3-(4'-propylbiphenylcarbonyl)thiazolidinesulfone-2-carboxamide following Method P (yield=25%). The compound was isolated as containing ~50% of the opposite isomer as analyzed by HPLC using a chiral column. 1H NMR (DMSO-d6): 11.27 (bs, 1H), 9.46 (bs, 1H), 7.78-7.75 (d, J=8.24 Hz, 2H), 7.65-7.62 (d, J=7.97 Hz, 4H), 7.32-7.3 (d, J=7.97 Hz, 2H), 5.3 (bs, 1H), 4.06 (bs, 2H), 3.72 (bs, 1H), 3.52-3.45 (m, 3H), 2.62-2.57 (t, J=7.14 & 7.69 Hz, 2H), 1.68-1.55 (m, 2H), 0.93-0.88 (t, J=7.42 Hz, 3H). HPLC: Rt=5.897 min following Method R. ES-MS: calcd. for $C_{20}H_{22}N_2O_5S$ (402.47). Found: 425.3 [M+Na].

Example 20

Step 1: DL-3,3,3-Trifluoro-2-[(4'-propyl-biphenyl-4-carbonyl)-amino]-propionic acid methyl ester is prepared from 3,3,3-trifluoro-D,L-alanine and 4-(4-n-propylphenyl)benzoic acid following Method FF (yield=86%). 1H NMR (300 MHz, $CDCl_3$): 7.09-7.86 (m, 2H), 7.69-7.63 (m, 2H), 7.53-7.51 (m, 2H), 7.28-7.25 (m, 2H), 6.87 (d, J=9.00 Hz, 1H), 5.62-5.56 (m, 1H), 3.89 (s, 3H), 2.62 (t, J=6.00 Hz, 2H), 1.72-1.60 (m, 2H), 0.95 (t, J=9.00 Hz, 3H). $^{19}F$ NMR (282 MHz, $CDCl_3$): −70.87, −73.80.

Step 2: DL-4'-Propyl-biphenyl-4-carboxylic acid (2,2,2-trifluoro-1-hydroxycarbamoyl-ethyl)-amide is prepared from DL-3,3,3-Trifluoro-2-[(4'-propyl-biphenyl-4-carbonyl)-amino]-propionic acid methyl ester following Method GG (yield=56%). 1H NMR (300 MHz, DMSO-d6): 11.27 (s, 1H), 9.37 (s, 1H), 9.32 (d, J=9.00 Hz, 1H), 8.02 (d, J=9.00 Hz, 2H), 7.75 (d, J=6.00 Hz, 2H), 7.64 (d, J=9.00 Hz, 2H), 7.30 (d, J=9.00 Hz, 2H), 5.47-5.41 (m, 1H), 2.62-2.57 (m, 2H), 1.65-1.57 (m, 2H), 0.90 (t, J=9.00 Hz, 3H). $^{19}F$ NMR (282 MHz, DMSO-d6); −72.50. electrospray mass spectrometry (ESMS): m/z 379 [M−1]−. HPLC Rt: 6.42 min following Method R.

Example 21

Step 1: DL-3-Fluoro-2-[(4'-propyl-biphenyl-4-carbonyl)-amino]-propionic acid methyl ester is prepared from 3-fluoro-D,L-alanine and 4-(4-n-propylphenyl)benzoic acid following Method FF (yield=82%). 1H NMR (300 MHz, $CDCl_3$) 7.90-7.87 (m, 2H), 7.70-7.62 (m, 2H), 7.54-7.51 (m, 2H), 7.27-7.24 (m, 2H), 5.10-4.68 (m, 2H), 4.21-4.18 (m, 1H), 3.91-3.85 (m, 3H), 2.62 (t, J=9.00 Hz, 2H), 1.72-1.60 (m, 2H), 0.98-0.84 (m 3H). $^{19}F$ NMR (282 MHz, $CDCl_3$): −52.77-−53.22 (m).

Step 2: DL-4'-Propyl-biphenyl-4-carboxylic acid (2-fluoro-1-hydroxycarbamoyl-ethyl)-amide is prepared from DL-3-Fluoro-2-[(4'-propyl-biphenyl-4-carbonyl)-amino]-propionic acid methyl ester following Method GG (yield=42%). 1H NMR (300 MHz, DMSO-d6); 10.90 (s, 1H), 9.00 (s, 1H), 8.76 (d, J=7.8 Hz, 1H), 7.97 (d, J=9.00 Hz, 2H), 7.75 (d, J=8.10 Hz, 2H), 7.64 (d, J=8.10 Hz, 2H), 7.29 (d, J=9.00 Hz, 2H), 4.82-4.57 (m, 3H), 2.62-2.56 (m, 2H), 1.65-1.57 (m, 2H), 0.90 (t, J=7.20 Hz, 3H). $^{19}F$ NMR (282 MHz, DMSO); −73.77. ESMS: m/z 343 [M−1]−. HPLC Rt; 5.97 min following Method R.

Example 22

Step 1: DL-2-[(4'-Ethoxy-biphenyl-4-carbonyl)-amino]-3,3,3-trifluoro-propionic acid methyl ester is prepared from 3,3,3-trifluoro-D,L-alanine and 4-ethoxy-4'-biphenylcarboxylic acid following Method FF (yield=92%). 1H NMR (300 MHz, $CDCl_3$); −7.88-7.85 (m, 2H), 7.65-7.62 (m, 2H), 7.55-7.51 (m, 2H), 6.98-6.95 (m, 2H), 6.83 (d, J=9.00 Hz, 1H), 5.63-5.53 (m, 1H), 4.10-4.03 (m, 2H), 3.88 (s, 3H), 1.43 (t, J=7.20 Hz, 3H).). $^{19}F$ NMR (282 MHz, $CDCl_3$); −72.54.

Step 2: DL-4-Ethoxy-biphenyl-4-carboxylic acid (2,2,2-trifluoro-1-hydroxycarbamoyl-ethyl)-amide is prepared from DL-2-[(4'-Ethoxy-biphenyl-4-carbonyl)-amino]-3,3,3-trifluoro-propionic acid methyl ester following Method GG (yield=46%). 1H NMR (300 MHz, DMSO-d6): 11.27 (s, 1H), 9.37 (s, 1H), 9.27 (d, J=9.00 Hz, 1H), 7.99 (d, J=9.00 Hz, 2H), 7.73-7.66 (m, 4H), 7.02 (d, j=9.00 Hz, 1H), 5.44 (t, J=9.00 Hz, 1H), 4.10-4.03 (m, 2H), 1.34 (t, J=6.00 Hz, 3H). $^{19}$F NMR (282 MHz, DMSO-d6); −70.89, −73.76. ESMS: m/z 381 [M−1]. HPLC Rt: 5.25 min following Method R.

Example 23

Step 1: DL-2-[(3',5'-Difluoro-biphenyl-4-carbonyl)-amino]-3,3,3-trifluoro-propionic acid methyl ester is prepared from 3,3,3-trifluoro-D,L-alanine and 4-biphenyl-3',5'-difluorocarboxylic acid following Method FF I (yield=87%). 1H NMR (300 MHz, CDCl$_3$); 7.98-7.89 (m, 2H), 7.65-7.61 (m, 2H), 7.14-7.07 (m, 2H), 6.88-6.79 (m, 2H), 5.60-5.54 (m, 1H), 3.90 (s, 3H). $^{19}$F NMR (282 MHz, CDCl$_3$); −72.48, −109.16.

Step 2: DL-3',5'-Difluoro-biphenyl-4-carboxylic acid (2,2,2-trifluoro-1-hydroxycarbamoyl-ethyl)-amide is prepared from DL-2-[(3',5'-Difluoro-biphenyl-4-carbonyl)-amino]-3,3,3-trifluoro-propionic acid methyl ester following Method GG (yield=48%). 1H NMR (300 MHz, DMSO-d6); 11.24 (brs, 1H), 9.44-9.38 (m, 2H), 8.04 (d, J=9.00 Hz, 2H), 7.86 (d, J=9.00 Hz, 2H), 7.55-7.52 (m, 2H), 7.32-7.25 (m, 1H), 5.47-5.41 (m, 1H). $^{19}$F NMR (282 MHz, CDCl$_3$); −70.84, −109.36. ESMS: m/z 373 [M−1]−. HPLC Rt: 5.20 min following Method R.

Example 24

Step 1: DL-3,3,3-Trifluoro-2-(4-thiophen-3-yl-benzoylamino)-propionic acid methyl ester is prepared from 3,3,3-trifluoro-D,L-alanine and 4-(3-thienyl)benzoic acid following Method FF (yield=87%). 1H NMR (300 MHz, CDCl$_3$); 7.87-7.84 (m, 2H), 7.70-7.65 (m, 2H), 7.56-7.55 (m, 1H), 7.42-7.41 (m, 2H), 6.82 (d, J=9.30 Hz, 1H), 5.60-5.55 (m, 1H), 3.89 (s, 3H). $^{19}$F NMR (282 MHz, CDCl$_2$); −70.86

Step 2: DL-4-Thiophen-3-yl-N-(2,2,2-trifluoro-1-hydroxycarbamoyl-ethyl)-benzamide is prepared from DL-3,3,3-Trifluoro-2-(4-thiophen-3-yl-benzoylamino)-propionic acid methyl ester following Method GG (yield=51%). 1H NMR (300 MHz, DMSO-d6); 11.28 (s, 1H), 9.37 (s, 1H), 9.29 (d, J=9.00 Hz, 1H), 8.04 (s, 1H), 8.00-7.97 (m, 2H), 7.84-7.81 (m, 2H) 7.67-7.65 (m, 2H), 5.47-5.41 (m, 1H), $^{19}$F NMR (282 MHz, DMSO-d6); −72.53. ESMS: m/z 343 [M−1]−. HPLC Rt: 4.78 min following Method R.

Example 25

DL-methyl-3,3,3-triflurobiphenyl-4-ylcarboxamido)propanoate is prepared from 3,3,3-trifluoro-D,L-alanine and 4'-fluoro-biphenyl-4-carboxylic acid following Method FF. This material was used without any further purification.

DL-4'-fluoro-N-(1,1,1-trifluoro-3-(hydroxyamino)-3-oxopropan-2-yl)biphenyl-4-carboxamide is prepared from DL-methyl-3,3,3-triflurobiphenyl-4-ylcarboxamido)propanoate following Method GG (yield=33%). 1H NMR (300 MHz, DMSO-d6); 11.28 (s, 1H), 9.38-9.33 (m, 2H), 8.02 (d, J=9.00 Hz, 2H), 7.81-7.75 (m, 4H), 7.35-7.29 (m, 2H), 5.47-5.41 (m, 1H). $^{19}$F NMR (282 MHz, DMSO-d6); −70.88, −73.82, −114.55. ESMS: m/z 355 [M−1]−. HPLC Rt: 5.40 min following Method R.

Example 26

Step 1: (S)-Methyl 4-(methylthio)-2-(4'-propylbiphenyl-4-ylcarboxamido)butanoate was prepared from (S)-methyl 2-amino-4-(methylthio)butanoate hydrochloride salt and 4-(p-n-propylphenyl)-benzoic acid following Method G (yield=87%). The methyl ester was available commercially. 1H NMR (DMSO-d6): 8.81-8.79 (d, J=7.42 Hz, 1H), 7.97-7.94 (d, J=8.52 Hz, 2H), 7.78-7.75 (d, J=8.52 Hz, 2H), 7.66-7.63 (d, J=8.24 Hz, 2H), 7.32-7.29 (d, 8.24 Hz, 2H), 4.63-4.56 (dd, J=7.97 & 7.89 Hz, 1H), 3.65 (s, 3H), 2.61-2.56 (t, J=7.42 & 6.87 Hz, 4H), 2.1-2.03 (m, 2H), 2.06 (s, 3H), 1.67-1.55 (m, 2H), 0.93-0.88 (t, J=7.14 & 7.42 Hz, 3H). HPLC: Rt=7.18 min following Method R. ES−MS: calcd. for C$_{22}$H$_{27}$NO$_3$S (385.17). Found: 386.1 [M+H].

Step 2: (S)—N-(1-(Hydroxyamino)-4-(methylthio)-1-oxobutan-2-yl)-4'-propylbiphenyl-4-carboxamide was prepared from (S)-methyl 4-(methylthio)-2-(4'-propylbiphenyl-4-ylcarboxamido)butanoate following Method H (yield=10%) 1H NMR (DMSO-d6): 10.92 (s, 1H), 9.04 (s, 1H), 8.75-8.72 (d, J=7.69 Hz, 1H), 8.17-8.15 (d, J=7.97 Hz, 2H), 7.95-7.92 (d, J=8.24 Hz, 2H), 7.85-7.82 (d, J=8.24 Hz, 2H), 7.51-7.48 (d, 8.24 Hz, 2H), 4.67-4.62 (m, 1H), 3.42-2.74 (m, 4H), 2.25 (s, 3H), 2.2-2.15 (t, 6.04-8.24 Hz, 2H), 1.86-1.77 (m, 2H), 1.13-1.08 (t, J=7.42 Hz, 3H). HPLC: Rt=6.26 min following Method R. ES−MS: calcd. for C$_{21}$H$_{26}$N$_2$O$_3$S (386.51). Found: 409.2 [M+Na].

Example 27

Step 1: (S)-Methyl 4-(methylthio)-2-(4'-propylbiphenyl-4-ylcarboxamido)butanoate was prepared from (S)-methyl 2-amino-4-(methylthio)butanoate hydrochloride salt and 4-(p-n-propylphenyl)-benzoic acid following Method G (yield=87%) 1H NMR (DMSO-d6): 8.81-8.79 (d, J=7.42 Hz, 1H), 7.97-7.94 (d, J=8.52 Hz, 2H), 7.78-7.75 (d, J=8.52 Hz, 2H), 7.66-7.63 (d, J=8.24 Hz, 2H), 7.32-7.29 (d, 8.24 Hz, 2H), 4.63-4.56 (dd, J=7.97 & 7.69 Hz, 1H), 3.65 (s, 3H), 2.61-2.56 (t, J=7.42 & 6.87 Hz, 4H), 2.1-2.03 (m, 2H), 2.06 (s, 3H), 1.67-1.55 (m, 2H), 0.93-0.88 (t, J=7.14 & 7.42 Hz, 3H). HPLC: Rt=7.18 min following Method R. ES−MS: calcd. for C$_{22}$H$_{27}$NO$_3$S (385.17). Found: 386.1 [M+H].

Step 2: (S)-Methyl 4-(methylsulfone-2-(4'-propylbiphenyl-4-ylcarboxamido)butanoate was prepared from (S)-methyl 4-(methylthio)-2-(4'-propylbiphenyl-4-ylcarboxamido)butanoate following Method S (yield=75%). 1H NMR (DMSO-d6): 9.1-9.08 (d, J=7.69 Hz, 1H), 8.2-8.17 (d, J=8.52 Hz, 2H), 7.97-7.94 (d, J=8.24 Hz, 2H), 7.86-7.83 (d, J=7.97 Hz, 2H), 7.51-7.5 (d, 7.69 Hz, 2H), 4.82-4.81 (m, 1H), 3.87 (s, 3H), 3.51-3.43 (m, 2H), 3.2 (s, 3H), 2.81-2.77 (t, J=7.42 & 7.14 Hz, 2), 2.47-2.41 (m, 2H), 1.85-1.77 (m, 2H), 1.13-1.08 (t, J=7.42 Hz, 3H). HPLC: Rt=6.49 min following Method R. ES−MS: calcd. for C$_{22}$H$_{27}$NO$_5$S (417.52). Found: 418.3 [M+H].

Step 3: (S)—N-(1-(Benzyloxyamino)-4-(methylsulfone)-1-oxobutan-2-yl)-4'-propylbiphenyl-4-carboxamide was prepared from (S)-methyl 4-(methylsulfone)-2-(4'-propylbiphenyl-4-ylcarboxamido)butanoate following Method I (yield=61%). 1H NMR (DMSO-d6): 11.59 (s, 1H), 8.89-8.86 (d, J=7.69 Hz, 1H), 8.17-8.15 (d, J=8.24 Hz, 2H), 7.98-7.95 (d, J=7.97 Hz, 2H), 7.85-7.83 (d, J=7.97 Hz, 2H), 7.6-7.5 (d, 7.69 Hz, 7H), 5 (bs, 2H), 4.66-4.64 (m, 1H), 3.36-3.31 (t, J=7.14 & 8.79 Hz, 2H), 3.2 (bs, 3H), 2.81-2.76 (t, J=7.14 & 7.69 Hz, 2H), 2.35-2.33 (m, 2H), 1.85-1.75 (m, 2H), 1.13-1.08 (t, J=7.42 Hz, 3H). HPLC: Rt=6.69 min following Method R. ES−MS: calcd. for C$_{28}$H$_{32}$N$_2$O$_5$S (508.63). Found: 509.3 [M+H].

Step 4: (S)—N-(1-(Hydroxyamino)-4-(methylsulfone)-1-oxobutan-2-yl)-4'-propylbiphenyl-4-carboxamide was prepared from (S)—N-(1-(benzyloxyamino)-4-(methylsulfone)-1-oxobutan-2-yl)-4'-propylbiphenyl-4-carboxamide following Method P (yield=15%). 1H NMR (DMSO-d6): 10.98 (s, 1H), 9.12 (s, 1H), 8.84-8.82 (d, J=7.97 Hz, 1H), 8.19-8.16 (d, J=8.24 Hz, 2H), 7.96-9.94 (d, J=8.24 Hz, 2H), 7.86-7.83 (d, J=8.24 Hz, 2H), 7.51-7.49 (d, 7.97 Hz, 2H), 4.72-4.64 (dd, J=7.97 & 7.42 Hz, 1H), 3.37-3.32 (t, J=7.97 Hz, 2H), 3.2 (bs, 3H), 2.82-2.73 (m, 2H), 2.35-2.26 (m, 2H), 1.85-1.75 (m, 2H), 1.13-1.08 (t, J=7.42 & 7.14 Hz, 3H). HPLC: Rt=5.827 min following Method R. ES–MS: calcd. for $C_{21}H_{26}N_2O_5S$ (418.51). Found: 417.2 [M–H].

Example 28

Step 1: (S)-Methyl 2-(3,3-dimethylbutanamido)-3-(methylthio)propanoate was prepared from (S)-2-(3,3-dimethylbutanamido)-3-(methylthio)propanoic acid following Method B (yield=78%-80%). 1H NMR (DMSO-d6): 7.31-7.28 (d, J=8.24 Hz, 1H) 4.18-4.11 (dd, J=7.97 & 8.24 Hz, 1H), 3.63 (s, 3H), 2.83-2.50 (m, 2H), 2.1-2.05 (d, J=1.37 Hz, 3H), 1.37 (s, 9H). HPLC: Rt=5 min following Method R. ES–MS: calcd. for $C_{10}H_{19}NO_4S$ (249.1). Found: 272 [M+Na].

Step 2: (S)-Methyl 2-amino-3-(methylthio)propanoate hydrochloride salt was prepared from (S)-methyl 2-(3,3-dimethylbutanamido)-3-(methylthio)propanoate following Method F (quantitative yield). 1H NMR (DMSO-d6): 8.79 (bs, 2H) 4.29-4.25 (t, J=5.77 Hz, 1H), 3.75 (s, 3H), 3.03-3.01 (d, J=5.77 Hz, 2H), 2.1 (s, 3H). ES–MS: calcd. for $C_5H_{11}NO_2S$ (149.05). Found: 150.2 [M+H].

Step 3: (S)-Methyl 3-(methylthio)-2-(4'-propylbiphenyl-4-ylcarboxamido)propanoate was prepared from (S)-methyl 2-amino-3-(methylthio)propanoate hydrochloride salt and 4-(p-n-propylphenyl)-benzoic acid following Method G (yield=78%-80%). 1H NMR (DMSO-d6): 9.11-9.08 (d, J=7.97 Hz, 1H), 8.16-8.14 (d, J=7.69 Hz, 2H), 7.98-7.96 (d, J=8.52 Hz, 2H), 7.86-7.83 (d, J=7.69 Hz, 2H), 7.51-7.49 (d, 7.69 Hz, 2H), 4.9-4.82 (m, 1H), 3.86 (s, 3H), 3.2-3.08 (m, 2H), 2.82-2.76 (t, J=7.69 & 7.42 Hz, 2H), 2.29 (s, 3H), 1.85-1.75 (m, 2H), 1.13-1.08 (t, J=7.14 & 7.42 Hz, 3H). HPLC: Rt=7.12 min following Method R. ES–MS: calcd. for $C_{21}H_{25}NO_3S$ (371.16). Found: 394.1 [M+Na].

Step 4: (S)—N-(1-(Hydroxyamino)-3-(methylthio)-1-oxopropan-2-yl)-4'-propylbiphenyl-4-carboxamide was prepared from (S)-methyl 3-(methylthio)-2-(4'-propylbiphenyl-4-ylcarboxamido)propanoate following Method H (yield=20%). 1H NMR (DMSO-d6): 11.05 (bs, 1H), 9.14-9.13 (d, J=1.1 Hz, 1H), 8.83-8.80 (d, J=8.52 Hz, 1H), 8.17-8.15 (d, J=8.24 Hz, 2H), 7.96-7.93 (d, J=8.52 Hz, 2H), 7.8-7.82 (d, 8.24 Hz, 2H), 7.51-7.48 (d, J=7.97 Hz, 2H), 4.81-4.73 (dd, J=7.97 Hz, 1H), 3.05-3.02 (m, 2H), 2.81-2.76 (t, J=7.42 & 7.69 Hz, 2H), 2.28 (s, 3H), 1.87-1.75 (m, 2H), 1.13-1.08 (t, J=7.42 & 7.14 Hz, 3H). HPLC: Rt=6.19 min following Method R. ES–MS: calcd. for $C_{20}H_{24}N_2O_3S$ (372.49). Found: 395.2 [M+Na].

Example 29

Step 1: (S)-methyl 2-(3,3-dimethylbutanamido)-3-(methylthio)propanoate was prepared from (S)-2-(3,3-dimethylbutanamido)-3-(methylthio)propanoic acid following Method B (yield=78%-80%): 1H NMR (DMSO-d6): 7.31-7.28 (d, J=8.24 Hz, 1H) 4.18-4.11 (dd, J=7.97 & 8.24 Hz, 1H), 3.63 (s, 3H), 2.83-2.50 (m, 2H), 2.1-2.05 (d, J=1.37 Hz, 3H), 1.37 (s, 9H).

Step 2: (S)-Methyl 2-amino-3-(methylthio)propanoate hydrochloride salt was prepared from (S)-methyl 2-(3,3-dimethylbutanamido)-3-(methylthio)propanoate following Method F (quantitative yield). 1H NMR (DMSO-d6): 8.79 (bs, 2H) 4.29-4.25 (t, J=5.77 Hz, 1H), 3.75 (s, 3H), 3.03-3.01 (d, J=5.77 Hz, 2H), 2.1 (s, 3H). ES–MS: calcd. for $C_5H_{11}NO_2S$ (149.05). Found: 150.2 [M+H].

Step 3: (S)-Methyl 3-(methylthio)-2-(4'-propylbiphenyl-4-ylcarboxamido)propanoate was prepared from (S)-methyl 2-amino-3-(methylthio)propanoate hydrochloride salt and 4-(p-n-propylphenyl)-benzoic acid following Method G (yield=78%-80%) 1H NMR (DMSO-d6): 9.11-9.08 (d, J=7.97 Hz, 1H), 8.16-8.14 (d, J=7.69 Hz, 2H), 7.98-7.96 (d, J=8.52 Hz, 2H), 7.86-7.83 (d, J=7.69 Hz, 2H), 7.51-7.49 (d, 7.69 Hz, 2H), 4.9-4.82 (m, 1H), 3.86 (s, 3H), 3.2-3.08 (m, 2H), 2.82-2.76 (t, J=7.69 & 7.42 Hz, 4H), 2.29 (s, 3H), 1.85-1.75 (m, 2H), 1.13-1.08 (t, J=7.14 & 7.42 Hz, 3H). HPLC: Rt=7.12 min following Method R. ES–MS: calcd. for $C_{21}H_{25}NO_3S$ (371.16). Found: s394.1 [M+Na].

Step 3: (S)-Methyl 3-(methylsulfone)-2-(4'-propylbiphenyl-4-ylcarboxamido)propanoate was prepared from S)-methyl 3-(methylthio)-2-(4'-propylbiphenyl-4-ylcarboxamido)propanoate following Method S (yield=46%). 1H NMR (DMSO-d6): 9.39-9.37 (d, J=7.97 Hz, 1H), 8.14-8.12 (d, J=8.24 Hz, 2H), 7.99-7.96 (d, J=8.24 Hz, 2H), 7.86-7.83 (d, J=7.97 Hz, 2H), 7.52-7.49 (d, 8.24 Hz, 2H), 5.16-5.09 (dd, J=7.14 & 6.59 Hz, 1H), 3.94-3.92 (d, J=6.59 Hz, 2H), 3.88 (s, 3H), 3.25 (s, 3H), 2.81-2.76 (t, J=7.42 & 7.69 Hz, 2H), 1.87-1.75 (m, 2H), 1.13-1.08 (t, J=7.42 & 7.69 Hz, 3H). HPLC: Rt=6.44 min following Method R. ES–MS: calcd. for $C_{21}H_{25}NO_5S$ (403.15). Found: 404.3 [M+H].

Step 5: (S)—N-(1-(Benzyloxyamino)-3-(methylsulfone)-1-oxopropan-2-yl)-4'-propylbiphenyl-4-carboxamide was prepared from (S)-methyl 3-(methylsulfone)-2-(4'-propylbiphenyl-4-ylcarboxamido)propanoate following Method I (yield=55%). 1H NMR (DMSO-d6): 11.6 (bs, 1H), 8.94-8.92 (d, J=8.52 Hz, 1H), 7.97-7.95 (d, J=8.24 Hz, 2H), 7.79-7.76 (d, J=8.24 Hz, 2H), 7.67-7.64 (d, J=7.97 Hz, 2H), 7.4-7.3 (m, 7H), 4.92-4.91 (m, 1H), 4.79 (bs, 2H), 3.65-3.59 (m, 1H), 3.32 (bs, 1H), 3.02 (s, 3H), 2.62-2.57 (t, J=7.14 & 7.69 Hz, 2H), 1.65-1.58 (m, 2H), 0.93-0.88 (t, J=7.42 & 7.14 Hz, 3H). HPLC: Rt=6.8 min following Method R. ES–MS: calcd. for $C_{27}H_{30}N_2O_5S$ (494.16). Found: 493.2 [M–H].

Step 6: (S)—N-(1-(Hydroxyamino)-3-(methylsulfone)-1-oxopropan-2-yl)-4'-propylbiphenyl-4-carboxamide was prepared from (S)—N-(1-(benzyloxyamino)-3-(methylsulfone)-1-oxopropan-2-yl)-4'-propylbiphenyl-4-carboxamide following Method P (yield=20%). 1H NMR (DMSO-d6): 10.95 (bs, 1H), 9.01 (bs, 1H), 8.89-8.86 (d, J=8.52 Hz, 1H), 7.97-7.94 (d, J=8.24 Hz, 2H), 7.78-7.75 (d, J=8.52 Hz, 2H), 7.66-7.63 (d, J=8.24 Hz, 2H), 7.32-7.3 (d, J=7.97 Hz, 2H), 4.94 (bs, 1H), 3.71-3.55 (m, 2H), 3.02 (s, 3H), 2.62-2.57 (t, J=7.14 & 7.97 Hz, 2H), 1.65-1.58 (dd, J=7.14 & 7.42 Hz, 2H), 0.93-0.88 (t, J=7.14 & 7.42 Hz, 3H). HPLC: Rt=5.804 min following Method R. ES–MS: calcd. for $C_{20}H_{24}N_2O_5S$ (404.485). Found: 403.2 [M–H].

Example 30

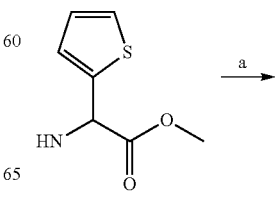

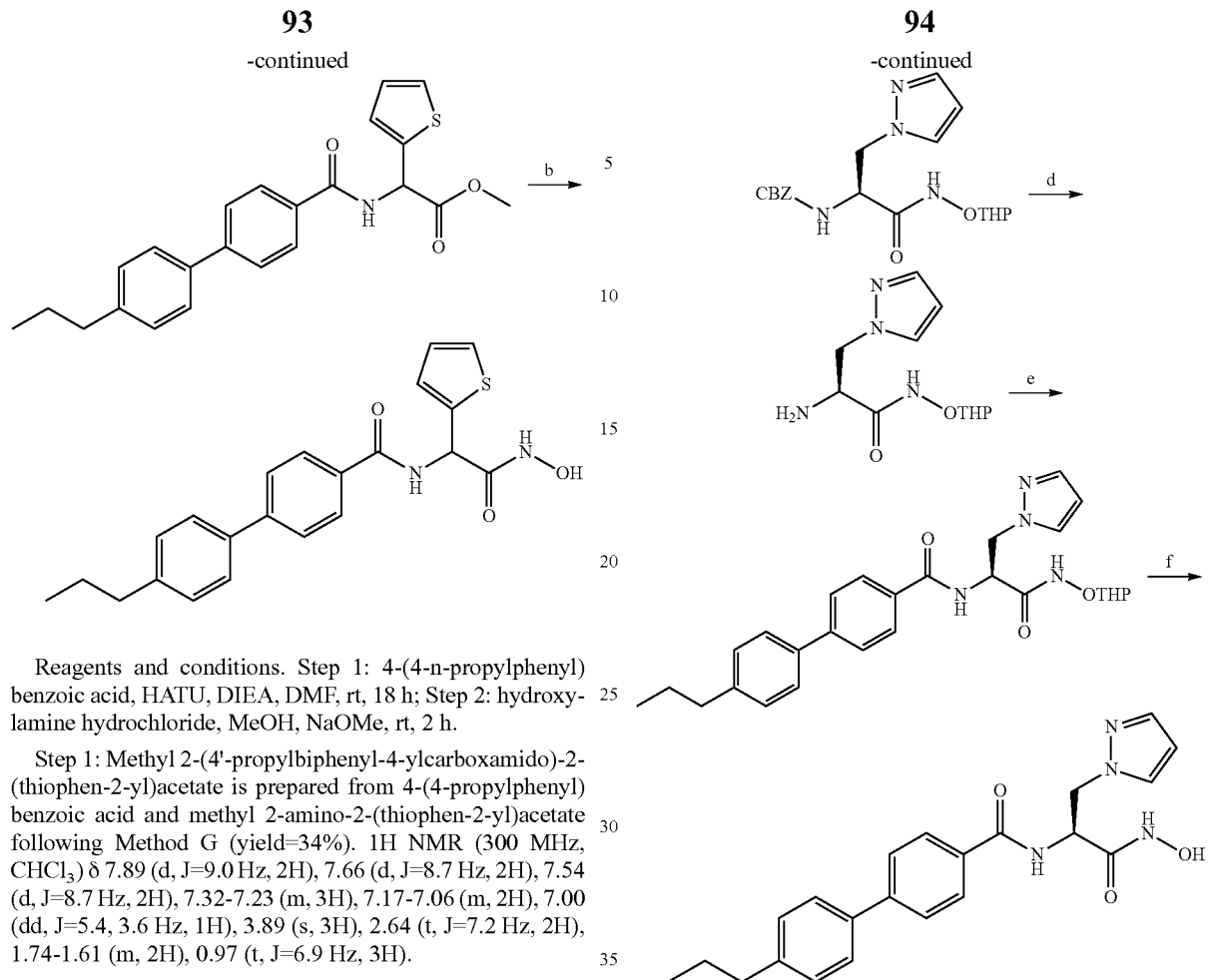

Reagents and conditions. Step 1: 4-(4-n-propylphenyl)benzoic acid, HATU, DIEA, DMF, rt, 18 h; Step 2: hydroxylamine hydrochloride, MeOH, NaOMe, rt, 2 h.

Step 1: Methyl 2-(4'-propylbiphenyl-4-ylcarboxamido)-2-(thiophen-2-yl)acetate is prepared from 4-(4-propylphenyl)benzoic acid and methyl 2-amino-2-(thiophen-2-yl)acetate following Method G (yield=34%). 1H NMR (300 MHz, CHCl$_3$) δ 7.89 (d, J=9.0 Hz, 2H), 7.66 (d, J=8.7 Hz, 2H), 7.54 (d, J=8.7 Hz, 2H), 7.32-7.23 (m, 3H), 7.17-7.06 (m, 2H), 7.00 (dd, J=5.4, 3.6 Hz, 1H), 3.89 (s, 3H), 2.64 (t, J=7.2 Hz, 2H), 1.74-1.61 (m, 2H), 0.97 (t, J=6.9 Hz, 3H).

Step 2: N-(2-(Hydroxyamino)-2-oxo-1-(thiophen-2-yl)ethyl)-4'-propylbiphenyl-4-carboxamide is prepared from methyl 2-(4'-propylbiphenyl-4-ylcarboxamido)-2-(thiophen-2-yl)acetate following Method H (yield=9%). 1H NMR (300 MHz, DMSO-d6) δ 11.03 (s, 1H), 9.19-8.99 (m, 2H), 8.00 (d, J=8.4 Hz, 2H), 7.75 (d, J=8.4 Hz, 2H), 7.65 (d, J=8.1 Hz, 2H), 7.47 (d, J=5.1 Hz, 1H), 7.31 (d, J=8.4 Hz, 2H), 7.15 (d, J=3.3 Hz, 1H), 7.00 (dd, J=5.1, 3.3 Hz, 1H), 5.86 (d, J=8.1 Hz, 1H), 2.63-2.42 (m, 3H), 1.69-1.55 (m, 2H), 0.91 (t, J=7.2 Hz, 3H); ESI(+) calcd. for C$_{22}$H$_{23}$N$_2$O$_3$S (305.14). Found 395.5

Example 31

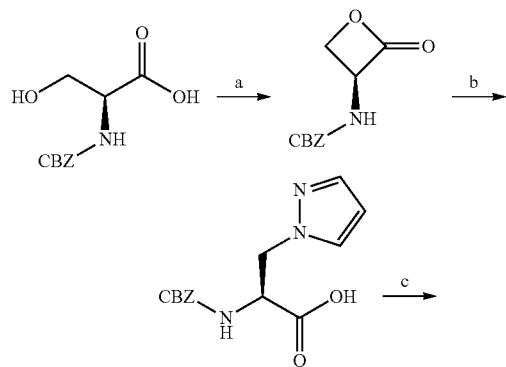

Reagents and conditions. Step 1: DIAD, Ph$_3$P, THF, −78° C., 3 h 50 min; Step 2: pyrazole, acetonitrile (ACN), 55° C., 24 h; Step 3: HATU, DIEA, DMF, O-(tetrahydro-2H-pyran-2-yl)hydroxylamine, rt, 18 h; Step 4: 10% Pd/C, EtOH, H$_2$, rt, 8 h; Step 5: 4-(4-n-propylphenyl)benzoic acid, HATU, DIEA, DMF, rt, 18 h; Step 6: TFA, DCM, rt, 2 h.

Step 1: (Steps 1 and 2 are done similar to that described in Organic Syntheses, Coll. Vol. 9, p. 58-63) To a solution of triphenylphosphine (27.7 g, 106 mmol) in THF (500 mL) at −78° C., DIAD (20.8 mL, 106 mmol) was added dropwise. The mixture is stirred at −78° C. for 20 min. A solution of N-(benzyloxycarbonyl)-L-serine (25.3 g, 106 mmol) in THF (150 mL) is added to the reaction mixture. The reaction mixture is stirred for an additional 30 min at −78° C., warmed to rt, and stirred for an additional 3 h. The reaction mixture is concentrated in vacuo, dissolved in ether, and filtered. The filtrate was concentrated in vacuo, and the residue is purified by column chromatography (SiO$_2$, gradient 10%-40% ethyl acetate in hexanes). This gave 8.0 g of N-(benzyloxycarbonyl)-L-serine β-lactone. 1H NMR (300 MHz, DMSO-d6) δ 7.73-7.43 (m, 5H), 5.80-5.66 (m, 1H), 5.48-5.28 (m, 3H), 4.77-4.89 (m, 2H).

Step 2: N-(Benzyloxycarbonyl)-L-serine β-lactone (1.5 g, 6.8 mmol), pyrazole (0.49 g, 7.2 mmol), and acetonitrile (25 mL) are combined and stirred for 12 h at 55° C. An additional charge of pyrazole (0.25 g, 3.6 mmol) is added to the reaction and stirred for an additional 12 h. The reaction mixture is concentrated in vacuo. The residue is dissolved in sodium hydroxide solution (1 M), and washed with DCM. The aqueous solution was neutralized with HCl solution (1 M) to precipitate N-(benzyloxycarbonyl)-p-(pyrazol-1-yl)-L-alanine (1.1 g). The compound is used in the next reaction without further purification.

Step 3: (2S)-Tetrahydro-2H-pyran-2-yl 2-(benzyloxycarbonylamino)-3-(1H-imidazol-1-yl)propanoate is prepared from N-(benzyloxycarbonyl)-p-(pyrazol-1-yl)-L-alanine and O-(tetrahydro-2H-pyran-2-yl)hydroxylamine following Method G. ESI(+) calcd. for $C_{19}H_{25}N_4O_5$ (389.18). Found 389.2.

Step 4: (2S)-Tetrahydro-2H-pyran-2-yl 2-amino-3-(1H-imidazol-1-yl)propanoate is prepared from (2S)-tetrahydro-2H-pyran-2-yl 2-(benzyloxycarbonylamino)-3-(1H-imidazol-1-yl)propanoate following Method Z. ESI(−) calcd. for $C_{11}H_{17}N_4O_3$ (253.13). Found 253.2.

Step 5: (2S)-Tetrahydro-2H-pyran-2-yl 3-(1H-imidazol-1-yl)-2-(4'-propylbiphenyl-4-ylcarboxamido)propanoate is prepared from (2S)-tetrahydro-2H-pyran-2-yl 2-amino-3-(1H-imidazol-1-yl)propanoate and 4-(4-propylphenyl)benzoic acid following Method G. ESI(+) calcd. for $C_{27}H_{33}N_4O_4$ (477.25). Found 477.1.

Step 6: (S)-3-(1H-imidazol-1-yl)-2-(4'-propylbiphenyl-4-ylcarboxamido)propanoic acid is prepared from (2S)-tetrahydro-2H-pyran-2-yl 3-(1H-imidazol-1-yl)-2-(4'-propylbiphenyl-4-ylcarboxamido)propanoate following Method AA. The compound is dissolved in DMSO, and purified by preparative-HPLC (yield—6%). 1H NMR (300 MHz, DMSO-d6) δ 10.98 (s, 1H), 9.14-8.62 (m, 1H), 8.17-7.20 (m, 11H), 6.34-6.09 (m, 1H), 5.00-4.33 (m, 3H), 2.75-2.36 (m, 2H), 1.81-1.39 (m, 2H), 1.02-0.73 (m, 3H); ESI(+) calcd. for $C_{22}H_{25}N_4O_3$ (393.19). Found 393.1.

Example 32

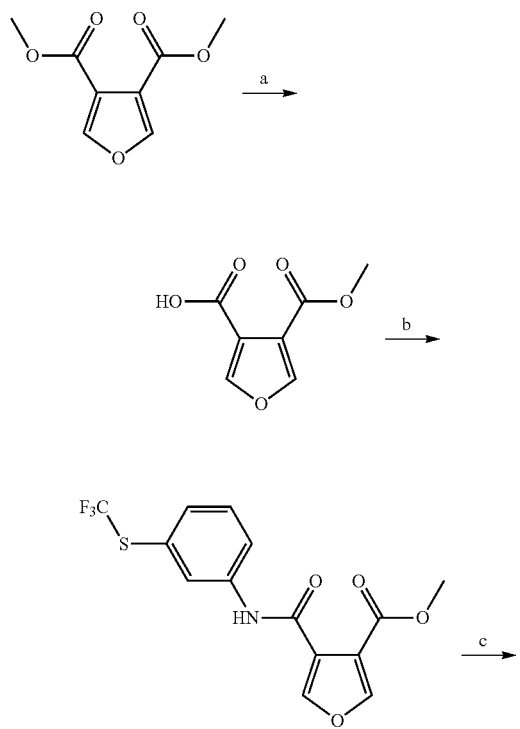

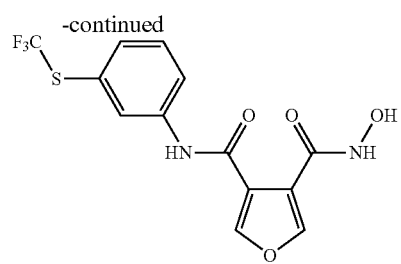

Reagents and conditions. Step 1: NaOH water, MeOH, 4° C., 18 h; Step 2: HATU, DIEA, DMF, 3-(trifluoromethylthio) aniline, rt, 18 h; Step 3: hydroxylamine hydrochloride, MeOH, NaOMe, rt, 2 h.

Step 1: 4-(Methoxycarbonyl)furan-3-carboxylic acid is prepared from dimethyl furan-3,4-dicarboxylate following Method BB (yield=50%). 1H NMR (300 MHz, DMSO-d6) δ 8.40-8.28 (m, 2H), 3.78 (s, 3H).

Step 2: Methyl 4-(3-(trifluoromethylthio)phenylcarbamoyl)furan-3-carboxylate is prepared from 4-(methoxycarbonyl)furan-3-carboxylic acid and 3-(trifluoromethylthio) aniline following Method G (yield=78%). 1H NMR (300 MHz, CHCl3) δ 11.66 (s, 1H), 8.29 (s, 1H), 8.22-8.09 (m, 1H), 7.96-7.82 (m, 2H), 7.50-7.37 (m, 2H), 3.99 (s, 3H); ESI(−) calcd. for $C_{14}H_9F_3NO_4S$ (344.02). Found 344.0

Step 3: Methyl 4-(3-(trifluoromethylthio)phenylcarbamoyl)furan-3-carboxylate is prepared from N3-hydroxy-N4-(3-(trifluoromethylthio)phenyl)furan-3,4-dicarboxamide following Method H. The compound was purified by preparative-HPLC (yield=18%). 1H NMR (300 MHz, DMSO-d6) δ 12.22 (s, 1H), 11.61 (s, 1H), 9.54 (s, 1H), 8.47 (s, 1H), 8.28 (s, 1H), 8.13 (s, 1H), 7.84-7.39 (m, 3); ESI(−) calcd. for $C_{13}H_8F_3N_2O_4S$ (345.02). Found 345.0.

Example 33

Step 1: (S)-(tert-Butoxycarbonyl)thiazolidine-2-carboxylic acid was prepared following Method A using the commercially available (S)-2-thiazolidinecarboxylic acid (yield=96%). 1H NMR (DMSO-d6): 5.29-5.22 (bs, 1H), 4.52 (bs, 2H), 3.64-3.52 (m, 2H), 1.55 (bs, 9H). ES−MS: calcd. for $C_9H_{15}NO_4S$ (233.07). Found: 256.2 [M+Na].

Step 2: (S)-tert-Butyl 2-(benzyloxycarbamoyl)thiazolidine-3-carboxylate was prepared from and O-benzyl hydroxylamine following Method G (yield=67%). 1H NMR (DMSO-d6): 11.474 (bs, 1H), 7.6-7.55 (m, 5H), 4.97 (bs, 1H), 3.94-3.8 (m, 2H), 3.44-3.23 (m, 2H), 1.58-1.53 (m, 9H). HPLC: Rt=5.293 min following Method R. ES−MS: calcd. for $C_{16}H_{22}N_2O_4S$ (338.13). Found: 337.2 [M−H].

Step 3: (S)—N-(Benzyloxy)thiazolidine-2-carboxamide hydrochloride salt was prepared from (S)-tert-butyl 2-(benzyloxycarbamoyl)thiazolidine-3-carboxylate following Method F (quantitative yield) 1H NMR (DMSO-d6): 11.91 (bs, 1H), 7.4-7.33 (m, 5H), 5.07 (s, 1H), 4.82 (m, 2H), 3.67-3.56 (m, 2H), 3.55-3.46 (m, 2H), 3.2-3.15 (m, 2H). ES−MS: calcd. for $C_{11}H_{14}N_2O_2S$ (238.08). Found: 239.1 [M+H].

Step 4: (S)—N-(Benzyloxy)3-(4'-ethoxybiphenylcarbonyl)-thiazolidine-2-carboxamide was prepared from (S)—N-(benzyloxy)thiazolidine-2-carboxamide hydrochloride salt and 3-(4'-ethoxybiphenyl)-carboxylic acid following Method G (yield=48%). 1H NMR (DMSO-d6): 11.56 (bs, 1H), 7.84-7.81 (d, J=8.52 Hz, 6H), 7.58-7.55 (t, J=4.67 & 5.49 Hz, 5H), 7.23-7.20 (d, J=8.79 Hz, 2H), 5.67 (bs, 1H), 4.98 (s, 2H), 4.27-4.18 (m, 3H), 4.08 (bs, 1H), 3.45-3.25 (m, 2H), 1.56-

1.51 (t, J=7.14 & 6.87 Hz, 3H). HPLC: Rt=6.406 min following Method R. ES–MS: calcd. for $C_{26}H_{26}N_2O_4S$ (462.16). Found: 461.2 [M–H].

Step 5: (S)—N-(Benzyloxy)3-(4'-ethoxybiphenylcarbonyl)-thiazolidinesulfone-2-carboxamide was prepared from (S)—N-(benzyloxy)3-(4'-ethoxybiphenylcarbonyl)-thiazolidine-2-carboxamide following Method S (yield=48%). 1H NMR (DMSO-d6): 11.86 (bs, 1H), 8.08-7.86 (m, 6H), 7.75-7.55 (m, 5H), 7.23-7.20 (d, J=8.79 Hz, 2H), 5.45 (bs, 1H), 5.21 (s, 2H), 4.27-4.24 (d, J=7.14 Hz, 4H), 3.96 (bs, 1H), 3.71 (m, 1H), 1.55-1.51 (t, J=6.87 Hz, 3H). HPLC: Rt=6.317 min following Method R. ES–MS: calcd. for $C_{26}H_{26}N_2O_6S$ (494.15). Found: 493.2 [M–H].

Step 6: (S)-3-(4'-Ethoxybiphenylcarbonyl)-N-hydroxythiazolidinesulfone-2-carboxamide was prepared from (S)—N-(benzyloxy)3-(4'-ethoxybiphenylcarbonyl)-thiazolidinesulfone-2-carboxamide following Method P (yield=20%). 1H NMR (DMSO-d6): 11.26 (bs, 1H), 9.46 (bs, 1H), 7.9-7.51 (m, 6H), 7.05-7.02 (d, J=8.79 Hz, 2H), 5.3 (bs, 1H), 4.11-4.04 (dd, J=6.87 Hz, 3H), 3.76-3.71 (m, 2H), 3.51-3.38 (m, 1H), 1.37-1.32 (t, J=7.14 & 6.87 Hz, 3H). HPLC: Rt=5.154 min following Method R. ES–MS: calcd. for $C_{19}H_{20}N_2O_6S$ (404.44). Found: 403.2 [M–H].

Example 34

Step 1: To a stirred 0° C. suspension of (2S,3S)-3-hydroxypyrrolidine-2-carboxylic acid (5.1 g, 38.9 mmol, Acros) in anhydrous MeOH (100 mL) was added dropwise $SOCl_2$ (5.6 mL, 77.2 mmol) after 1 h dissolution of starting material was complete. The reaction mixture was stirred at rt 24 h then evaporated under reduced pressure. The resulting residue was triturated with anhydrous $Et_2O$, filtered, washed with additional $Et_2O$ and dried in vacuo to furnish the product (7.1 g, quantitative yield). ES+MS: calcd. for $C_6H_{11}NO_3$ (145.07). Found: 146.0 [M+H].

Step 2: To a stirred 0° C. suspension of (2S,3S)-methyl 3-hydroxypyrrolidine-2-carboxylic acid (2.0 g, 11.0 mmol), 4'-ethylbiphenylcarboxylate (2.74 g, 12.1 mmol, Acros), HOBt (1.63 g, 12.1 mmol) and DIEA (3.71 mL, 22.0 mmol), in anhydrous DCM (50 mL) was added EDC (2.6 g, 13.8 mmol) in small portions over 5'. The reaction mixture was warmed to rt and stirred 4 h then diluted with EtOAc (300 mL), the organic phase was washed with 10% citric acid 2×100 mL, saturated $NaHCO_3$ 2×50 mL, brine and dried over $Na_2SO_4$. The organic phase was evaporated under reduced pressure to furnish the product (3.24 g, 83% yield). HPLC: Rt=7.190 min following Method HH. ES–MS: calcd. for $C_{21}H_{23}NO_4$ (353.41). Found: 353.2 [M+].

Step 3: To a stirred 0° C. solution of (2S,3S)-methyl-3-hydroxy-1-(4'-ethylbiphenylcarbonyl) pyrrolidine-2-carboxylate (1.0 g, 2.83 mmol) and TPP (0.82 g, 3.53 mmol) in anhydrous THF (10 mL) was added DPPA (765 μL, 3.53 mmol) followed by DIAD (915 μL, 4.41 mmol) added dropwise over 5'. The reaction mixture was warmed to rt over 1 h and stirred 20 h then evaporated on to silica under reduced pressure. The resulting residue was chromatographed on silica using 10-25% EtOAc in hexanes as eluent to furnish the product (735 mg, 69% yield). 1H NMR (300 MHz, DMSO-d6): δ 7.72 (d, J=8.2 Hz, 2H), 7.62 (dd, J=8.0, 6.0 Hz, 4H), 7.32 (d, J=8.0 Hz, 2H), 4.48 (d, J=7.1 Hz, 1H), 3.80-3.70 (m, 1H), 3.66 (s, 3H), 3.64-3.52 (m, 2H), 2.65 (dd, J=15.1, 7.7 Hz, 1H), 2.04-1.97 (m, 1H), 1.91-1.69 (m, 1H), 1.21 (t, J=7.4 Hz, 3H); HPLC: Rt=4.155 min following Method II; ES–MS: calcd. for $C_{21}H_{22}N_4O_3$ (378.42). Found: 377.0 [M–H].

Step 4: A solution of (2S,3R)-methyl-3-azido-1-(4'-ethylbiphenylcarbonyl)pyrrolidine-2-carboxylate (300 mg, 0.793 mmol) in THF/H2O/AcOH, 4:1:1 (6 mL) was added to 10% Pd/C Degussa 50% w/w wet form (150 mg). The reaction mixture was shaken under 35 psi $H_2$ atmosphere for 5 h then filtered through celite and evaporated under reduced pressure. The resulting residue was lyophilized from MeCN/H2O 1:1 to furnish the product (311 mg, 95% yield). 1H NMR (300 MHz, DMSO-d6): δ 7.75 (d, J=8.2 Hz, 2H), 7.62 (d, J=8.0 Hz, 4H), 7.33 (d, J=8.0 Hz, 2H), 6.55 (brs, 2H), 4.63 (d, J=6.9 Hz, 1H), 3.82-3.76 (m, 1H), 3.72 (s, 3H), 3.64-3.53 (m, 1H), 2.65 (dd, J=15.1, 7.4 Hz, 2H), 2.20-2.14 (m, 1H), 1.96-1.91 (m, 1H), 1.21 (t, J=7.6 Hz, 3H); HPLC: Rt=4.691 min following Method HH; ES+MS: calcd. for $C_{21}H_{24}N_2O_3$ (352.43). Found: 353.2 [M+H].

Step 5: (2S,3R)-3-Amino-N-hydroxy-1-(4'-ethylbiphenylcarbonyl)pyrrolidine-2-carborxamide was prepared from (2S,3R)-methyl-3-amino-1-(4'-ethylbiphenylcarbonyl)pyrrolidine-2-carboxylate by Method GG. 1H NMR (400 MHz, DMSO-d6): δ 7.70-7.52 (m, 6H), 7.34-7.31 (d, J=8.4 Hz, 2H), 6.76 (m, 1H), 6.53 (m, 1H), 4.95-4.80 (m, 1H), 4.36-4.34 (d, J=7.6 Hz, 1H), 4.08-3.93 (m, 1H), 3.69-3.32 (m 2H). 2.65 (dd, J=14.8, 7.6 Hz, 2H), 1.91 (m, 2H), 1.21 (t, J=7.6 Hz, 3H); HPLC: Rt=4.401 min following Method HH; ES–MS: calcd. for $C_{20}H_{23}N_3O_3$ (353.17). Found: 352.2 [M–H].

Example 35

Step 1: (S)-(tert-Butoxycarbonyl)thiazolidine-2-carboxylic acid was prepared following Method A using the commercially available (S)-2-thiazolidinecarboxylic acid (yield=96%). 1H NMR (DMSO-d6): 5.29-5.22 (bs, 1H), 4.52 (bs, 2H), 3.64-3.52 (m, 2H), 1.55 (bs, 9H). ES–MS: calcd. for $C_9H_{15}NO_4S$ (233.07). Found: 256.2 [M+Na].

Step 2: (S)-tert-Butyl 2-(benzyloxycarbamoyl)thiazolidine-3-carboxylate was prepared from (S)-(tert-Butoxycarbonyl)thiazolidine-2-carboxylic acid and O-benzyl hydroxylamine following Method G (yield=67%). 1H NMR (DMSO-d6): 11.474 (bs, 1H), 7.6-7.55 (m, 5H), 4.97 (bs, 1H), 3.94-3.8 (m, 2H), 3.44-3.23 (m, 2H), 1.58-1.53 (m, 9H). HPLC: Rt=5.293 min following Method R. ES–MS: calcd. for $C_{16}H_{22}N_2O_4S$ (338.13). Found: 337.2 [M–H].

Step 3: (S)—N-(Benzyloxy)thiazolidine-2-carboxamide hydrochloride salt was prepared from (S)-tert-butyl 2-(benzyloxycarbamoyl)thiazolidine-3-carboxylate following Method F (quantitative yield) 1H NMR (DMSO-d6): 11.91 (bs, 1H), 7.4-7.33 (m, 5H), 5.07 (s, 1H), 4.82 (m, 2H), 3.67-3.56 (m, 2H), 3.55-3.46 (m, 2H), 3.2-3.15 (m, 2H). ES–MS: calcd. for $C_{11}H_{14}N_2O_2S$ (238.08). Found: 239.1 [M+H].

Step 4: (S)—N-(Benzyloxy)3-(4-phenoxybenzoyl)-thiazolidine-2-carboxamide was prepared from (S)—N-(benzyloxy)thiazolidine-2-carboxamide hydrochloride salt and 4-(phenoxyphenyl)-carboxylic acid following Method G (yield=48%). 1H NMR (DMSO-d6): 11.32 (bs, 1H), 7.51-7.36 (m, 9H), 7.23-7.19 (m, 1H), 7.09-6.99 (m, 4H), 5.41 (bs, 1H), 4.76 (s, 2H), 3.95-3.87 (m, 2H), 3.19-3.10 (m, 2H). HPLC: Rt=6.082 min following Method R. ES–MS: calcd. for $C_{24}H_{22}N_2O_4S$ (434.13). Found: 435.1 [M+H].

Step 5: (S)—N-Hydroxy-3-(4-phenoxybenzoyl)thiazolidinesulfone-2-carboxamide was prepared from (S)—N-(benzyloxy)3-(4-phenoxybenzoyl)-thiazolidine-2-carboxamide following Methods S and P (overall yield=20%). 1H NMR (DMSO-d6): 11.23 (bs, 1H), 7.58 (bs, 1H), 7.47-7.41 (m, 4H), 7.24-7.19 (m, 1H), 7.12-7.03 (m, 4H), 5.3 (bs, 1H), 4.05 (bs, 2H), 3.77-3.68 (m, 1H), 3.51-3.41 (m, 1H). HPLC: Rt=4.816 min following Method R. ES–MS: calcd. for $C_{17}H_{16}N_2O_6S$ (376.39). Found: 375.2 [M–H].

Example 36

Step 1: (S)-(tert-Butoxycarbonyl)thiazolidine-2-carboxylic acid was prepared following Method A using the commercially available (S)-2-thiazolidinecarboxylic acid (yield=96%). 1H NMR (DMSO-d6): 5.29-5.22 (bs, 1H), 4.52 (bs, 2H), 3.64-3.52 (m, 2H), 1.55 (bs, 9H). ES–MS: calcd. for $C_9H_{15}NO_4S$ (233.07). Found: 256.2 [M+Na].

Step 2: (S)-tert-Butyl 2-(benzyloxycarbamoyl)thiazolidine-3-carboxylate was prepared from (S)-(tert-Butoxycarbonyl)thiazolidine-2-carboxylic acid and O-benzyl hydroxylamine following Method G (yield=67%). 1H NMR (DMSO-d6): 11.474 (bs, 1H), 7.6-7.55 (m, 5H), 4.97 (bs, 1H), 3.94-3.8 (m, 2H), 3.44-3.23 (m, 2H), 1.58-1.53 (m, 9H). HPLC: Rt=5.293 min following Method R. ES–MS: calcd. for $C_{16}H_{22}N_2O_4S$ (338.13). Found: 337.2 [M−H].

Step 3: (S)—N-(Benzyloxy)thiazolidine-2-carboxamide hydrochloride salt was prepared from (S)-tert-butyl 2-(benzyloxycarbamoyl)thiazolidine-3-carboxylate following Method F (quantitative yield) 1H NMR (DMSO-d6): 11.91 (bs, 1H), 7.4-7.33 (m, 5H), 5.07 (s, 1H), 4.82 (m, 2H), 3.67-3.56 (m 2H), 3.55-3.46 (m, 2H), 3.2-3.15 (m, 2H). ES–MS: calcd. for $C_{11}H_{14}N_2O_2S$ (238.08). Found: 239.1 [M+].

Step 4: (S)—N-(Benzyloxy)-3-(3',5'-difluorobiphenylcarbonyl)thiazolidine-2-carboxamide was prepared from (S)—N-(benzyloxy)thiazolidine-2-carboxamide hydrochloride salt and 3-(3',5'-difluorobiphenyl)-carboxylic acid following Method G (yield=48%). 1H NMR (DMSO-d6): 11.61 (bs, 1H), 8.04-8.02 (d, J=6.32 Hz, 2H), 7.83-7.81 (d, J=5.22 Hz, 2H), 7.70-7.68 (d, J=6.32 Hz, 2H), 7.57-7.44 (m, 6H), 5.67 (bs, 1H), 4.98 (s, 2H), 4.07-4.05 (m, 2H), 3.38-3.31 (m, 2H). HPLC: Rt=6.322 min following Method R. ES–MS: calcd. for $C_{24}H_{20}F_2N_2O_3S$ (454.12). Found: 453.2 [M−H].

Step 5: (S)—N-(Benzyloxy)3-(3',5'-difluorobiphenylcarbonyl)thiazoldinesulfone-2-carboxamide was prepared from (S)—N-(Benzyloxy)-3-(3',5'-difluorobiphenylcarbonyl) thiazolidine-2-carboxamide following Method S (yield=48%). 1H NMR (DMSO-d6): 12.15 (bs, 1H), 8.08-8.06 (dd, J=2.2 & 2.75 Hz, 2H), 7.88-7.85 (d, J=8.24 Hz, 2H), 7.71-7.69 (d, J=7.97 Hz, 2H), 7.55-7.45 (m, 6H), 5.45 (bs, 1H), 4.99 (bs, 2H), 4.24 (bs, 2H), 3.94 (bs, 1H), 3.72-3.68 (m, 1H). HPLC: Rt=6.222 min following Method R. ES–MS: calcd. for $C_{24}H_{20}F_2N_2O_5S$ (486.11). Found: 485 [M−H].

Step 6: (S)-3-(3',5'-Difluorobiphenylcarbonyl)-N-hydroxythiazolidinesulfone-2-carboxamide was prepared from (S)—N-(Benzyloxy)3-(3',5'-difluorobiphenylcarbonyl)-thiazolidinesulfone-2-carboxamide following Method P (yield=20%). 1H NMR (DMSO-d6): 11.27-10.91 (m, 1H), 9.47 (bs, 1H), 7.89-7.87 (d, J=7.42 Hz, 2H), 7.67 (s, 2H), 7.54-7.51 (d, J=7.14 Hz, 2H), 7.29 (s, 1H), 5.3 (bs, 1H), 4.04 (bs, 2H), 3.72 (bs, 2H). HPLC: Rt=5.054 min following Method R. ES–MS: calcd. for $C_{17}H_{14}F_2N_2O_5S$ (396.37). Found: 395.2 [M−H].

Example 37

Step 1: (S)-(tert-Butoxycarbonyl)thiazolidine-2-carboxylic acid was prepared following Method A using the commercially available (S)-2-thiazolidinecarboxylic acid (yield=96%). 1H NMR (DMSO-d6): 5.29-5.22 (bs, 1H), 4.52 (bs, 2H), 3.64-3.52 (m, 2H), 1.55 (bs, 9H). ES–MS: calcd. for $C_9H_{15}NO_4S$ (233.07). Found: 256.2 [M+Na].

Step 2: (S)-tert-Butyl 2-(benzyloxycarbamoyl)thiazolidine-3-carboxylate was prepared from (S)-(tert-Butoxycarbonyl)thiazolidine-2-carboxylic acid and O-benzyl hydroxylamine following Method G (yield=67%). 1H NMR (DMSO-d6): 11.474 (bs, 1H), 7.6-7.55 (m, 5H), 4.97 (bs, 1H), 3.94-3.8 (m, 2H), 3.44-3.23 (m, 2H), 1.58-1.53 (m, 9H). HPLC: Rt=5.293 min following Method R. ES–MS: calcd. for $C_{16}H_{22}N_2O_4S$ (338.13). Found: 337.2 [M−H].

Step 3: (S)—N-(Benzyloxy)thiazolidine-2-carboxamide hydrochloride salt was prepared from (S)-tert-butyl 2-(benzyloxycarbamoyl)thiazolidine-3-carboxylate following Method F (quantitative yield) 1H NMR (DMSO-d6): 11.91 (bs, 1H), 7.4-7.33 (m, 5H), 5.07 (s, 1H), 4.82 (m, 2H), 3.67-3.56 (m, 2H), 3.55-3.46 (m, 2H), 3.2-3.15 (m, 2H). ES–MS: calcd. for $C_{11}H_{14}N_2O_2S$ (238.08). Found: 239.1 [M+H].

Step 4: (S)—N-(Benzyloxy)3-(4'-fluorobiphenylcarbonyl)thiazolidine-2-carboxamide was prepared from (S)—N-(benzyloxy)thiazolidine-2-carboxamide hydrochloride salt and 3-(4'-fluorobiphenyl)-carboxylic acid following Method G (yield=48%). 1H NMR (DMSO-d6): 11.61 (bs, 1H), 8.13-7.82 (m, 5H), 7.57-7.48 (m, 8H), 5.66 (bs, 1H), 4.97 (s, 2H), 4.08-4.05 (d, J=5.22 Hz, 2H), 3.38-3.3 (m, 2H). HPLC: Rt=6.217 min following Method R. ES–MS: calcd. for $C_{24}H_{21}FN_2O_3S$ (436.13). Found: 435 [M−H].

Step 5: (S)—N-(Benzyloxy)3-(4'-fluorobiphenylcarbonyl)-thiazolidinesulfone-2-carboxamide was prepared from (S)—N-(Benzyloxy)3-(4'-fluorobiphenylcarbonyl)thiazolidine-2-carboxamide following Method S (yield=48%). HPLC: Rt=6.086 min following Method R. ES–MS: calcd. for $C_{24}H_{21}FN_2O_3S$ (468.12). Found: 469 [M+H].

Step 6: (S)-3-(4'-Fluorobiphenylcarbonyl)-N-hydroxythiazolidinesulfone-2-carboxamide was prepared from (S)—N-(benzyloxy)3-(4'-fluoroybiphenylcarbonyl)-thiazolidinesulfone-2-carboxamide following Method P (yield=20%). 1H NMR (DMSO-d6): 11.45 (m, 1H), 9.65 (bs, 1H), 7.97-7.85 (m, 5H), 7.54-7.48 (t, J=8.52 & 9.07 Hz, 2H), 6.74 (bs, 1H), 5.5 (bs, 1H), 4.25 (bs, 2H), 3.93 (bs, 1H), 3.63 (bs, 1H). HPLC: Rt=4.859 min following Method R. ES–MS: calcd. for $C_{17}H_{15}FN_2O_5S$ (378.37). Found: 377.2 [M−H].

Example 38

Step 1: (S)-(tert-Butoxycarbonyl)thiazolidine-2-carboxylic acid was prepared following Method A using the commercially available (S)-2-thiazolidinecarboxylic acid (yield=96%). 1H NMR (DMSO-d6): 5.29-5.22 (bs, 1H), 4.52 (bs, 2H), 3.64-3.52 (m, 2H), 1.55 (bs, 9H). ES–MS: calcd. for $C_9H_{15}NO_4S$ (233.07). Found: 256.2 [M+Na].

Step 2: (S)-tert-Butyl 2-(benzyloxycarbamoyl)thiazolidine-3-carboxylate was prepared from (S)-(tert-Butoxycarbonyl)thiazolidine-2-carboxylic acid and O-benzyl hydroxylamine following Method G (yield=67%). 1H NMR (DMSO-d6): 11.474 (bs, 1H), 7.6-7.55 (m, 5H), 4.97 (bs, 1H), 3.94-3.8 (m, 2H), 3.44-3.23 (m, 2H), 1.58-1.53 (m, 9H). HPLC: Rt=5.293 min following Method R. ES–MS: calcd. for $C_{16}H_{22}N_2O_4S$ (338.13). Found: 337.2 [M−H].

Step 3: (S)—N-(Benzyloxy)thiazolidine-2-carboxamide hydrochloride salt was prepared from (S)-tert-butyl 2-(benzyloxycarbamoyl)thiazolidine-3-carboxylate following Method F (quantitative yield) 1H NMR (DMSO-d6): 11.91 (bs, 1H), 7.4-7.33 (m, 5H), 5.07 (s, 1H), 4.82 (m, 2H), 3.67-3.56 (m, 2H), 3.55-3.46 (m, 2H), 3.2-3.15 (m, 2H). ES–MS: calcd. for $C_{11}H_{14}N_2O_2S$ (238.08). Found: 239.1 [M+H].

Step 4: (S)—N-(Benzyloxy)3-(4'-(trifluoromethyl)biphenylcarbonyl)-thiazoldine-2-carboxamide was prepared from (S)—N-(benzyloxy)thiazolidine-2-carboxamide hydrochloride salt and 3-(4'-(trifluoromethyl)biphenyl)-carboxylic acid following Method G (yield=48%). 1H NMR (DMSO-d6): 12.07 (bs, 1H), 8.23-7.96 (m, 5H), 7.86-7.83 (d, J=8.24 Hz, 2H), 7.67-7.48 (m, 6H), 5.67 (bs, 1H), 4.98 (bs, 2H), 4.08 (bs, 2H), 3.38-3.22 (m, 2H). HPLC: Rt=6.606 min following Method R. ES–MS: calcd. for $C_{24}H_{21}F_3N_2O_3S$ (486.12). Found: 485.2 [M−H].

Step 5: (S)—N-(Benzyloxy)3-(4'-(trifluoromethyl)biphenylcarbonyl)thiazolidinesulfone-2-carboxamide was prepared from (S)—N-(benzyloxy)3-(4'-(trifluoromethyl)biphenylcarbonyl)-thiazolidine-2-carboxamide following Method S (yield=48%). 1H NMR (DMSO-d6): 12.16 (bs, 1H), 8.08-8.05 (dd, J=2.2 & 4.12 Hz, 5H), 7.89-7.86 (d, J=6.87 Hz, 2H), 7.74-7.56 (m, 6H), 5.45 (bs, 1H), 4.99 (bs, 2H), 4.25 (bs, 2H), 3.96 (bs, 1H), 3.72-3.68 (t, J=7.14 & 5.77 Hz, 1H). HPLC: Rt=6.514 min following Method R. ES–MS: calcd. for $C_{25}H_{21}F_3N_2O_5S$ (518.11). Found: 517.2 [M–H].

Step 6: (S)-3-(4'-(Trifluoromethyl)biphenylcarbonyl)-N-hydroxythiazolidinesulfone-2-carboxamide was prepared from (S)—N-(benzyloxy)3-(4'-(trifluoromethyl)biphenylcarbonyl)-thiazolidinesulfone-2-carboxamide following Method P (yield=20%). 1H NMR (DMSO-d6): 11.46 (bs, 1H), 9.65 (bs, 1H), 8.16-7.89 (m, 6H), 6.72 (bs, 2H), 6.74 (bs, 1H), 5.5 (bs, 1H), 4.25 (bs, 2H), 3.92 (bs, 1H), 3.62 (bs, 1H). HPLC: Rt=5.532 min following Method R. ES–MS: calcd. for $C_{18}H_{15}F_3N_2O_5S$ (428.39). Found: 427.2 [M–H].

Example 39

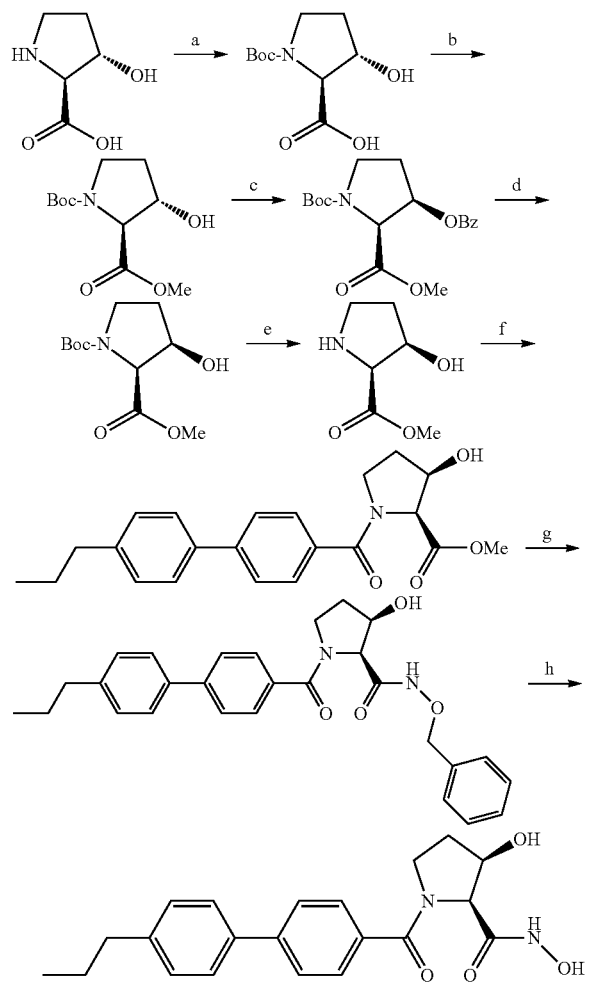

Reagents and conditions. Step 1: Protection ($Boc_2O$, base); Step 2: Methyl ester formation ($TMSCHN_2$, MeOH); Step 3: Inversion ($Ph_3P$, DIAD, Benzoic acid, THF); Step 4: De-O-benzylation (NaOMe, MeOH); Step 5: Deprotection (4M HCl/Dioxane); Step 6: Coupling (ArCOOH, HATU, DIEA, DMF); Step 7: Amidation ($Me_3Al$, $NH_2$—OBn.HCl, Toluene); Step 8: Hydroxamate formation (10% $Pd(OH)_2$/C, EtOH).

Step 1: (2S,3S)-1-(tert-Butoxycarbonyl)-3-hydroxypyrrolidine-2-carboxylic acid was prepared from (2S,3S)-3-Hydroxypyrrolidine-2-carboxylic acid following Method A (yield=91%). The resulting product was used without purification. 1H NMR (DMSO-d6): 5.64-5.63 (d, 1H), 4.42 (bs, 1H), 4.13-4.1 (d, 1H), 3.64-3.48 (m, 2H), 2.11-1.99 (m, 2H), 1.58-1.52 (d, 9H). HPLC: Rt=3.868 min following Method R. ES–MS: calcd. for $C_{10}H_{17}NO_5$ (231.25). Found: 230.2 [M–H].

Step 2: (2S,3S)-1-tert-Butyl 2-methyl 3-hydroxypyrrolidine-1,2-dicarboxylate was prepared from (2S,3S)-1-(tert-butoxycarbonyl)-3-hydroxypyrrolidine-2-carboxylic acid following Method B (quantitative yield). 1H NMR (DMSO-d6): 4.44-4.42 (m, 1H), 4.3-4.2 (d, 1H), 3.75 (s, 3H), 3.68-3.56 (m, 2H), 2.18-2.08 (m, 1H), 1.94-1.75 (m, 1H), 1.47-1.41 (d, 9H). HPLC: Rt=4.45 min following Method R. ES–MS: calcd. for $C_{11}H_{19}N_2O_5$ (245.13). Found: 268.3 [M+Na].

Step 3: (2S,3R)-1-tert-Butyl 2-methyl 3-hydroxypyrrolidine-1,2-dicarboxylate was prepared from (2S,3S)-1-tert-butyl 2-methyl 3-hydroxypyrrolidine-1,2-dicarboxylate following Methods C and D. (overall yield=90%). 1H NMR (DMSO-d6): 4.65-4.61 (m, 1H), 4.26-4.25 (d, J=2.73 Hz, 1H), 3.89-3.87 (d, J=7.41 Hz, 3H), 3.83-3.52 (m, 2H), 2.32-2.12 (m, 2H), 1.47-1.42 (d, J=20.6 Hz, 9H). HPLC: Rt=4.43 min following Method R. ES–MS: calcd. for $C_{11}H_{19}N_2O_5$ (245.13). Found: 268.3 [M+Na].

Step 5: (2S,3R)-Methyl 3-hydroxypyrrolidine-2-carboxylate hydrochloride salt was prepared from (2S,3R)-1-tert-butyl 2-methyl 3-hydroxypyrrolidine-1,2-dicarboxylate following Method F (quantitative yield). 1H NMR (DMSO-d6): 5.86-5.68 (dd, J=1.65 & 2.74 Hz, 1H), 4.93-4.85 (d, J=22.8 Hz, 1H), 3.98 (s, 3H), 3.68-3.49 (m, 2H), 2.49-2.3 (m, 2H). ES–MS: calcd. for $C_6H_{10}FNO_2$ (147.15). Found 148.2 [M+H].

Step 6: (2S,3R)-Methyl 3-hydroxy-1-(4'-propylbiphenylcarbonyl)pyrrolidine-2-carboxylate was prepared from (2S,3R)-methyl 3-hydroxypyrrolidine-2-carboxylate hydrochloride salt and 4-(p-n-propylphenyl)-benzoic acid following Method G (yield=78%). 1H NMR (DMSO-d6): 7.74-7.72 (d, J=8.24 Hz, 2H), 7.64-7.6 (dd, J=2.2 & 2.47 Hz, 4H), 7.31-7.29 (d, J=7.97 Hz, 2H), 5.51-5.49 (d, J=4.12 Hz, 1H), 4.58-4.49 (m, 2H), 3.72 (s, 3H), 3.78-3.69 (m, 1H), 3.63 (s, 3H), 3.6-3.51 (m, 1H), 2.61-2.56 (t, J=7.69 & 7.42 Hz, 2H), 1.98-1.82 (m, 2H), 1.67-1.55 (m, 2H), 0.93-0.88 (t, J=7.14 & 7.42 Hz, 3H). HPLC: Rt=6.32 min following Method R. ES–MS: calcd. for $C_{22}H_{25}NO_4$ (367.18). Found: 368.3 [M+H].

Step 7: (2S,3R)—N-(Benzyloxy)-3-hydroxy-1-(4'-propylbiphenylcarbonyl)pyrrolidine-2-carboxamide was prepared from (2S,3R)-methyl 3-hydroxy-1-(4'-propylbiphenylcarbonyl)pyrrolidine-2-carboxylate following Method I (yield=80%). 1H NMR (DMSO-d6): 11.102 (bs, 1H), 7.74-7.54 (m, 6H), 7.45-7.27 (m, 7H), 5.33 (s, 1H), 4.79 (bs, 1H), 4.43-4.35 (m, 2H), 3.76-3.7 (m, 1H), 3.48-3.39 (m, 1H), 2.62-2.57 (t, J=7.42 & 7.69 Hz, 2H), 1.9-1.88 (d, J=6.04 Hz, 2H), 1.68-1.55 (m, 2H), 0.93-0.87 (m, 3H). HPLC: Rt=6.53 min following Method R. ES–MS: calcd. for $C_{29}H_{30}N_2O_4$ (458.22). Found: 457.2 [M–H].

Step 8: (2S,3R)-3-Hydroxy-N-hydroxy-1-(4'-propylbiphenylcarbonyl)pyrrolidine-2-carboxamide was prepared from (2S,3R)—N-(benzyloxy)-3-hydroxy-1-(4'-propylbiphenylcarbonyl)pyrrolidine-2-carboxamide following Method P (yield=25%). 1H NMR (DMSO-d6): 10.41 (bs, 1H), 7.73-7.61 (m, 6H), 7.39-7.28 (m, 2H), 4.42 (bs, 1H), 4.37 (bs, 1H), 3.73-3.45 (m, 3H), 2.62-2.57 (t, J=7.42 & 7.69 Hz, 2H), 1.88 (bs, 2H), 1.86-1.60 (m, 2H), 0.93-0.88 (t, J=7.42 & 7.14 Hz, 3H). HPLC: Rt=5.73 min following Method R. ES–MS: calcd. for $C_{21}H_{24}N_2O_4$ (368.43). Found 367.2 [M–H].

Example 40

(2S,3R)-3-Hydroxy-N-hydroxy-1-(4-methoxy-3-trifluoromethylsulfanyl-benzoyl)-pyrrolidine-2-carboxamide

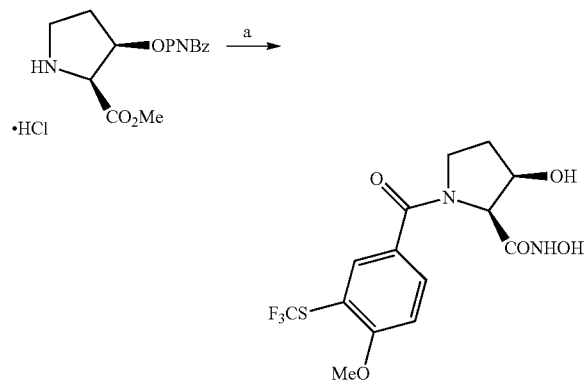

Reagents and conditions. 4-methoxy-3-trifluoromethylsulfanyl-benzoic acid, HATU, DIEA, dioxane ii. 50% Aq. $NH_2OH$.

To a stirred solution of (2S,3R)-3-(4-nitro-benzoyloxy)-pyrrolidine-2-carboxylic acid methy ester hydrochloride salt prepared by Method C followed by Method F (109 mg, 0.33 mmol), 4-methoxy-3-trifluoromethylsulfanyl-benzoic acid (76.6 mg, 0.30 mmol), in anhydrous dioxane (2.0 mL) was added HATU (136 mg, 0.36 mmol) and DIEA (205 μL, 1.2 mmol) with rapid stirring. The reaction mixture was stirred 2 h at rt then diluted with 50% aq. hydroxylamine (2.0 mL) and stirred an additional 17 h. The crude reaction mixture was purified by preparative reverse phase HPLC to furnish the product (2S,3R)-3-hydroxy-N-hydroxy-1-(4-methoxy-3-trifluoromethylsulfanyl-benzoyl)-pyrrolidine-2-carboxamide (4.0 mg, 4% yield). HPLC: Rt=4.050 min following Method HH; ES–MS: calcd. for $C_{14}H_{15}F_3N_2O_5S$ (380.07). Found: 379.0 [M–H].

Example A

Susceptibility Testing

Compounds were tested following the microdilution method of CLSI (Clinical and Laboratory Standards Institute. Methods for dilution antimicrobial susceptibility tests for bacteria that grow aerobically; Approved standard—sixth edition. CLSI document M7-A5, CLSI, Wayne, Pa. 2003). Assays were performed in sterile plastic 96-well microtiter trays with round bottom wells (Greiner).

Compound Preparation

Stock solutions of test compounds and control antibiotics were prepared at 10 mg/ml in DMSO. Serial 2-fold dilutions of each drug were performed in a microtiter plate across each row using DMSO as solvent at 100-fold the desired final concentration. Wells in columns #1-11 contain drug and column #12 was kept as a growth control for the organism with no drug. Each well in the mother plate was diluted with sterile deionized water and DMSO, mixed, and volumes of 10 μl distributed to each well in the resulting assay plates.

Preparation of Inoculum

Stock cultures were prepared using the Microbank™ method (Pro-Lab Diagnostics) and stored at −80° C. To propagate each strain, one bead was removed from the frozen vial and aseptically streaked onto Trypticase Soy Agar (Difco) which were incubated at 35° C. Standardized inocula were prepared using the direct colony suspension method according to CLSI guidelines (Clinical and Laboratory Standards Institute. Methods for dilution antimicrobial susceptibility tests for bacteria that grow aerobically; Approved standard—sixth edition. CLSI document M7-A5, CLSI, Wayne, Pa., 2003). Isolated colonies were selected from an 18-24 hr agar plate and resuspended in 0.9% sterile saline to match a 0.5 McFarland turbidity standard using a calorimeter (Vitek) at 80% of transmitance. The suspension was used within 15 minutes of preparation.

| | |
|---|---|
| *Escherichia coli* VECO1003 | *Escherichia coli* ATCC 25922 |
| *Escherichia coli* VECO2096 | *Escherichia coli* MG1655 |
| *Escherichia coli* VECO2526 tolC | *Escherichia coli* MG1655 tolC |
| *Enterobacter cloacae* VECL1001 | *Enterobacter cloacae* ATCC 35030 |
| *Klebsiella pneumoniae* VKPN1001 | *Klebsiella pneumoniae* ATCC 10031 |
| *Morganella morganii* VMMO1001 | *Morganella morganii* ATCC 25830 |
| *Pseudomonas aeruginosa* VPAE1004 | *Pseudomonas aeruginosa* ATCC 27853 |
| *Pseudomonas aeruginosa* VPAE1010 | *Pseudomonas aeruginosa* K799 |
| *Pseudomonas aeruginosa* VPAE1011 | K799/61 (Δ efflux, hypersusceptible strain) |
| *Haemophilus influenzae* VHIN1001 | *Haemophilus influenzae* ATCC 49247 |
| *Staphylococcus aureus* VSAU1001 | *Staphylococcus aureus* ATCC 29213 |

Preparation of Assay Plates for MICs

Mueller-Hinton Broth (MHB) (Difco) was prepared at a 1.1× concentration and supplemented with Ca++ and Mg++ as recommended by CLSI. For each organism, the standardized suspension was diluted 1:180 into appropriate growth medium in a sterile reservoir. After mixing, wells in the drug-containing assay plates were inoculated with a volume of 90 μl. Thus, for each minimum inhibitory concentration (MIC) determination, each well contains a final volume of 100 μl with an inoculum size of approximately $5 \times 10^5$ colony forming units (cfu)/ml and no more than 1% DMSO.

Interpretation of MIC

The completed microtiter plates were incubated 20 h at 35° C. in ambient air. Optical density of each well was determined at 600 nm using a VersaMax Microplate reader (Molecular Devices, Sunnyvale, Calif.). The MIC was defined as the lowest drug concentration causing complete suppression of visible bacterial growth.

Example B

Efficacy in Murine *E. coli* Septicemia

Efficacy studies were performed in an *E. coli* murine septicemia model according to models published elsewhere (Goldstein, B. P., G. Candiani, T. M. Arain, G. Romano, I. Ciciliato, M. Berti, M. Abbondi, R. Scotti, M. Mainini, F. Ripamonti, and et al. 1995). Antimicrobial activity of MDL 63,246, a new semisynthetic glycopeptide antibiotic Antimicrob Agents Chemother. 39:1580-1588.; Misiek, M., T. A. Pursiano, F. Leitner, and K. E. Price 1973. Microbiological properties of a new cephalosporin, BL-S 339: 7-(phenylacetimidoyl-aminoacetamido)-3-(2-methyl-1,3,4-thiadiazol-5-ylthio methyl)ceph-3-em-4-carboxylic acid Antimicrob Agents Chemother. 3:40-48).

Compound Preparation

The compound was dissolved in 10% DMSO, 0.1% Tween 80, 0.9% NaCl solution and administered intravenously at 10 ml/kg at 1 hour after bacterial inoculation. The compound was administered at 80, 40, 20, 5, 2.5, and 1.25 mg/kg. A control with ampicillin was included in the evaluation.

Efficacy Model

Male or female ICR mice weighing 22±2 g from MDS Pharma Services were used for the evaluation. Food and water was given ad libitum. Groups of 6 mice weighing 22± g were used for the experiment. Mice were inoculated intraperitoneally with *Escherichia coli* ATCC 25922 at $4 \times 10^4$ CFU in 0.5 ml of Brain Heart Infusion Broth (Difco) containing 5% mucin (Sigma). Mortality was recorded once daily for 7 days following bacterial inoculation. The ED50 was determined by non-linear regression and is 28.3 for the compound and 14.1 for ampicillin.

Enzyme Inhibition Testing

Compounds were tested based on a published method (Wang W., 2001, Anal Biochem, 290, 338-46) with modifications. Enzyme assays were performed in the assay buffer (50 mM HEPES, pH8, 0.005% Brij, 50 μM ZnSO4, 1 mg/ml BSA) in 96-well V-bottom microtiter plates.

Compound Preparation

Stock solutions of test compounds and control antibiotics are prepared at 10 mg/ml in DMSO and are diluted in the assay buffer to 6-fold the final testing concentration. 5 μl compound dilution is distributed to the well of the assay plate. EDTA is used as positive control and the final concentration in assay is 12.5 mM.

Enzyme Inhibition Assay

P. ae LpxC enzyme dilution in the assay buffer is added to the compound in plate and pre-incubated with the compound at room temperature for 10 min. LpxC substrate is added to initiate the enzyme reaction and the final enzyme and substrate concentrations are 1.2 μM and 0.4 mM, respectively. The reaction continues at RT for 4 hrs before diluted with 45 μl of Borate buffer (0.4 M, pH9), followed by addition of 40 μl derivatization reagent (fluorescamine 2 mg/ml DMF). This mixture is incubated at RT for 10 min followed by addition of 150 μl DMF/$H_2O$ (1:1). The resulting solution is loaded onto Millipore filter unit (Microcon 10 k MWCO) and spun at 13 k rpm on bench top centrifuge for 15 min. 100 μl of this filtrate is transferred to a low fluorescence clear-bottom 96-well plate (Corning) and the fluorescence is detected at ex360 nm and em465 nm on a Tecan fluorescence plate reader. The percent inhibition is calculated based on EDTA produces 100% inhibition and negative control produces 100% activity.

The above methods may be used to test compounds described herein. Results are summarized in Table 3 below.

TABLE 3

| Compound | E. coli (2) | E. coli tolC | P. aerug. (2) | P. aerug. Hypersuc | K. pneu. | H. influen. | ENZYME |
|---|---|---|---|---|---|---|---|
| 1 | >64 | 32 | >64 | >64 | >64 | >64 | 35 (@0.5 μg/ml) |
| 2 | 64 | 32 | 64->64 | 64 | 64 | 16 | 65 (@0.5 μg/ml) |
| 3 | >64 | 32 | >64 | >64 | >64 | >64 | 55 (@0.5 μg/ml) |
| 4 | >64 | 32 | >64 | 64 | >64 | >64 | 69 (@0.5 μg/ml) |
| 5 | 64 | 32 | >64 | 64 | >64 | 32 | 29 (@0.5 μg/ml) |
| 6 | >64 | 16 | >64 | 32 | 32 | >64 | 87 (@0.5 μg/ml) |
| 7 | 64->64 | 64 | >64 | 64 | 64 | >64 | 84 (@10 μg/ml) |
| 8 | >64 | 32 | >64 | >64 | >64 | 64 | 21 (@10 μg/ml) |
| 9 | >64 | >64 | >64 | 32 | >64 | >64 | 57 (@1 μg/ml) |
| 10 | >64 | 64 | >64 | 64 | >64 | >64 | 60 (@0.5 μg/ml) |
| 11 | >64 | 32 | 64 | 16 | >64 | 32 | 84 (@0.5 μg/ml) |
| 12 | >64 | >64 | 32->64 | 8 | >64 | 32 | 95 (@0.5 μg/ml) |
| 13 | >64 | >64 | 64 | 16 | 32 | 64 | 71 (@10 μg/ml) |
| 14 | >64 | 16 | 32 | 8 | 64 | >64 | 99 (@0.5 μg/ml) |
| 15 | 16 | 2 | 8 | 2 | 4 | 32 | 41 (@0.1 μg/ml) |
| 16 | >64 | 16 | >64 | 16 | >64 | >64 | 57 (@0.5 μg/ml) |
| 17 | 32->64 | 8 | 16 | 2 | 16 | >64 | 98 (@0.5 μg/ml) |

TABLE 3-continued

| Compound | E. coli (2) | E. coli tolC | P. aerug. (2) | P. aerug. Hypersuc | K. pneu. | H. influen. | ENZYME |
|---|---|---|---|---|---|---|---|
| 18 | >64 | 16 | >64 | 32 | 32 | 64 | 50 (@0.5 µg/ml) |
| 19 | 8-16 | 2 | 8 | 2 | 4 | 32 | 10 (@0.1 µg/ml) |
| 20 | 0.5 | 0.25 | 16 | 1 | 0.5 | 0.25 | <10 (@0.1 µg/ml) |
| 21 | 16-32 | 4 | >64 | 16 | 8 | 8 | 77 (@0.5 µg/ml) |
| 22 | 2 | 0.25 | 16-32 | 0.5 | 1 | 0.5 | <10 (@0.1 µg/ml) |
| 23 | 16 | 8 | 8 | 2 | 16 | 16 | 24 (@0.1 µg/ml) |
| 24 | >64 | 16 | 32 | 2 | >64 | 8 | 13 (@0.1 µg/ml) |
| 25 | 8 | 4 | 8-16 | 2 | 16 | 4 | 12 (@0.1 µg/ml) |
| 26 | >64 | >64 | >64 | >64 | >64 | >64 | 72 (@0.5 µg/ml) |
| 27 | >64 | >64 | >64 | >64 | >64 | >64 | 38 (@0.1 µg/ml) |
| 28 | >64 | 32 | >64 | >64 | >64 | >64 | 13 (@0.1 µg/ml) |
| 29 | >64 | <=0.06 | >64 | 32 | 4 | >64 | 59 (@0.1 µg/ml) |
| 30 | 64 | 2 | >64 | 32 | 8 | 16 | 87 (@0.5 µg/ml) |
| 31 | >64 | 1 | >64 | 64 | >64 | >64 | 100 (@0.5 µg/ml) |
| 32 | 64->64 | 64 | >64 | >64 | >64 | >64 | <10 (@10 µg/ml) |
| 33 | >64 | <=0.06 | 4-16 | 2 | 32 | 16 | 12 (@0.1 µg/ml) |
| 34 | >64 | >64 | 16-32 | 64 | >64 | >64 | 93 (@0.5 µg/ml) |
| 35 | >64 | 0.125 | >64 | >64 | >64 | >64 | 21 (@0.1 µg/ml) |
| 36 | >64 | 0.125 | 32-16 | 8 | >64 | >64 | 8 (@0.1 µg/ml) |
| 37 | >64 | <=0.06 | 4-32 | 2 | >64 | >64 | 32; 42 (@0.1 µg/ml) |
| 38 | >64 | <=0.06 | 32 | 8 | >64 | >64 | 30 (@0.1 µg/ml) |
| 39 | >64 | 64 | 64->64 | 4 | >64 | >64 | 95.2 (@1 µg/ml) |
| 40 | >64 | 32 | >64 | >64 | 64 | >64 | 52 (@10 µg/ml) |

As used herein, reference to "a" or "an" means "one or more." Throughout, the plural and singular should be treated as interchangeable, other than the indication of number.

As will be understood by one skilled in the art, for any and all purposes, particularly in terms of providing a written description, all ranges disclosed herein also encompass any and all possible subranges and combinations of subranges thereof as well as the individual values making up the range, particularly integer values. Any listed range can be easily recognized as sufficiently describing and enabling the same range being broken down into at least equal halves, thirds, quarters, fifths, tenths, etc. As a non limiting example, each range discussed herein can be readily broken down into a lower third, middle third and upper third, etc. For example, the range $C_1$-$C_6$, includes the subranges $C_2$-$C_6$, $C_3$-$C_6$, $C_3$-$C_5$, $C_4$-$C_6$, etc., as well as $C_1$ (methl), $C_2$ (ethyl), $C_3$ (propyl), $C_4$ (butyl), $C_5$ (pentyl) and $C_6$ (hexyl) individually. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Additionally, for all purposes, the present invention encompasses not only the main group, but also the main group absent one or more of the group members. The present invention also envisages the explicit exclusion of one or more of any of the group members in the claimed invention.

As will be understood by the skilled artisan, all numbers, including those expressing quantities of ingredients, properties such as molecular weight, reaction conditions, and so forth, are approximations and understood as being modified in all instances by the term "about." These values can vary depending upon the desired properties sought to be obtained by those skilled in the art utilizing the present teachings of the present invention. It is also understood that such values inherently contain variability necessarily resulting from the standard deviations found in their respective testing measurements.

All references disclosed herein are specifically incorporated herein by reference thereto.

While specific embodiments have been illustrated and described, it should be understood that these embodiments do not limit the scope of the invention and that changes and modifications can be made in accordance with ordinary skill in the art without departing from the invention in its broader aspects as defined in the following claims. Reference to a "step" in the application is used for convenience purposes only and does not categorize, define or limit the invention as set forth herein.

What is claimed is:

1. A compound having the formula

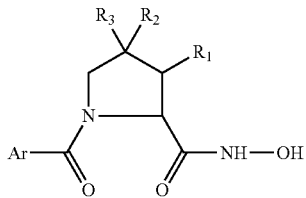

or a salt, thereof,
wherein $R_1$ is selected from the group consisting of H, $N_3$, $NH_2$, $NHSO_2CH_3$, NHCOH, $NHCH_3$, F, and $OCH_3$;
$R_2$ is selected from the group consisting of H, and $NH_2$;
$R_3$ is selected from the group consisting of H, and $CH_2OCH_3$, and;
Ar is represented by

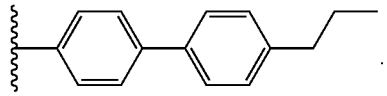

2. The compound of claim 1 wherein $R_1$ is H, and $R_3$ is $CH_2OCH_3$.

3. The compound of claim 1 wherein $R_1$ is selected from the group consisting of $N_3$, $NH_2$, $NHSO_2CH_3$, NHCOH, $NHCH_3$, F and $OCH_3$; $R_2$ is H and $R_3$ is H.

4. The compound of claim 3 wherein $R_1$ is $NH_2$.

5. The compound of claim 1 wherein $R_2$ is $NH_2$ and $R_3$ is H.

6. A method of treating a bacterial infection in a mammal in need thereof comprising administering an effective amount of a compound of claim 1 to the mammal.

7. The compound of claim 1 in which $R_1$, $R_2$ and $R_3$ are each represented by H.

* * * * *